US012558451B2

(12) United States Patent
Takeda et al.

(10) Patent No.: US 12,558,451 B2
(45) Date of Patent: Feb. 24, 2026

(54) ABSORBENT BODY, WATER-ABSORBING RESIN, AND ABSORBENT ARTICLE

(71) Applicant: NIPPON SHOKUBAI CO., LTD., Osaka (JP)

(72) Inventors: Daisuke Takeda, Himeji (JP); Reiko Nakatsuru, Himeji (JP); Keisuke Kikuchi, Himeji (JP); Tomoya Arai, Himeji (JP); Kenji Tada, Himeji (JP); Nobuya Tanaka, Himeji (JP); Kazuki Kimura, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 821 days.

(21) Appl. No.: 17/790,195

(22) PCT Filed: Dec. 22, 2020

(86) PCT No.: PCT/JP2020/047821
§ 371 (c)(1),
(2) Date: Jun. 30, 2022

(87) PCT Pub. No.: WO2021/140905
PCT Pub. Date: Jul. 15, 2021

(65) Prior Publication Data
US 2023/0050209 A1    Feb. 16, 2023

(30) Foreign Application Priority Data
Jan. 6, 2020    (JP) ................................. 2020-000122

(51) Int. Cl.
*A61L 15/60*        (2006.01)
*A61L 15/22*        (2006.01)
(Continued)

(52) U.S. Cl.
CPC ............... *A61L 15/60* (2013.01); *A61L 15/22* (2013.01); *B01J 20/267* (2013.01); *B01J 20/28004* (2013.01); *B01J 20/28047* (2013.01)

(58) Field of Classification Search
CPC .......... A61F 13/53; A61F 2013/530481; A61F 15/22; A61F 15/60; B01J 20/26;
(Continued)

(56) References Cited

U.S. PATENT DOCUMENTS 9,567,414 B2    2/2017  Nogi et al.
10,300,458 B2    5/2019  Torii et al.
(Continued)

FOREIGN PATENT DOCUMENTS

CN        105492505 A        4/2016
CN        105916475 A        8/2016
(Continued)

OTHER PUBLICATIONS

Office Action issued in Japanese Application No. JP 2021-569820 dated Jul. 25, 2023.
(Continued)

*Primary Examiner* — Brian A McCaig
(74) *Attorney, Agent, or Firm* — Harness Dickey & Pierce P.L.C.

(57) ABSTRACT

Provided is an absorbent body that, for example, in a case where the absorbent body has been used in an absorbent article, such as a thin disposable diaper, having an absorbent body with a low proportion of fiber material (hydrophilic fibers) such as pulp, enables the absorbent article such as a disposable diaper to have an improved liquid trapping function on second and subsequent urinations over the conventional ones and particularly to have an increased amount of liquid trapped under load on the second and subsequent urinations over the conventional ones. Also (Continued)

1

Cavity (Hollow that is connected to outside)

Void (Hollow that is not connected to outside)

provided is a water-absorbing resin that is used in the absorbent body and has an increased absorption capacity under load on the second and subsequent urinations over the conventional ones.

The absorbent body includes a water-absorbing resin having a gel expansion force under a load of 4.83 kPa of 26 N or more.

10 Claims, 7 Drawing Sheets

(51) Int. Cl.
   *B01J 20/26*        (2006.01)
   *B01J 20/28*        (2006.01)

(58) Field of Classification Search
   CPC .... B01J 20/267; B01J 20/28; B01J 20/28004; B01J 20/28011; B01J 20/28047; B01J 2220/68; C08F 8/14; C08F 220/16; C08F 220/28; A61L 15/22; A61L 15/60
   See application file for complete search history.

(56)            References Cited

U.S. PATENT DOCUMENTS

| | | |
|---|---|---|
| 2009/0208748 A1 | 8/2009 | Torii et al. |
| 2011/0313113 A1 | 12/2011 | Sakamoto et al. |
| 2012/0220745 A1 | 8/2012 | Machida et al. |
| 2012/0258851 A1* | 10/2012 | Nakatsuru ................ C08J 3/12 |
| | | 502/7 |
| 2013/0026412 A1 | 1/2013 | Machida et al. |
| 2013/0101851 A1 | 4/2013 | Takaai et al. |
| 2014/0193641 A1 | 7/2014 | Torii et al. |
| 2014/0296465 A1 | 10/2014 | Sakamoto et al. |
| 2015/0217270 A1 | 8/2015 | Ueda et al. |
| 2015/0259494 A1 | 9/2015 | Takaai et al. |
| 2016/0199529 A1 | 7/2016 | Torii et al. |
| 2016/0332141 A1 | 11/2016 | Machida et al. |
| 2017/0014801 A1 | 1/2017 | Ikeuchi et al. |
| 2018/0001300 A1 | 1/2018 | Nakatsuru et al. |
| 2018/0071714 A1 | 3/2018 | Torii et al. |
| 2018/0094131 A1* | 4/2018 | Tanaka .................... C08L 33/02 |
| 2018/0161756 A1 | 6/2018 | Omori et al. |
| 2019/0111411 A1 | 4/2019 | Torii et al. |
| 2019/0119452 A1 | 4/2019 | Yoon et al. |
| 2019/0275192 A1 | 9/2019 | Torii et al. |
| 2021/0115198 A1 | 4/2021 | Yorino et al. |
| 2021/0147637 A1 | 5/2021 | Matsumoto et al. |

FOREIGN PATENT DOCUMENTS

| | | | |
|---|---|---|---|
| EP | 2669318 A1 | 12/2013 |
| EP | 3202823 A1 | 8/2017 |
| EP | 3241861 A1 | 11/2017 |
| EP | 3260485 A1 | 12/2017 |
| EP | 3438162 A1 | 2/2019 |
| JP | 2015-083693 A | 4/2015 |
| JP | 2019-519663 A | 7/2019 |
| WO | WO-2013/002387 A1 | 1/2013 |
| WO | 2014/034897 A1 | 3/2014 |
| WO | 2015/129917 A1 | 9/2015 |
| WO | 2016/111223 A1 | 7/2016 |
| WO | 2017/002972 A1 | 1/2017 |
| WO | 2017/170605 A1 | 10/2017 |
| WO | 2019/221235 A1 | 11/2019 |

OTHER PUBLICATIONS

Office Action from Chinese Application No. 202080091807.4 dated Mar. 28, 2024.
Third Party Observation issued in EP Application No. EP20912159.9 dated Jun. 9, 2023.
Office Action from EP Application No. 20912159.9 dated Nov. 26, 2024.
Written Opinion issued in corresponding PCT/JP2020/047821 dated Mar. 16, 2021.
International Search Report issued in PCT/JP2020/047821 dated Mar. 16, 2021.
Extended European Search Report issued in European Application No. 20912159.9 dated Dec. 5, 2023.
Office Action from European Application No. 20912159.9 dated Oct. 15, 2025.

* cited by examiner

Cavity (Hollow that is connected to outside)

Void (Hollow that is not connected to outside)

ABSORBENT BODY, WATER-ABSORBING RESIN, AND ABSORBENT ARTICLE

PRIORITY STATEMENT

This application is a national stage application under 35 U.S.C. § 371 of PCT International Application No. PCT/JP2020/047821, which has an international filing date of 22 Dec. 2020 and claims priority under 35 U.S.C. § 119 to Japanese Patent Application No. 2020-000122 filed on 6 Jan. 2020. The contents of each application recited above are incorporated herein by reference in their entirety.

TECHNICAL FIELD

The present invention relates to an absorbent body that, for example, in a case where the absorbent body has been used in an absorbent article, such as a thin disposable diaper, having an absorbent body with a low proportion of fiber material such as pulp, has an increased amount of liquid trapped under load on second and subsequent urinations over the conventional ones, a water-absorbing resin that is used in the absorbent body and has an increased absorption capacity under load on the second and subsequent urinations over the conventional ones, and an absorbent article including the absorbent body.

BACKGROUND ART

In recent years, there has been an increasing tendency to reduce the thickness of a sanitary material, such as a disposable diaper, for all ages including children and adults and for all applications including light incontinence, and a ratio of a water-absorbing resin in an absorbent body of the sanitary material is ever increasing. Generally, the absorbent body is formed from a composite of a water-absorbing resin and wood-ground pulp. The wood-ground pulp is hydrophilic fibers mainly composed of cellulose. The wood-ground pulp, in an absorbent body of, for example, a disposable diaper, has an effect of quickly taking urine immediately after urination into the absorbent body and diffusing the urine throughout the absorbent body (short-time liquid trapping function). However, a decrease in ratio of a fiber material such as pulp with the recent reduction in thickness, and further, the advent of a disposable diaper that employs a pulp-free absorbent body, have led to a need of a water-absorbing resin to take over the above-described short-time liquid trapping function for which pulp have conventionally been responsible in an absorbent body.

In other words, a next-generation absorbent body used in a sanitary material such as a disposable diaper is required to have an excellent short-time liquid trapping function even in a case where the absorbent body has a low proportion of fiber material such as pulp. Further, as a water-absorbing resin required for the above-described absorbent body having excellent short-time liquid trapping function and having a low proportion of fiber material such as pulp, there is a demand for a water-absorbing resin having a more excellent short-time liquid trapping function than that of the conventional water-absorbing resins.

As described above, in order to obtain an absorbent body having an excellent liquid trapping function in spite of having a low proportion of fiber material such as pulp and a water-absorbing resin having an improved liquid trapping function, improvements focusing on a water absorption speed of a water-absorbing resin have been made so far, and, for example, the water-absorbing resins disclosed in Patent Literatures 1 to 5 below have been proposed.

CITATION LIST

Patent Literatures

Patent Literature 1
WO 2016/111223 A1
Patent Literature 2
WO 2019/221235 A1
Patent Literature 3
EP 3241861 A1
Patent Literature 4
EP 3438162 A1
Patent Literature 5
EP 3260485 A1

SUMMARY OF INVENTION

Technical Problem

However, the water-absorbing resins disclosed in Patent Literatures 1 to 5 have an excellent water absorption speed by themselves, but, for example, in a case where they have been used in an absorbent article, such as a thin disposable diaper, having an absorbent body with a low proportion of fiber material such as pulp, have the problem of causing the absorbent article such as a disposable diaper to have an insufficient liquid trapping function on second and subsequent urinations. Particularly, the water-absorbing resins disclosed in Patent Literatures 1 to 5 have the problem that the absorbent body has an insufficient amount of liquid trapped under load on the second and subsequent urinations, and the water-absorbing resin has an insufficient absorption capacity under load on the second and subsequent urinations.

An object of an aspect of the present invention is to, even in a case where an absorbent body having a low proportion of fiber material such as pulp has been used in an absorbent article such as a thin disposable diaper, enable the absorbent article such as a disposable diaper to have an improved liquid trapping function on second and subsequent urinations over the conventional ones.

Particularly, a main object of an aspect of the present invention is to provide an absorbent body that has an increased amount of liquid trapped under load on the second and subsequent urinations over the conventional ones and a water-absorbing resin that is used in the absorbent body and has an increased absorption capacity under load on the second and subsequent urinations over the conventional ones.

Solution to Problem

The inventors of the present invention diligently studied to solve the above-described problems, and as a result, found that a water-absorbing resin having a gel expansion force under a load of 4.83 kPa of 26 N or more has an increased absorption capacity under load on second and subsequent urinations over the conventional ones. In a case where such a water-absorbing resin was used in an absorbent body having a low proportion of fiber material such as pulp, the absorbent body could have an increased amount of liquid trapped under load on the second and subsequent urinations over the conventional ones. The inventors of the present invention thus found that, even in a case where such an absorbent body has been used in an absorbent article such as a thin disposable diaper, the absorbent article such as a disposable diaper has an improved liquid trapping function on the second and subsequent urinations over the conventional ones, and the inventors of the present invention completed the present invention.

That is, the absorbent body in accordance with an embodiment of the present invention includes a water-absorbing resin having a gel expansion force under a load of 4.83 kPa of 26 N or more.

Advantageous Effects of Invention

According to an aspect of the present invention, it is possible to provide an absorbent body that enables an absorbent article such as a disposable diaper to have an improved liquid trapping function on second and subsequent urinations over the conventional ones and particularly to have an increased amount of liquid trapped under load on the second and subsequent urinations over the conventional ones, in a case where the absorbent body has a low proportion of fiber material (hydrophilic fibers) such as pulp and has been used in an absorbent article such as a thin disposable diaper. Furthermore, according to an aspect of the present invention, it is possible to provide a water-absorbing resin that has an increased absorption capacity under load on the second and subsequent urinations over the conventional ones.

BRIEF DESCRIPTION OF DRAWINGS

FIG. 11 is a view for explaining a method for measuring the amount of liquid trapped under load of an absorbent body in accordance with an embodiment of the present invention.

DESCRIPTION OF EMBODIMENTS

Figure 1:
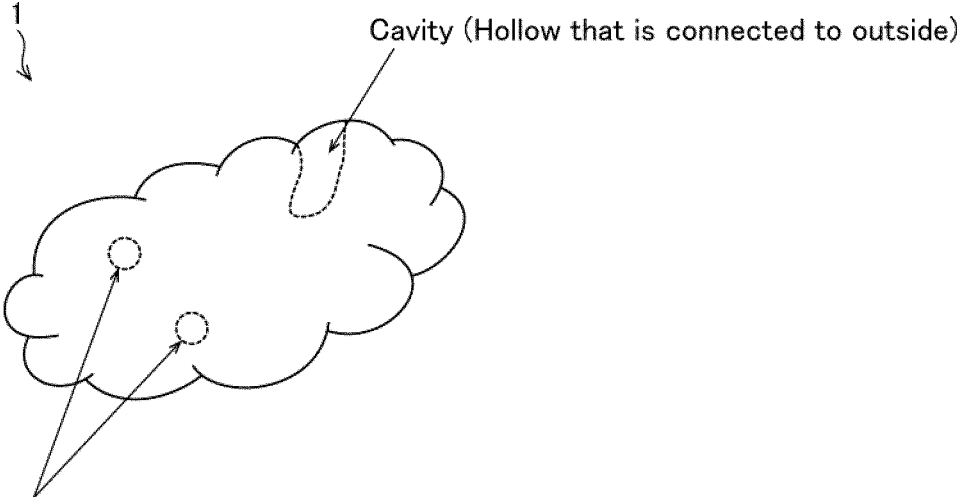
FIG. 1 is a schematic elevational view for explaining hollows (a cavity and a void) formed in a water-absorbing resin in accordance with an embodiment of the present invention.

The following description will discuss an embodiment of the present invention. Note, however, that the present invention is not limited to such an embodiment. The present invention is not limited to the description of the arrangements below, but may be altered in various ways within the scope of the claims. The present invention also encompasses, in its technical scope, any embodiments and examples derived by combining technical means disclosed in differing embodiments and examples. All of the documents cited herein are incorporated herein by reference. In the present specification, any numerical range "A to B" means "not less than A and not more than B".

[1] Definitions of Terms

[1-1] Water-Absorbing Resin

In the present specification, the term "water-absorbing resin" refers to a polymer gelling agent having a water-swelling property and a water-insolubility, and the water-absorbing resin is generally particulate. Further, the term "water-swelling property" refers to an absorption capacity without load (CRC) as defined in WSP 241.3(10) of 5 g/g or more, and the term "water-insolubility" refers to a soluble content (Ext) as defined in WSP 270.3(10) of 50 mass % or less. Note that the term "CRC" is an acronym for centrifuge retention capacity and means an absorption capacity of a water-absorbing resin without load.

The "water-absorbing resin" is preferably a hydrophilic crosslinked polymer that has been obtained by crosslinking and polymerizing unsaturated monomers each of which has a carboxyl group. Note, however, that the water-absorbing resin is not necessarily wholly (that is, 100 mass %) a crosslinked polymer, and can contain an additive and/or the like to the extent that the above-described performance such as CRC and Ext is maintained.

In some cases, the term "water-absorbing resin" may refer to a polymer which is crosslinked only internally (that is, a polymer in which an internal crosslinking density and a surface crosslinking density are substantially the same) or a polymer whose inside and surface are both crosslinked (that is, a polymer in which a surface crosslinking density is higher relative to the internal crosslinking density thereof).

In the present specification, the "polymer which is crosslinked only internally" and the "polymer whose inside and surface are both crosslinked" are not distinguished in principle, and are both expressed as "water-absorbing resin". Note, however, that if these polymers need to be clearly distinguished in terms of whether or not they have been surface-crosslinked, the "polymer which is crosslinked only internally", which is a polymer before being surface-crosslinked, is thus expressed as "water-absorbing resin before surface-crosslinking", and the "polymer whose inside and surface are both crosslinked", which is a polymer after having been surface-crosslinked, is thus expressed as "water-absorbing resin after surface-crosslinking". Note that the phrase "before surface-crosslinking" means "before a surface-crosslinking agent is added" or "before a crosslinking reaction caused by a heating treatment starts even after a surface-crosslinking agent has been added".

Further, the term "water-absorbing resin" may refer to only a resin component and may also refer to a resin containing a component other than the resin, such as an additive.

[1-2] Acrylic Acid (Salt)-Based Monomer and Polyacrylic Acid (Salt)-Based Water-Absorbing Resin In the present specification, the term "acrylic acid (salt)" means acrylic acid and/or a salt thereof, and the term "acrylic acid (salt)-based monomer" means a monomer that contains acrylic acid (salt) in an amount of 50 mol % or more, relative to a total amount of monomer(s) excluding a crosslinking agent.

In the present specification, the term "polyacrylic acid (salt)-based water-absorbing resin" means a polymer a raw material of which is acrylic acid (salt). In other words, the "polyacrylic acid (salt)-based water-absorbing resin" is a polymer that has a structural unit derived from acrylic acid (salt) and that has a graft component as an optional component.

Specifically, the polyacrylic acid (salt)-based water-absorbing resin is a polymer that contains, relative to a part excluding an internal crosslinking agent of monomers contributing to a polymerization reaction, acrylic acid (salt) in the following proportions: preferably 50 mol % or more, more preferably 70 mol % or more, even more preferably 90 mol % or more, preferably 100 mol % or less, and particularly preferably substantially 100 mol %.

[1-3] "EDANA" and "WSP"

The term "EDANA" is an acronym for the European Disposables and Nonwovens Associations. Further, the term "WSP" is an acronym for Worldwide Strategic Partners, which show global standard measurement methods, provided by EDANA, for water-absorbing resin. In the present specification, physical properties of a water-absorbing resin are measured in conformity with the WSP master copy (2010 revised version).

In the present specification, measurement methods for various physical properties of a water-absorbing resin are carried out in accordance with measurement methods in Examples below, unless otherwise mentioned.

[1-4] Others

In the present specification, the term "XX acid (salt)" means "XX acid and/or a salt thereof", and the term "(meth)acrylic" means "acrylic and/or methacrylic".

[2] Method for Producing Water-Absorbing Resin

A water-absorbing resin in accordance with an embodiment of the present invention has a gel expansion force under a load of 4.83 kPa of 26 N or more. The following description will discuss an example of a preferable method for producing the water-absorbing resin.

[2-1] Step of Preparing Aqueous Monomer Solution

This step is a step of preparing an aqueous monomer solution containing a monomer and at least one polymerizable internal crosslinking agent, the monomer containing acrylic acid (salt) as a main component. It is also possible to use a monomer slurry liquid. For convenience, however, the present specification will describe an aqueous monomer solution.

(Monomer)

Examples of the monomer used in the present invention include: anionic unsaturated monomers and salts thereof such as acrylic acid, (anhydrous) maleic acid, itaconic acid, cinnamic acid, vinyl sulfonic acid, allyltoluene sulfonic acid, vinyltoluene sulfonic acid, styrene sulfonic acid, 2-(meth)acrylamide-2-methylpropane sulfonic acid, 2-(meth)acryloyloxy ethane sulfonic acid, 2-(meth)acryloyloxy propane sulfonic acid, and 2-hydroxyethyl(meth)acryloyl phosphate; mercaptan group-containing unsaturated monomers; phenolic hydroxide group-containing unsaturated monomers; amide group-containing unsaturated monomers such as (meth)acrylamide, N-ethyl(meth)acrylamide, and N,N-dimethyl(meth)acrylamide; amino group-containing unsaturated monomers such as N,N-dimethylaminoethyl(meth)acrylate, N,N-dimethylaminopropyl (meth)acrylate, and N,N-dimethylaminopropyl(meth) acrylamide; and other monomers. Examples of the monomer include a water-soluble unsaturated monomer and a hydrophobic unsaturated monomer. Of these monomers, acrylic acid (salt) is preferable. Further, acrylic acid (salt) and other monomer(s) may be used in combination. In this case, the amount of acrylic acid (salt) used is preferably 50 mol % or more, more preferably 70 mol % or more, even more preferably 90 mol % or more, and particularly preferably substantially 100 mol %, relative to a total amount of monomers excluding a crosslinking agent.

(Neutralization with Basic Compound)

In a case where an acrylic acid (salt)-based monomer is to be used in an embodiment of the present invention, it is preferable that acrylic acid be partially neutralized with use of a basic compound. In other words, a water-absorbing resin in which acid groups of polyacrylic acid are partially neutralized is preferable in an embodiment of the present invention.

Examples of the basic compound include a carbonate or bicarbonate of an alkali metal, a hydroxide of an alkali metal, ammonia, and organic amine. Out of such examples, from the viewpoint of water absorption performance of the water-absorbing resin, a strongly basic compound is selected. As such, the basic compound is preferably a hydroxide of an alkali metal such as sodium, potassium, or lithium. The basic compound is more preferably sodium hydroxide. From the viewpoint of handleability, the basic compound is preferably in the form of an aqueous solution. Note that commercially available sodium hydroxide contains a heavy metal such as zinc, lead, and/or iron on the order of ppm (mass standard), and may thus be technically referred to as a "composition". In an embodiment of the present invention, such compositions are encompassed in the scope of "basic compounds".

A timing of the above-described neutralization is not limited. The neutralization can be carried out before, during, or after polymerization. The neutralization may be carried out at a plurality of timings or a plurality of number of times. From the viewpoint of efficiency of producing the water-absorbing resin, continuous type neutralization is preferable.

In a case where acrylic acid (salt) is to be used in an embodiment of the present invention, the neutralization rate of the acrylic acid (salt) is preferably 10 mol % or more, more preferably 40 mol % or more, even more preferably 50 mol % or more, particularly preferably 60 mol % or more, preferably 90 mol % or less, more preferably 85 mol % or less, even more preferably 80 mol % or less, and particularly preferably 75 mol % or less, relative to the acid groups of the monomer. Setting the neutralization rate to be within the above range makes it possible to prevent a decrease in the water absorption performance of the water-absorbing resin. The above neutralization rate is applied to neutralization carried out before the polymerization, neutralization carried out during the polymerization, and neutralization carried out after the polymerization. The above neutralization rate is applied similarly to a water-absorbing resin.

(Internal Crosslinking Agent)

In a preferable production method in an embodiment of the present invention, an internal crosslinking agent is used. Examples of the internal crosslinking agent include N,N'-methylenebis(meth)acrylamide, (poly)ethylene glycol di(meth)acrylate, (poly)propylene glycol di(meth)acrylate, trimethylolpropane di(meth)acrylate, trimethylolpropane tri (meth)acrylate, glycerin tri(meth)acrylate, glycerin acrylate methacrylate, ethyleneoxide modified trimethylol propane tri(meth)acrylate, pentaerythritol tetra(meth)acrylate, dipentaerythritol hexa(meth)acrylate, triallyl cyanurate, triallyl isocyanurate, triallyl phosphate, triallylamine, poly(meth) allyloxy alkane, (poly)ethylene glycol diglycidyl ether, glycerol diglycidyl ether, ethylene glycol, polyethylene glycol, propylene glycol, glycerin, pentaerythritol, ethylenediamine, polyethyleneimine, and glycidyl (meth)acrylate. At least one internal crosslinking agent is selected from among these internal crosslinking agents, with consideration given to reactivity and the like.

In an embodiment of the present invention, from the viewpoint of water absorption performance and the like of the water-absorbing resin, the internal crosslinking agent is preferably an internal crosslinking agent having two or more polymerizable unsaturated groups, and more preferably an internal crosslinking agent having a (poly)alkylene glycol structure and two or more polymerizable unsaturated groups. Specific examples of the polymerizable unsaturated groups include an allyl group and a (meth)acrylate group. Out of these examples, a (meth)acrylate group is preferable. Further, the internal crosslinking agent having a (poly) alkylene glycol structure and two or more polymerizable unsaturated groups includes polyethyleneglycol di(meth) acrylate. Note that the number (hereinafter expressed as "n") of alkylene glycol units is preferably 1 or more, more preferably 2 or more, even more preferably 4 or more, particularly preferably 6 or more, preferably 100 or less, more preferably 50 or less, even more preferably 20 or less, and particularly preferably 10 or less.

The amount of the internal crosslinking agent used is preferably 0.0001 mol % or more, more preferably 0.001 mol % or more, even more preferably 0.01 mol % or more, particularly preferably 0.02 mol % or more, preferably 10 mol % or less, more preferably 5 mol % or less, even more preferably 1 mol % or less, and particularly preferably 0.50 mol % or less, relative to the monomers excluding the internal crosslinking agent. Setting the amount of the internal crosslinking agent used to be within the above ranges makes it possible to obtain a water-absorbing resin having a desired water absorption performance. The amount of the internal crosslinking agent used falling outside the above ranges may cause a reduction in gel strength accompanied by an increase in water-soluble component and a reduction in absorption capacity.

In an embodiment of the present invention, a timing at which the internal crosslinking agent is added only needs to be a timing that allows a polymer to be uniformly crosslinked, and a method of adding the internal crosslinking agent to an aqueous monomer solution before polymerization and to a hydrogel during or after polymerization is taken as an example. Particularly, a method of adding a predetermined amount of internal crosslinking agent to an aqueous monomer solution in advance is preferable.

(Substance(s) Added to Aqueous Monomer Solution)

In an embodiment of the present invention, from the viewpoint of improving physical properties of the water-absorbing resin, any of the below substances can be added to the aqueous monomer solution at at least one of the following times: during preparation of the aqueous monomer solution; during the polymerization reaction; during the crosslinking reaction; after the polymerization reaction; and after the crosslinking reaction.

Specific examples of the substance which can be added include: a hydrophilic polymer such as starch, a starch derivative, cellulose, a cellulose derivative, polyvinyl alcohol (PVA), polyacrylic acid (salt), and crosslinked polyacrylic acid (salt); and a compound such as a carbonate, an azo compound, a foaming agent which generates any of various types of gas bubbles, a surfactant, a chelating agent, and a chain transfer agent.

The amount of the hydrophilic polymer added is preferably 50 mass % or less, more preferably 20 mass % or less, even more preferably 10 mass % or less, particularly preferably 5 mass % or less, preferably 0 mass % or more, and more preferably more than 0 mass %, relative to the aqueous monomer solution. The amount of the compound added is preferably 5 mass % or less, more preferably 1 mass % or less, even more preferably 0.5 mass % or less, preferably 0 mass % or more, and more preferably more than 0 mass %, relative to the aqueous monomer solution.

In a case where a water-soluble resin or a water-absorbing resin is used as the hydrophilic polymer, a graft polymer or a water-absorbing resin composition (for example, a copolymer produced from starch and acrylic acid (salt), or a copolymer produced from PVA and acrylic acid (salt)) can be obtained. These graft polymers and water-absorbing resin compositions are also encompassed in the scope of the polyacrylic acid (salt)-based water-absorbing resin.

(Monomer Component Concentration)

The aqueous monomer solution is prepared by selecting various substances and various components (hereinafter referred to as a "monomer component") as described above in accordance with an objective and then mixing the selected substances and components together in respective amounts defined so as to fall within the above-described ranges. Note that, in an embodiment of the present invention, instead of employing an aqueous monomer solution, it is possible to employ a mixed monomer solution containing water and a hydrophilic solvent.

Further, from the viewpoint of the physical properties of the water-absorbing resin, the concentration of the total of the monomer component is preferably 10 mass % or more, more preferably 20 mass % or more, even more preferably 30 mass % or more, preferably 80 mass % or less, more preferably 75 mass % or less, and even more preferably 70 mass % or less. The concentration of the monomer component is calculated by use of the following Formula (A):

$$\text{Monomer component concentration (mass \%)} = [(\text{mass of monomer component})/(\text{mass of aqueous monomer solution})] \times 100 \qquad \text{Formula (A)}.$$

Note that in Formula (A), the "mass of the aqueous monomer solution" does not include a mass of a graft component, a mass of the water-absorbing resin, or a mass of a hydrophobic organic solvent used in reversed phase suspension polymerization.

[2-2] Polymerization Step

This step is a step of polymerizing an aqueous monomer solution so that a crosslinked hydrogel polymer (hereinafter simply referred to as "hydrogel") is obtained. Preferably, this step is a step of polymerizing the aqueous monomer solution obtained in the step of preparing the aqueous monomer solution so that a hydrogel is obtained, the aqueous monomer solution containing a monomer and at least one polymerizable internal crosslinking agent, the monomer containing acrylic acid (salt) as a main component.

(Polymerization Initiator)

As a polymerization initiator used in an embodiment of the present invention, one (or two or more) of the polymerization initiators used in an ordinary water-absorbing resin production can be selected and used in accordance with, for example, the type of monomer to be polymerized and polymerization conditions. Examples of the polymerization initiator include a pyrolysis-type initiator and a photolytic-type initiator.

Examples of the pyrolysis-type initiator include persulfates such as sodium persulfate, potassium persulfate, and ammonium persulfate; peroxides such as hydrogen peroxide, t-butyl peroxide, and methyl ethyl ketone peroxide; and azo compounds such as an azonitrile compound, an azoamidine compound, a cyclic azoamidine compound, an azoamide compound, an alkylazo compound, 2,2'-azobis(2-amidinopropane) dihydrochloride, and 2,2'-azobis[2-(2-imidazolin-2-yl) propane]dihydrochloride.

Examples of the photolytic-type initiator include benzoin derivatives, benzyl derivatives, acetophenone derivatives, benzophenone derivatives, and azo compounds.

Of these polymerization initiators, persulfates are preferable, in consideration of cost and an ability to reduce a residual monomer. Alternatively, an oxidizing polymerization initiator which is, for example, any of the above-listed persulfates or any of the above-listed peroxides and a reducing agent (for facilitating decomposition of the oxidizing polymerization initiator) can be used in combination to allow the combination to serve as a redox-type initiator. Examples of the reducing agent include a (bi)sulfurous acid (salt) such as sodium sulfite and sodium hydrogen sulfite, a reducing metal (salt) such as L-ascorbic acid (salt) and ferrous salt, and an amine.

The amount of the polymerization initiator used is preferably 0.001 mol % or more, more preferably 0.01 mol % or more, preferably 1 mol % or less, more preferably 0.5 mol % or less, and even more preferably 0.1 mol % or less, relative to the monomers excluding the internal crosslinking agent. Further, the amount of the reducing agent used is preferably 0.0001 mol % or more, more preferably 0.0005 mol % or more, preferably 0.02 mol % or less, and more preferably 0.015 mol % or less, relative to the monomers excluding the internal crosslinking agent. Setting the amounts of polymerization initiator and reducing agent used to be within the above ranges makes it possible to obtain a water-absorbing resin having a desired water absorption performance.

In an embodiment of the present invention, the polymerization reaction may be initiated by irradiation of an active energy ray such as a radiation ray, an electron ray, and/or an ultraviolet ray. It is also possible to combine irradiation of an active energy ray with the above-described polymerization initiator.

(Form of Polymerization)

Examples of forms of polymerization which can be applied to an embodiment of the present invention include aqueous solution polymerization, reversed phase suspension polymerization, spray polymerization, droplet polymerization, bulk polymerization, and precipitation polymerization. Out of these forms, from the viewpoints of ease of controlling polymerization and the water absorption performance of the water-absorbing resin, the form of polymerization is preferably aqueous solution polymerization or reversed phase suspension polymerization, more preferably aqueous solution polymerization, and even more preferably continuous aqueous solution polymerization. Examples of the reversed phase suspension polymerization are disclosed in, for example, International Publication No. WO 2007/004529 and International Publication No. WO 2012/023433. The continuous aqueous solution polymerization makes it possible to produce the water-absorbing resin with high productivity. Examples of the continuous aqueous solution polymerization include: continuous belt polymerization as disclosed in, for example, U.S. Pat. Nos. 4,893,999, 6,906,159, 7,091,253, 7,741,400, 8,519,212, and Japanese Patent Application Publication Tokukai No. 2005-36100; and continuous kneader polymerization as disclosed in, for example, U.S. Pat. No. 6,987,151.

Examples of preferable forms of the continuous aqueous solution polymerization include high-temperature-initiating polymerization, high-concentration polymerization, and foaming polymerization. The "high-temperature-initiating polymerization" means a form of polymerization in which a temperature of the aqueous monomer solution at the initiation of polymerization is preferably 35° C. or more, more preferably 40° C. or more, even more preferably 45° C. or more, particularly preferably 50° C. or more, and preferably a temperature that is equal to or lower than a boiling point of the aqueous monomer solution. Further, the "high-concentration polymerization" means a form of polymerization in which a monomer concentration at the initiation of polymerization is preferably 30 mass % or more, more preferably 35 mass % or more, even more preferably 40 mass % or more, particularly preferably 45 mass % or more, and preferably a concentration that is equal to or lower than a saturation concentration of the aqueous monomer solution. The "foaming polymerization" means a form of polymerization in which the aqueous monomer solution to be polymerized contains a foaming agent or gas bubbles.

One of these forms of polymerization may be employed alone. Alternatively, two or more of these forms of polymerization may be employed in combination.

Examples of a method for dispersing gas bubbles in the foaming polymerization include: a method of dispersing gas bubbles by reducing the solubility of gas dissolved in the aqueous monomer solution; a method of introducing gas from an external source and dispersing the gas as gas bubbles; and a method of causing foaming by adding a foaming agent to the aqueous monomer solution. A combination of any of these methods for dispersing gas bubbles may be employed as appropriate in accordance with desired physical properties of the water-absorbing resin.

With regards to a case where a gas is introduced from the external source, examples of the gas include oxygen, air, nitrogen, carbonic acid gas, ozone, and the like, as well as a mixed gas constituted by a mixture of any of these gases. From the viewpoints of polymerizability and cost, preferably used is an inert gas(es) such as nitrogen and carbonic acid gas, and more preferably used is nitrogen.

Examples of the foaming agent that can be used include an azo compound and a solution of an organic or inorganic carbonate, dispersion liquid thereof, or powder thereof having particle diameter of 0.1 μm to 1000 μm. Out of these examples, the inorganic carbonate is preferable. Specific examples include a carbonate such as sodium carbonate, ammonium carbonate, and magnesium carbonate, and a bicarbonate.

Subjecting a foam-shaped hydrogel obtained by the foaming polymerization to gel-crushing facilitates drying. Further, a foam-shaped water-absorbing resin makes it possible to improve the water absorption speed of the water-absorbing resin and further makes it easy to fix the water-absorbing resin in an absorbent article. Whether or not the water-absorbing resin is a foam-shaped water-absorbing resin can be confirmed by observing the pores (for example, pores having a diameter of 1 μm to 100 μm) of the surface of the water-absorbing resin by use of an electron microscope. The number of pores per water-absorbing resin particle is preferably 1 or more, more preferably 10 or more, preferably 10,000 or less, and more preferably 1,000 or less, and can be controlled by the foaming polymerization.

[2-3] Gel-Crushing Step

This step is a step of crushing a hydrogel during and/or after the polymerization step. Specifically, the hydrogel may be crushed in the polymerization step, and alternatively, the hydrogel may be crushed after the polymerization step. In other words, this step is a step of gel-crushing the hydrogel so that a hydrogel in the form of particles (hereinafter referred to as "particulate hydrogel") is obtained. This step is called "gel-crushing" to distinguish it from the "pulverization" of the later-described pulverizing step. Further, a target for gel-crushing is not only the hydrogel obtained in the polymerization step and may include a recycled granulated gel (described later), unless particularly mentioned otherwise. The same applies to the other steps, unless particularly mentioned otherwise.

The gel-crushing refers to adjusting the size of the hydrogel so as to be a predetermined size, with use of a kneader, a screw extruder such as a meat chopper, or a gel-crusher such as a cutter mill.

In a case where the hydrogel is to be gel-crushed, it is preferable that preferably hot water and/or water vapor be added to a gel crusher. The addition of hot water and/or water vapor is preferably carried out since a resulting particulate hydrogel has low tackiness and good air permeability and is thus easy to dry. The hot water has a temperature of preferably 40° C. or more, more preferably 50° C. or more, even more preferably 60° C. or more, and preferably 100° C. or less.

With regards to, for example, the form of the gel-crushing and the operating conditions employed in the gel-crushing, the disclosures of the pamphlet of International Publication No. 2011/126079 can be preferably applied to an embodiment of the present invention. Note that in a case where the form of polymerization is kneader polymerization, the polymerization step and the gel-crushing step are carried out simultaneously. Undergoing the gel-crushing step in an embodiment of the present invention makes it possible to obtain a water-absorbing resin having a non-uniformly pulverized shape.

Further, a method for producing a water-absorbing resin in accordance with an embodiment of the present invention is more preferably such that a fine powder recycle step includes: a granulation step of mixing removed fine powder and a water-based liquid so that a granulated gel is obtained; and a granulated gel addition step of adding the granulated gel to a hydrogel in at least one step of the steps that are carried out after the end of the gel-crushing step until drying is completed in the drying step and/or in between any steps of the steps that are carried out after the end of the gel-crushing step until drying is completed in the drying step. In addition, in the gel-crushing step in an embodiment of the present invention, it is more preferable that gel-grinding energy be controlled appropriately. With regard to a particulate hydrogel obtained by performing gel-crushing with a predetermined gel-grinding energy described below, a water-absorbing resin obtained afterward is highly evaluated for its physical properties in terms of a water absorption speed (for example, FSR described in International Publication No. WO 2009/016055 and Vortex described in "Testing method for water absorption rate of super absorbent polymers" in JIS K7224 (1996)).

Here, the term "gel-grinding energy" as used in the present invention refers to mechanical energy per unit mass, the mechanical energy being necessary for a gel-crushing device to gel-crush a hydrogel (i.e., mechanical energy per unit mass of a hydrogel). The gel-grinding energy does not include energy with which to heat or cool a jacket, or energy of water or steam to be introduced. Note that "gel-grinding energy" is abbreviated as "GGE".

In a case where the gel-crushing device is driven by a three-phase alternating current power, GGE is calculated based on the following Formula (I).

$$\text{GGE [J/g]} = \{\sqrt{3} \times \text{voltage} \times \text{electric current} \times \text{power factor} \times \text{motor efficiency}\} / \{\text{mass of hydrogel introduced into gel crusher per second}\} \qquad \text{Formula (I)}$$

The "power factor" and the "motor efficiency" are each a value which is unique to the gel-crushing device and changes depending on, for example, an operation condition of the gel-crushing device and which ranges from 0 to 1. These values can be known by, for example, making inquiries to a manufacturer of the device or the like. In a case where the gel-crushing device is driven by a single-phase alternating current power, GGE can be calculated by replacing "I3" with "1" in Formula (I) above. Note that a unit of a voltage is [V], a unit of an electric current is [A], and a unit of mass of a hydrogel is [g/s].

The "power factor" and the "motor efficiency" during gel-crushing are applied to the GGE. Since the electric current value during idling is small, the values of the power factor and the motor efficiency during idling are defined approximately as in Formula (I) above. For example, in a case where a hydrogel is continuously fed by a quantitative feeder, the "mass of hydrogel introduced into gel crusher per second" [g/s] in Formula (I) above refers to a value obtained by conversion into [g/s]. Note, however, that the hydrogel may include a recycled granulated gel as described later.

The gel-grinding energy (GGE) for performing gel-crushing in an embodiment of the present invention is preferably 100 J/g or less, more preferably 80 J/g or less, even more preferably 60 J/g or less, preferably 20 J/g or more, more preferably 25 J/g or more, and even more preferably 30 J/g or more. By controlling the gel-grinding energy within any of the above ranges, it is possible to perform gel-crushing while applying adequate shearing and compressive forces to the hydrogel.

Note that, in a case where the gel-crushing is performed with the use of a plurality of crushers such as using a screw extruder after kneader polymerization or using a plurality of screw extruders, the sum of the energies consumed by the crushers is used as a gel-grinding energy (GGE).

Further, controlling the gel-grinding energy as described above can produce more excellent effect in combination with the addition of hot water having the above temperature. Further, after a normal gel-crushing, gel-crushing based on the gel-grinding energy may be performed.

The particulate hydrogel grain-refined through the gel-crushing step has a particle diameter in a range of preferably 0.1 mm to 10 mm, from the viewpoints of ease of drying and physical properties of a resulting water-absorbing resin. Further, the particulate hydrogel has a mass average particle diameter (D50) of preferably 0.1 mm or more, more preferably 0.15 mm or more, even more preferably 0.20 mm or more, particularly preferably 0.25 mm or more, preferably 5 mm or less, more preferably 2 mm or less, even more preferably 1 mm or less, and particularly preferably 0.80 mm or less. A particulate hydrogel having a mass average particle diameter (D50) falling outside the above ranges may be insufficiently dried. In an embodiment of the present invention, a hydrogel to be subjected to the drying step preferably has a mass average particle diameter falling within any of the above ranges, and more preferably satisfies both the above-described particle diameter and the above-described mass average particle diameter.

As to the particle size of the particulate hydrogel, a logarithmic standard deviation ($\sigma\zeta$) that indicates narrowness of a particle size distribution of the particulate hydrogel is preferably 0.2 or more, preferably 1.5 or less, more preferably 1.3 or less, and even more preferably 1.2 or less. A smaller value of the logarithmic standard deviation ($\sigma\zeta$) of the particle size distribution correlates to a more uniform particle diameter and offers the advantage of enabling uniform drying. However, a logarithmic standard deviation ($\sigma\zeta$) of a particle size distribution which is less than 0.2 requires a special operation such as particle size control during polymerization before the gel-crushing or classification of the particulate hydrogel after gel-crushing. As such, a logarithmic standard deviation ($\sigma\zeta$) of particle size distribution which is less than 0.2 is substantially difficult to employ from the viewpoint of productivity and cost.

Note that, in order to increase the later-described specific surface area of a water-absorbing resin, the gel-crushing method disclosed in the pamphlet of International Publication No. WO 2011/126079 is preferably used. Further, the gel-crushing method may be used in combination with the above-described foaming polymerization.

Further, to perform drying uniformly and efficiently, the particulate hydrogel has a moisture content of preferably 30 mass % or more, more preferably 45 mass % or more, preferably 70 mass % or less, and more preferably 55 mass % or less.

[2-4] Drying Step

This step is a step of drying a gel-crushed hydrogel. Specifically, this step is a step of drying the particulate hydrogel (or, when a granulated gel is added, both the granulated gel and the particulate hydrogel) until a desired solid content is attained, so that a dried polymer is obtained. The solid content, i.e. a value obtained by subtracting a moisture content from 100 mass % of the gel, is preferably 80 mass % or more, more preferably 85 mass % or more, even more preferably 90 mass % or more, particularly preferably 92 mass % or more, preferably 99 mass % or less, even more preferably 98 mass % or less, and particularly preferably 97 mass % or less. Setting the solid content of the dried polymer to fall within any of the above ranges makes it possible to efficiently carry out pulverization, classification, and surface-crosslinking. Note that in the present specification, the phrase "drying is completed" means a state in which the solid content reaches 80 mass %. In this step, the dried polymer is in the form of a block, and the moisture content of the dried polymer can vary depending on which portion in the block of the following portions: an upper portion thereof, a lower portion thereof, a central portion thereof, and an end portion thereof the dried polymer is located in. In this case, dried polymers are obtained appropriately from various positions of the block and crushed if necessary, and after that, moisture contents of the dried polymers are measured and averaged.

In the present specification, a dried polymer with a solid content falling below the predetermined solid content can be referred to as an undried material. There may be a case where a "material to be dried" or a "particulate hydrogel" in the drying step includes both a particulate hydrogel and a granulated gel. Further, the drying step in an embodiment of the present invention is a more effective condition particularly in a case where both the particulate hydrogel and the granulated gel are included in the drying step. Note that, in the other steps as well, there may be a case where a hydrogel and a treated material of the hydrogel include a granulated gel and a treated material of the granulated gel.

Examples of a drying method in the drying step include thermal drying, hot air drying, drying under reduced pressure, fluidized bed drying, infrared drying, microwave drying, drying by azeotropic dehydration with a hydrophobic organic solvent, high humidity drying by use of high temperature water vapor, and stirring drying. These drying methods can be employed in any of the following types: a continuous type and a batch type. However, a continuous type is more preferable from the viewpoint of production efficiency. Of these drying methods, stirring drying and hot air drying are preferable from the viewpoint of drying efficiency. Stirring drying is preferably carried out by use of a stirring dryer such a paddle dryer or a rotatable drum type dryer. Further, hot air drying is preferably carried out by use of a through-flow band-type dryer that carries out hot air drying on a through-flow belt. With use of the through-flow band-type dryer, efficient drying is carried out while preventing, for example, the generation of fine powder due to physical breakage and friction of a dried polymer and a material to be dried of, for example, a particulate hydrogel in the process of being dried.

A drying temperature employed in a case where hot air drying is carried out, i.e. a temperature of hot air, is preferably 120° C. or more, more preferably 130° C. or more, even more preferably 150° C. or more, preferably 250° C. or less, more preferably 230° C. or less, and even more preferably 200° C. or less, in consideration of drying efficiency. Further, a drying time is preferably 10 minutes or more, more preferably 20 minutes or more, even more preferably 30 minutes or more, preferably 2 hours or less, more preferably 1.5 hours or less, and even more preferably 1 hour or less. Setting the drying temperature and the drying time to be within these ranges makes it possible to obtain a water-absorbing resin whose physical properties are within a desired range. Note that other drying conditions can be set as appropriate in accordance with a moisture content of a particulate hydrogel to be dried and a granulated gel to be dried, total mass thereof, and a desired solid content. In the case of band drying, various conditions disclosed in, for example, the pamphlet of International Publication No. WO 2006/100300, the pamphlet of International Publication No. WO 2011/025012, the pamphlet of International Publication No. WO 2011/025013, and the pamphlet of International Publication No. WO 2011/111657 can be applied as necessary.

(Through-Flow Band-Type Dryer)

The dryer used in an embodiment of the present invention can be of any of the following types: a continuous type and a batch type. However, a continuous type through-flow band dryer is more preferable from the viewpoint of production efficiency. In a case where the material to be dried is dried by use of the continuous type through-flow band-type dryer, the material to be dried is continuously fed so as to form a layer (hereinafter referred to as "gel layer") on a band of the band dryer and is hot-air dried. The band of this dryer has a width of preferably 0.5 m or more, more preferably 1 m or more, preferably 10 m or less, and more preferably 5 m or less. The band has a length of preferably 20 m or more, more preferably 40 m or more, preferably 100 m or less, and more preferably 50 m or less.

A speed of travel of the material to be dried on the band may be set as appropriate depending on, for example, the belt width, belt length, production volume, and drying time, but, from the viewpoint of, for example, a load on a belt drive device and durability of the device, is preferably 0.3 m/min or more, more preferably 0.5 m/min or more, even more preferably 0.7 m/min or more, preferably 5 m/min or less, more preferably 2.5 m/min or less, even more preferably 2 m/min or less, and particularly preferably 1.5 m/min or less.

The gel layer of the material to be dried spread over the through-flow band-type dryer has an average thickness of preferably 3 cm or more, more preferably 5 cm or more, even more preferably 8 cm or more, preferably 30 cm or less, more preferably 20 cm or less, and even more preferably 15 cm or less. To attain the above solid content efficiently under the above conditions, it is desirable that the thickness of the gel layer be set to be within any of the above ranges. A gel layer having an excessively large thickness is more likely to cause a remaining undried material and non-uniform dryness. Thus, even though the predetermined drying step is carried out, a high proportion of a dried polymer that does not satisfy the above-described preferable solid content may be obtained.

[2-5] Pulverizing Step and Classification Step

A pulverizing step is a step of pulverizing a polymer obtained after drying, and a classification step is a step of removing fine powder from a pulverized polymer. Specifically, this step is a step of pulverizing the dried polymer obtained through the drying step in the pulverizing step and adjusting the particle size of the pulverized polymer to a particle size within a desired range in the classification step so as to obtain a water-absorbing resin. Undergoing the pulverizing step after drying makes it possible to obtain a water-absorbing resin having a non-uniformly pulverized shape.

Examples of a pulverizer which can be used in the pulverizing step include: a high-speed rotation pulverizer such as a roll mill, a hammer mill, a screw mill, or a pin mill; a vibration mill; a knuckle-type pulverizer; and a cylindrical mixer. Out of these examples, a roll mill is preferable from the viewpoint of efficiency of pulverization. It is also possible to employ a combination of a plurality of these pulverizers.

Examples of methods for adjusting the particle size in the classification step include sieve classification with use of a JIS standard sieve (JIS Z8801-1 (2000)), airflow classification, and the like. Out of these examples, sieve classification is preferable from the viewpoint of classification efficiency. Note that, from the viewpoint of ease of pulverization, the classification step may be additionally carried out before the pulverizing step.

The water-absorbing resin has a particle size distribution such that the mass average particle diameter (D50) is preferably 250 μm or more and 600 μm or less, the proportion of particles having a particle diameter of 300 μm to 600 μm is preferably 50 mass % or more, and the proportion of particles having a particle diameter of less than 150 μm is 5 mass % or less. An upper limit of the mass average particle diameter (D50) is preferably 550 μm or less, more preferably 500 μm or less, and even more preferably 450 μm or less. Further, the proportion of the particles having a particle diameter of 300 μm to 600 μm is more preferably 55 mass % or more, even more preferably 60 mass % or more, and particularly preferably 65 mass % or more. Further, the proportion of the particles having a particle diameter of less than 150 μm is preferably 4 mass % or less, more preferably 3 mass % or less, and even more preferably 2 mass % or less. Further, the proportion of particles having a particle diameter of more than 710 μm is preferably 3 mass % or less, more preferably 2 mass % or less, and even more preferably 1 mass % or less. Further, the logarithmic standard deviation (o) that indicates narrowness of the particle size distribution is preferably 0.20 or more, more preferably 0.25 or more, even more preferably 0.27 or more, preferably 0.50 or less, more preferably 0.40 or less, and even more preferably 0.35 or less. A smaller value of the logarithmic standard deviation (o) of the particle size distribution correlates to a more uniform particle diameter and offers the advantage of less particle segregation. Preferably, the mass average particle diameter (D50) and the proportion of the particles having a particle diameter of less than 150 μm are satisfied. More preferably, the mass average particle diameter (D50), the proportion of the particles having a particle diameter of less than 150 μm, and the proportion of the particles having a particle diameter of more than 710 μm are satisfied. Even more preferably, the mass average particle diameter (D50), the proportion of the particles having a particle diameter of less than 150 μm, the proportion of the particles having a particle diameter of more than 710 μm, and the logarithmic standard deviation are satisfied. The mass average particle diameter (D50), the proportion of the particles having a particle diameter of less than 150 μm, the proportion of the particles having a particle diameter of more than 710 μm, and the logarithmic standard deviation can be combined as appropriate so as to be within the above-described ranges.

The above-described particle size is also applied to a water-absorbing resin obtained after the pulverizing step and the classification step. Therefore, in a case where surface-crosslinking is carried out, it is preferable to subject the water-absorbing resin to surface-crosslinking treatment in the surface-crosslinking step so that the particle size falling within the above-described range which has been adjusted for the water-absorbing resin before surface-crosslinking is maintained, and it is more preferable to carry out particle size adjustment by carrying out a sizing step subsequent to the surface-crosslinking step. Note that it is preferable that a water-absorbing resin which has not passed through a sieve having a mesh size of 710 μm in the classification step be returned to the pulverizing step and pulverized again in the pulverizing step. Further, it is preferable that a water-absorbing resin which has passed through a sieve having a mesh size of 150 μm in the classification step be treated in the later-described fine powder recycle step.

[2-6] Surface-Crosslinking Step

This step is a step of providing, in a surface layer of a water-absorbing resin before surface-crosslinking obtained through the above-described steps, a portion with a higher crosslinking density as necessary. The surface-crosslinking step includes, for example, a mixing step, a heat treatment step, and a cooling step. The surface-crosslinking step involves, for example, radical crosslinking on the surface of the water-absorbing resin before surface-crosslinking, surface polymerization on the surface of the water-absorbing resin before surface-crosslinking, and a crosslinking reaction with a surface-crosslinking agent on the surface of the water-absorbing resin before surface-crosslinking, so as to obtain a surface-crosslinked water-absorbing resin.

[2-6-1] Mixing Step

This step is a step of mixing, in a mixing apparatus, a solution containing a surface-crosslinking agent (hereinafter referred to as a "surface-crosslinking agent solution") with the water-absorbing resin before surface-crosslinking, so that a humidified mixture is obtained.

(Surface-Crosslinking Agent)

In an embodiment of the present invention, a surface-crosslinking agent is used at the time of surface-crosslinking. Examples of the surface-crosslinking agent include the surface-crosslinking agents disclosed in U.S. Pat. No. 7,183,456. At least one surface-crosslinking agent is selected from among these surface-crosslinking agents, with consideration given to reactivity and the like. Furthermore, from the viewpoints of, for example, handleability of the surface-crosslinking agent and water absorption performance of the water-absorbing resin, preferably selected is a surface-crosslinking agent which: has two or more functional groups which react with a carboxyl group; and is an organic compound which forms covalent bonds.

Specific examples of the surface-crosslinking agent include: polyhydric alcohol compounds such as ethylene glycol, diethylene glycol, triethylene glycol, tetraethylene glycol, polyethylene glycol, propylene glycol, dipropylene glycol, polypropylene glycol, 1,3-propanediol, 1,2-butanediol, 1,3-butanediol, 1,4-butanediol, 2,3-butanediol, 1,2-pentanediol, 1,3-pentanediol, 1,4-pentanediol, 1,5-pentanediol, 2,3-pentanediol, 2,4-pentanediol, 1,2-hexanediol, 1,3-hexanediol, 1,4-hexanediol, 1,5-hexanediol, 1,6-hexanediol, 2,3-hexanediol, 2,4-hexanediol, glycerin, polyglycerin, diethanolamine, and triethanolamine; polyhydric amine compounds such as ethylenediamine, diethylenetriamine, triethylenetetramine, tetraethylenepentamine, pentaethylenehexamine, polyallylamine, and polyethylene imine; haloepoxy compounds; a condensate of any of the polyhydric amine compounds and any of the haloepoxy compounds; oxazoline compounds such as 1,2-ethylene bisoxazoline; oxazolidinone compounds; alkylene carbonate compounds such as 1,3-dioxolane-2-one (ethylene carbonate), 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, and 1,3-dioxopane-2-one; polyvalent glycidyl compounds such as ethylene glycol diglycidyl ether, polyethylene diglycidyl ether, propylene glycol diglycidyl ether, polypropylene glycol diglycidyl ether, glycerol polyglycidyl ether, diglycerol polyglycidyl ether, polyglycerol polyglycidyl ether, and glycidol; oxetane compounds; vinyl ether compounds; and cyclic urea compounds.

An amount of the surface-crosslinking agent used or a total amount in a case where more than one surface-crosslinking agent is used is preferably 0.01 parts by mass or more, preferably 10 parts by mass or less, more preferably 5 parts by mass or less, and even more preferably 2 parts by mass or less, relative to 100 parts by mass of the water-absorbing resin before surface-crosslinking. Setting the amount of surface-crosslinking agent used to be within any of the above ranges makes it possible to form an optimal crosslinked structure in the surface layer of the water-absorbing resin before surface-crosslinking and thus makes it possible to obtain a water-absorbing resin with excellent physical properties.

The surface-crosslinking agent is preferably added in the form of an aqueous solution to the water-absorbing resin before surface-crosslinking. In such a case, an amount of water used is preferably 0.1 parts by mass or more, more preferably 0.3 parts by mass or more, even more preferably 0.5 parts by mass or more, preferably 20 parts by mass or less, more preferably 15 parts by mass or less, and even more preferably 10 parts by mass or less, relative to 100 parts by mass of the water-absorbing resin before surface-crosslinking. Setting the amount of water used to be within any of the above ranges improves the handleability of the surface-crosslinking agent solution and makes it possible to uniformly mix the surface-crosslinking agent with the water-absorbing resin before surface-crosslinking.

Alternatively, the surface-crosslinking agent solution may contain, as necessary, a hydrophilic organic solvent in combination with the water. In such a case, an amount of the hydrophilic organic solvent used is preferably 5 parts by mass or less, more preferably 3 parts by mass or less, and even more preferably 1 part by mass or less, relative to 100 parts by mass of the water-absorbing resin before surface-crosslinking. Specific examples of the hydrophilic organic solvent include: lower alcohols such as methyl alcohol; ketones such as acetone; ethers such as dioxane; amides such as N,N-dimethylformamide; sulfoxides such as dimethyl sulfoxide; and polyhydric alcohols such as ethylene glycol. However, the amount of these hydrophilic organic solvents used is preferably limited to a minimum amount.

Further, various additives to be added in "[2-7] Additives and step of adding additives" below can be each added to the surface-crosslinking agent solution in an amount in a range of 5 parts by mass or less. Alternatively, the additives can be added in the mixing step, separately from the surface-crosslinking agent solution.

(Method for Mixing and Conditions of Mixing)

A method for mixing the water-absorbing resin before surface-crosslinking with the surface-crosslinking agent solution can be a method in which a surface-crosslinking agent solution is prepared in advance, and the surface-crosslinking agent solution is mixed with the water-absorbing resin before surface-crosslinking preferably by spraying or dropping the surface-crosslinking agent solution onto the water-absorbing resin before surface-crosslinking, more preferably by spraying the surface-crosslinking agent solution onto the water-absorbing resin before surface-crosslinking.

A mixing apparatus for carrying out the mixing preferably has torque necessary to evenly and reliably mix the water-absorbing resin before surface-crosslinking with the surface-crosslinking agent. The mixing apparatus is preferably a high-speed stirring mixer and more preferably a high-speed stirring continuous mixer. The high-speed stirring mixer has a rotation speed which is preferably 100 rpm or more, more preferably 300 rpm or more, preferably 10000 rpm or less, and more preferably 2000 rpm or less.

The water-absorbing resin before surface-crosslinking supplied in this step has a temperature which is preferably 35° C. or more, preferably 80° C. or less, more preferably 70° C. or less, and even more preferably 60° C. or less, from the viewpoints of mixability with the surface-crosslinking agent solution and aggregability of the humidified mixture. Further, a mixing time is preferably 1 second or more, more preferably 5 seconds or more, preferably 1 hour or less, and more preferably 10 minutes or less.

[2-6-2] Heat Treatment Step

This step is a step of heating the humidified mixture, which has been obtained in the mixing step, so as to cause a crosslinking reaction on a surface of the water-absorbing resin before surface-crosslinking. The heat treatment of the humidified mixture may involve heating the humidified mixture in a still state or heating the humidified mixture in a fluid state with use of motive power such as that of stirring or the like. However, it is preferable to heat the humidified mixture while the humidified mixture is stirred because such a method makes it possible to heat the entirety of the humidified mixture uniformly. From the above viewpoint, examples of a heat treatment apparatus for carrying out the heat treatment include a paddle dryer, a multi-fin processer, and a tower dryer.

A heating temperature in this step is preferably 100° C. or more, more preferably 150° C. or more, even more preferably 170° C. or more, particularly preferably 180° C. or more, preferably 250° C. or less, and more preferably 230° C. or less, from such viewpoints as type and amount of surface-crosslinking agent, and water absorption performance of the water-absorbing resin. A heating time is preferably at least 5 minutes and more preferably at least 7 minutes. Controlling the heating temperature and the heating time to be within the above ranges is preferable because doing so improves the water absorption performance of the water-absorbing resin to be obtained.

[2-6-3] Cooling Step

This step is an optional step which is provided after the heat treatment step if needed. This step involves force-cooling the water-absorbing resin from its high temperature after the heat treatment step to a predetermined temperature and causing the surface-crosslinking reaction to finish quickly.

The cooling of the water-absorbing resin may involve cooling the water-absorbing resin in a still state or cooling the water-absorbing resin in a fluid state with use of motive power such as that of stirring or the like. However, it is preferable to cool the water-absorbing resin while the water-absorbing resin is stirred because such a method makes it possible to cool the entirety of the water-absorbing resin uniformly. From the above viewpoint, examples of a cooling apparatus for carrying out the cooling include a paddle dryer, a multi-fin processer, and a tower dryer. These cooling apparatuses can have similar specifications to the heat treatment apparatus used in the heat treatment step. This is because a heat treatment apparatus can be used as a cooling apparatus by changing a heating medium to a cooling medium.

A cooling temperature in this step may be set as appropriate in accordance with, for example, the heating temperature in the heat treatment step and the water absorption performance of the water-absorbing resin. The cooling temperature is preferably 40° C. or more, more preferably 50° C. or more, preferably 100° C. or less, more preferably 90° C. or less, and even more preferably 70° C. or less.

[2-7] Additive and Step of Adding Additive

In an embodiment of the present invention, it is possible to carry out a step of adding an additive(s) as described below (surface-modifying agent and/or another additive) to the water-absorbing resin as necessary, in addition to the above-described steps.

[2-7-1] Surface-Modifying Agent

A surface-modifying agent is an additive that is added for the purpose of modifying the surface of particles of the water-absorbing resin. Specific examples include a liquid permeability improving agent, an anti-caking agent for a case where moisture has been absorbed, an agent for controlling powder fluidity, and a binder for the water-absorbing resin. Particularly, from the viewpoint of improving liquid permeability, at least one compound selected from the group consisting of a polyvalent metal salt, a cationic polymer, and inorganic fine particles can be used. If necessary, two or more compounds selected from the group can be used in combination. The amount of the surface-modifying agent added is set as appropriate in accordance with the compound (s) selected. For the purpose of modifying the surface of particles of the water-absorbing resin, a step of adding the surface-modifying agent is carried out preferably subsequent to the polymerization step, more preferably subsequent to the drying step, and even more preferably subsequent to the surface-crosslinking step. Further, the surface-modifying agent can be added in one or more steps.

(Polyvalent Metal Salt)

In a case where the polyvalent metal salt is used, a polyvalent metal cation of the polyvalent metal salt has a valence of preferably two or more, more preferably two or more, preferably four or less, and even more preferably three or four. Examples of polyvalent metals which can be used include aluminum and zirconium. As such, examples of polyvalent metal salts which can be used in this step include aluminum lactate, zirconium lactate, aluminum sulfate, and zirconium sulfate. Out of these examples, from the viewpoint of the effect of improving saline flow conductivity (SFC), the polyvalent metal salt is more preferably aluminum lactate or aluminum sulfate and even more preferably aluminum sulfate.

The amount of the polyvalent metal salt added is preferably 0 mol or more, preferably less than $3.6 \times 10^{-5}$ mol, more preferably less than $1.4 \times 10^{-5}$ mol, and even more preferably less than $1.0 \times 10^{-5}$ mol, relative to 1 g of the water-absorbing resin.

Further, a solution containing the polyvalent metal may further contain, as an agent for adjusting permeability of the polyvalent metal into the water-absorbing resin, a monovalent metal compound, such as sodium hydroxide, sodium carbonate, sodium hydrogen carbonate, sodium acetate, and sodium lactate.

(Cationic Polymer)

In a case where the cationic polymer is to be used, examples of the cationic polymer include the substances disclosed in U.S. Pat. No. 7,098,284. Out of these examples, a vinyl amine polymer is more preferable from the viewpoint of improving the liquid permeability. The cationic polymer has a mass average molecular weight of preferably 5000 to 1000000.

The cationic polymer can be added in an amount such that an amount of the cationic polymer is preferably 0 part by mass or more, preferably less than 2.5 parts by mass, more preferably less than 2.0 parts by mass, and even more preferably less than 1.0 part by mass, relative to 100 parts by mass of the water-absorbing resin.

(Inorganic Fine Particles)

In a case where inorganic fine particles are to be used, examples of the inorganic fine particles include the substances disclosed in U.S. Pat. No. 7,638,570. Out of these examples, silicon dioxide is preferable from the viewpoint of improving the liquid permeability. Further, hydrotalcite, calcium phosphate, and aluminum hydroxide are preferable as the inorganic fine particles from the viewpoint of a balance between absorption capacity under load and moisture absorption fluidity.

In a case where the inorganic fine particles have a primary particle diameter of less than 20 nm, the inorganic fine particles can be added in an amount such that an amount of the inorganic fine particles is preferably 0 part by mass or more, preferably less than 1.2 parts by mass, more preferably less than 1.0 part by mass, and even more preferably less than 0.5 parts by mass, relative to 100 parts by mass of the water-absorbing resin.

Further, in a case where the inorganic fine particles have a primary particle diameter of 20 nm or more, the inorganic fine particles can be added in an amount such that an amount of the inorganic fine particles is preferably 0 part by mass or more, preferably less than 2.0 parts by mass, more preferably less than 1.5 parts by mass, and even more preferably less than 1.0 part by mass, relative to 100 parts by mass of the water-absorbing resin.

Adding, to the water-absorbing resin, at least one compound selected from among the polyvalent metal salt, the cationic polymer, and the inorganic fine particles may cause a decrease in absorption capacity under load of the water-absorbing resin. One of the objects of the present invention is, particularly, to enable a water-absorbing resin to have an increased absorption capacity under load on second and subsequent urinations, and from this viewpoint, the amount of the compound added is limited. Assuming that a (g/g) is an absorption capacity under load of a water-absorbing resin to which the compound has not been added, and b (g/g) is an absorption capacity under load of a water-absorbing resin to which the compound has been added, the amount of the compound added is preferably an amount such that a difference "a–b" (g/g) falls within 0.30 g/g, more preferably an amount such that the difference "a–b" (g/g) falls within 0.10 g/g, even more preferably an amount such that the difference "a–b" (g/g) falls within 0.05 g/g, and particularly preferably an amount such that the difference "a–b" (g/g) is 0.00 g/g.

[2-7-2] Another Additive

Examples of another additive include a chelating agent, a reducing agent, a hydroxycarboxylic acid compound, a surfactant, a compound having a phosphorus atom, an oxidizer, an organic powder such as a metal soap, a deodorizing agent, an antibacterial agent, pulp, thermoplastic fibers, and aromatic substances such as terpene-based aromatic compounds and phenol-based aromatic compounds. One of these substances or two or more thereof can be used as the another additive. The another additive is preferably a chelating agent, and more preferably an amino polyvalent carboxylic acid or an amino polyvalent phosphoric acid. Specific examples of the another additive include chelating agents disclosed in, for example, Japanese Patent Application Publication Tokukaihei No. 11-060975, the pamphlet of International Publication No. WO 2007/004529, the pamphlet of International Publication No. WO 2011/126079, the pamphlet of International Publication No. WO 2012/023433, Published Japanese Translation of PCT International Application Tokuhyo No. 2009-509722, Japanese Patent Application Publication Tokukai No. 2005-097519, Japanese Patent Application Publication Tokukai No. 2011-074401, Japanese Patent Application Publication Tokukai No. 2013-076073, Japanese Patent Application Publication Tokukai No. 2013-213083, Japanese Patent Application Publication Tokukaisho No. 59-105448, Japanese Patent Application Publication Tokukaisho No. 60-158861, Japanese Patent Application Publication Tokukaihei No. 11-241030, and Japanese Patent Application Publication Tokukaihei No. 2-41155.

Adding, to the water-absorbing resin, the another additive (preferably the chelating agent) as in the case of the above described polyvalent metal salt, cationic polymer, and inorganic fine particles, may cause a decrease in absorption capacity under load of the water-absorbing resin. Thus, the amount of the another additive added is also limited. Assuming that a (g/g) is an absorption capacity under load of a water-absorbing resin to which the another additive has not been added, and b (g/g) is an absorption capacity under load of a water-absorbing resin to which the another additive has been added, the amount of the another additive added, as in the case of the amount of the compound added, the compound being at least one compound selected from among the polyvalent metal salt, the cationic polymer, and the inorganic fine particles, is preferably an amount such that a difference "a–b" (g/g) falls within 0.30 g/g, more preferably an amount such that the difference "a–b" (g/g) falls within 0.10 g/g, even more preferably an amount such that the difference "a–b" (g/g) falls within 0.05 g/g, and particularly preferably an amount such that the difference "a–b" (g/g) is 0.00 g/g. Specifically, the amount of the another additive added or contained is in a range of preferably 0 part by mass to 1 part by mass relative to the monomers or the water-absorbing resin.

The additive(s) can be added before, after, or during at least one step selected from among the aforementioned steps, i.e. the step of preparing an aqueous monomer solution, the polymerization step, the gel-crushing step, the drying step, the pulverizing step, the classification step, and the surface-crosslinking step. Preferably, the additive(s) is/are added before, after, or during any of the steps subsequent to the polymerization step.

[2-7-3] Step of Adding Additive

In a case where the additive(s) is/are each a liquid or a solution of an aqueous medium such as water, the addition of the additive(s) to the water-absorbing resin is carried out preferably by spraying the liquid or the solution onto the water-absorbing resin and evenly and reliably mixing the water-absorbing resin and the additive(s) by the application of sufficient torque. In a case where the additive(s) is/are each a solid in a powdery state or the like state, the additive(s) may be dry blended with the water-absorbing resin, and a water-based liquid such as water may be used as a binder.

Specific examples of an apparatus for use in the mixing include a stirring mixer, a cylindrical mixer, a double-wall conical mixer, a V-shaped mixer, a ribbon mixer, a screw mixer, a flow and rotary disk mixer, an airflow mixer, a twin-arm kneader, an internal mixer, a pulverizing kneader, a rotating mixer, and a screw extruder. In a case where a stirring mixer is to be used, a rotation speed of the stirring mixer is preferably 5 rpm or more, more preferably 10 rpm or more, preferably 10000 rpm or less, and more preferably 2000 rpm or less.

[2-8] Sizing Step

In an embodiment of the present invention, it is possible to carry out a sizing step as necessary, in addition to the above-described steps. The sizing step is a step of adjusting a water-absorbing resin after surface-crosslinking obtained through the surface-crosslinking step to a particle size within a desired range so as to obtain a water-absorbing resin ready to be shipped as an end product. Note, however, that in a case where the pulverizing step and the classification step are absent before the surface-crosslinking step, the later-described operation carried out after the surface-crosslinking step is assumed to be the pulverizing step and the classification step. As a method for adjusting the particle size in the sizing step, an adjusting method similar to the method employed in the classification step can be employed. Furthermore, if the water-absorbing resin has aggregated in the surface-crosslinking step or the step of adding the surface-modifying agent, crushing, e.g. light pulverization, may be carried out. Further, the particle size distribution after the particle size adjustment can be adjusted as appropriate according to an intended use, and is preferably the same degree of particle size distribution as in the classification step. Therefore, for example, classification with use of a sieve or the like can be carried out so as to satisfy a desired mass average particle diameter (D50), a desired ratio of the mass average particle diameter (D50), a desired logarithmic standard deviation, and the like.

[2-9] Fine Powder Recycle Step

In an embodiment of the present invention, it is possible to carry out a fine powder recycle step as necessary, in addition to the above-described steps. This step (fine powder recycle step) is a step of, before the completion of drying in the drying step, recycling fine powder that has been removed in the classification step. More specifically, this step is a step of recycling the fine powder obtained in the water-absorbing resin production process, for use in the production process, preferably for use in a step before the drying step, so as to produce a water-absorbing resin.

Examples of the step before the drying step include the step of preparing an aqueous monomer solution, the step of gel-crushing a hydrogel, and the step of drying a gel that has been subjected to grain refining.

In a case where the fine powder is to be recycled for use in the step of preparing an aqueous monomer solution, a desired polymerization reaction can be started after a slurry has been formed by adding the fine powder to the aqueous monomer solution. Alternatively, a desired polymerization reaction can be started after the later-described granulated gel, instead of the fine powder, has been added to the aqueous monomer solution.

In a case where the fine powder is to be recycled for use in the step of gel-crushing a hydrogel, the fine powder can be supplied simultaneously with the supply of the hydrogel to a desired gel crusher so that the hydrogel and the fine powder are merged at the discharge.

The fine powder to be recycled is a fine powder removed preferably in the classification step and more preferably in the classification step, the sizing step, and the like step. Note that the water-absorbing resin production process in which the fine powder is recycled for use does not necessarily have to be exactly the same as the water-absorbing resin production process in which the fine powder has been obtained. The fine powder may be recycled for use in another water-absorbing resin production process which differs to an extent that does not impair the gist of the present invention. For example, the fine powder generated in one production line may be recycled for use in an adjacent production line. Alternatively, after the fine powder has been removed in the same production line, the polymerization conditions and the like may be changed before the fine powder is recycled.

[2-9-1] Granulation Step

This step is a step of mixing the removed fine powder and a water-based liquid to obtain a granulated gel. The granulated gel is a gel such that a plurality of individual particles are gathered and aggregated or fused into a large particle form when observed through an optical microscope, and is preferably a gel that is of such strength as not to be damaged by a classification operation or a conveying operation.

(Fine Powder)

Target fine powder in an embodiment of the present invention is all fine powder obtained in the production of the water-absorbing resin, but is preferably fine powder removed in the classification step, and more preferably fine powder removed in the classification step and the sizing step. The fine powder, with the water-based liquid added thereto, is granulated. A mixing ratio (mass ratio) between the fine powder removed in the classification step and the fine powder removed in the sizing step is preferably 99:1 to 50:50, more preferably 98:2 to 60:40, and even more preferably 95:5 to 70:30. The fine powder removed in the sizing step has undergone the surface-crosslinking step or, in some cases, has undergone not only the surface-crosslinking step but also the step of adding a surface-modifying agent which has been described in the above-described "Surface-modifying agent". Thus, the inclusion of such fine powder in a predetermined ratio in the granulation step is advantageous in that it decreases aggregability of the granulated gel. Further, in an embodiment of the present invention, for example, fine powder removed by a bag filter or the like in each step of the production process may be used for granulation. Alternatively, fine powder obtained through the removal in the separate steps and fine powder obtained through the removal in another production process (with use of another production apparatus) may be used in combination. Further, the fine powder may have a composition which is the same as a composition of the hydrogel to be dried together or may have a composition which differs from the composition of the hydrogel to be dried together. However, it is preferable to use fine powder having a composition which is the same as a composition derived from the hydrogel to be dried together.

A size of the fine powder used for granulation is preferably smaller than a size of the end product of the water-absorbing resin. For example, the fine powder has an upper limit of the mass average particle diameter (D50) defined by JIS standard sieve classification of preferably 150 μm or less, and more preferably 106 μm or less. The fine powder has a lower limit of the mass average particle diameter (D50) of preferably 38 μm or more, and more preferably 45 μm or more. Although the fine powder is targeted in this step, even an agglomerate of a size exceeding the size of the end product can be pulverized as appropriate and used as fine powder for granulation. It is desirable that preferably the fine powder contain particles having a particle diameter defined by JIS standard sieve classification of less than 150 μm in an amount such that an amount of the particles is preferably 50 mass % or more, more preferably 70 mass % or more, even more preferably 90 mass % or more, and preferably 100 mass % or less. Further, from the aspect of granulation strength, the shape of the fine powder is preferably a non-uniform shape obtained by aqueous solution polymerization rather than a spherical shape obtained by reversed phase suspension polymerization. Further, as described above, the fine powder may be fine powder removed after the surface-crosslinking step, which is generally carried out in the production of a water-absorbing resin, may be fine powder removed before the surface-crosslinking step, or may be a mixture thereof.

A water-based liquid is added to the fine powder, preferably a mixture in which the fine powder is mixed in a predetermined ratio, so that a granulated gel is obtained. The granulated gel uses fine powder having various particle diameters obtained from the above-described single step or a plurality of steps.

A temperature of the fine powder when mixed with the water-based liquid is preferably 40° C. or more, more preferably 50° C. or more, even more preferably 60° C. or more, preferably 120° C. or less, more preferably 100° C. or less, and even more preferably 90° C. or less. Increasing the temperature of the fine powder improves mixability of the fine powder and the water-based liquid and makes it easy to obtain a desired granulated gel. However, setting the temperature of the fine powder to be excessively high increases a heating cost. The temperature of the fine powder can be adjusted as appropriate, if necessary, by heating the fine powder from the outside with hot air or the like, by keeping warm the fine powder after heated in the drying step, or by cooling the fine powder through, for example, blowing of a room-temperature air. Preferably, the fine powder is heated or kept warm in a vessel that has a heating means such as a steam trace.

(Water-Based Liquid)

Specific examples of the water-based liquid used for mixing with fine powder include an aqueous solution and the like containing water; lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane and tetrahydrofuran; amides such as N,N-dimethylformamide; sulfoxides such as dimethyl sulfoxide; and the like. From the aspect of physical properties and granulation strength, the water-based liquid has a water content of preferably 90 mass % or more, more preferably 99 mass % or more, and preferably 100 mass % or less. Particularly preferably, the water-based liquid is composed of water only. In addition, the water-based liquid can further contain a small amount of additive, such as a cross-linking agent, a chelating agent, a surfactant, a polymerization initiator, an oxidizer, a reducing agent, and a hydrophilic polymer, to such an extent that the effects of an embodiment of the present invention are not impaired. As the additive, one kind of additive or two or more kinds of additives may be added. In a case where two or more kinds of additives are added, they may be different from each other or may be the same. For example, using a water-based liquid in which the polymerization initiator and/or the reducing agent described in the polymerization step is/are added makes it possible to reduce residual monomers of a granulated gel and a hydrogel. A preferable polymerization initiator is persulfate, and a preferable reducing agent is (bi)sulfurous acid (salt). For example, using a water-based liquid in which an oxidizer is added can, in some cases, reduce deterioration of physical properties, such as absorption capacity, when the granulated gel has been dried. The oxidizer is preferably at least one oxidizer selected from chlorite, hypochlorite, and peroxide, and more preferably hydrogen peroxide. For example, using a water-based liquid in which a surfactant is added makes it possible to cause the surfactant to be contained in the granulated gel and makes it possible to effectively prevent the agglomeration of granulated gels. The surfactant is exemplified by anionic surfactants, nonionic surfactants, cationic surfactants, and amphoteric surfactants. Further, using a water-based liquid in which a crosslinking agent and/or a hydrophilic polymer is/are added makes it possible to increase agglomeration strength of the granulated gel and prevent remicronization in a subsequent step. The crosslinking agent is selected from the above-described internal crosslinking agent and surface-crosslinking agent, and the hydrophilic polymer is selected from the above-described hydrophilic polymer added to the aqueous monomer solution.

Note that, in a case where the fine powder contains the above-described additive such as a crosslinking agent, a chelating agent, a surfactant, a polymerization initiator, an oxidizer, and a reducing agent, it is not necessary to add the additive to the water-based liquid, or alternatively, only an additive shortage may be added to the water-based liquid. It is particularly preferable that the fine powder contain a chelating agent, a surfactant, an oxidizer, a reducing agent, and the like described in the Step of adding additive section.

In a case where the granulation is carried out by mixing the fine powder and the water-based liquid, a preheated water-based liquid is preferably used. Using a heated water-based liquid allows the fine powder to be uniformly granulated in a short time and improves productivity. A temperature of the water-based liquid is preferably 40° C. or more, more preferably 50° C. or more, even more preferably 60° C. or more, particularly preferably 70° C. or more, preferably a temperature that is equal to or lower than a boiling point of the water-based liquid, and more preferably 100° C. or less. Note that the boiling point of the water-based liquid can be adjusted, for example, by addition of a salt and/or a solvent and/or by use of a pressure such as pressurization or depressurization. As an alternative method, a water vapor and a water-based liquid at room temperature may be added at the same time so that the water-based liquid is brought substantially to any of the above temperatures.

The amount of water-based liquid added is preferably less than 100 parts by mass, more preferably 80 parts by mass or less, even more preferably 50 parts by mass or less, preferably 10 parts by mass or more, more preferably 15 parts by mass or more, and even more preferably 20 parts by mass or more, relative to 100 parts by mass of the fine powder (on an as-is basis). The amount of water-based liquid added of 100 parts by mass or more increases a drying load. The amount of water-based liquid added of less than 10 parts by mass may lead to an insufficient granulation strength and may make a granulated material more susceptible to damage due to non-uniform mixing of the fine powder.

(Mixing Apparatus)

In the present invention, in any of the above embodiments, a mixing apparatus used for mixing the water-based liquid and the fine powder is not particularly limited. For example, in the case of a container-fixed type mixer, a mechanical stirring type mixer is preferable. Specifically, the mechanical stirring type mixer is exemplified by a Turbulizer (manufactured by Hosokawa Micron Corporation), a Loedige mixer (manufactured by Gebruder Loedige Maschinenbau GmbH), and a mortar mixer (manufactured by Nishinihonshikenki). Further, either one of a batch type mixer and a continuous type mixer may be used for mixing.

In an embodiment of the present invention, preferably, a heated water-based liquid and heated fine powder are mixed by the mixing apparatus. In an embodiment of the present invention, in addition to the heating of the water-based liquid and the fine powder, it is more preferable that the inside of the mixing apparatus, specifically, a wall surface of the mixing apparatus and/or a stirring means such as a stirring blade, be heated. When the mixing was carried out in a state in which the inside of the mixing apparatus, the water-based liquid, and the fine powder are all heated to a predetermined temperature in this way, it is possible to easily obtain a granulated gel having a desired particle diameter more efficiently. In an embodiment of the present invention, such an effect can be obtained even if any of the fine powder, the water-based liquid, and the mixing apparatus is not heated. However, with preferably at least one of them, more preferably two of them, and even more preferably all of them being heated to a predetermined temperature, a more excellent effect is brought about.

A heating temperature of the inside of the mixing apparatus, preferably an inner wall surface of the mixing apparatus and/or the stirring means, during the mixing is preferably 50° C. or more, more preferably 55° C. or more, still more preferably 60° C. or more, particularly preferably 65° C. or more, most preferably 70° C. or more, preferably 120° C. or less, more preferably 100° C. or less, and still more preferably 90° C. or less. Heating the mixing apparatus, preferably any of the inner wall surface and the stirring means, more preferably both the inner wall surface and the stirring means, allows the fine powder to be uniformly granulated in a short time and improves productivity. The temperature of the inside of the mixing apparatus can be adjusted as appropriate, for example, by supply of a heated gas and/or by conduction of heat.

In an embodiment of the present invention, mixing of the fine powder and the water-based liquid for the granulation is preferably high-speed mixing. Carrying out high-speed mixing prevents generation of a huge gel-like material. This eliminates the need for a huge amount of mixing force that is needed in a case where a huge gel-like material is generated, and makes it possible to circumvent a problem that a gel-like mass in a kneaded state causes, for example, breakage and entanglement of a main chain and results in deterioration of a water-absorbing resin.

The above-described high-speed mixing means that a time from a point in time when contact between the fine powder and the water-based liquid, which are raw materials, occurs in the mixing apparatus to the generation of a granulated gel is short. In other words, the high-speed mixing means that a time from when the raw materials are introduced into the mixing apparatus to when the granulated gel is taken out is short. A mixing time is preferably 3 minutes or less, more preferably 1 minute or less, preferably 1 second or more, and more preferably 5 seconds or more. A long mixing time makes it difficult to uniformly mix the water-based liquid and the fine powder and tends to generate a huge gel-like material into which the water-based liquid and the fine powder are integrated. Further, a long mixing time may lead to performance deterioration of a resulting water-absorbing resin, such as an increase in water-soluble component of the water-absorbing resin and a decrease in absorption capacity under load of the water-absorbing resin.

Therefore, as a means for achieving the high-speed mixing, it is desirable to introduce the raw materials into the mixing apparatus in a short time. The longer a time of the introduction of one or both of the raw materials by, for example, gradual addition carried out by a method such as spraying of the water-based liquid or dropping thereof, the longer the mixing time will become. This may cause the fine powder to become a large agglomerate or may deteriorate a water-absorbing resin due to prolonged kneading. The fine powder and the water-based liquid may be introduced into the mixing apparatus at the same time or at different timings that are timings such that one of the fine powder and the water-based liquid is introduced, and the other one thereof is then introduced. Therefore, a time from the start of the introduction of both of the raw materials when the raw materials are introduced at the same time or the material to be introduced later when the raw materials are introduced at different timings to the end of the introduction, is preferably 60 seconds or less, more preferably 30 seconds or less, and still more preferably 10 seconds or less.

To achieve higher speed mixing, a high-speed stirring paddle mixer is preferably used. At this time, a rotation speed of a paddle is preferably 100 rpm or more, more preferably 200 rpm or more, even more preferably 300 rpm or more, preferably 5000 rpm or less, more preferably 4000 rpm or less, and even more preferably 3000 rpm or less. A direction of a rotation shaft of the paddle is not limited, but is preferably a vertical direction because of the ease of discharge of a granulated gel. Further, the paddle can have any number of rotation shafts, but has preferably one shaft or two shafts and more preferably one shaft, because of the ease of maintenance.

In an embodiment of the present invention, in order to prevent adhesion, the inner wall of the mixer preferably uses a material having a water contact angle of 90 degrees or more. A preferable material is a fluorine resin such as Teflon (registered trademark). However, it is not necessary to use the above-described material for the whole inner wall, and in order to obtain a strong stirring force, a material having a water contact angle of less than 90 degrees may be intentionally used for the inner wall near a paddle. A preferable material is stainless steel from the viewpoint of durability.

(Conveying Step)

It is preferable that the individual steps for producing a water-absorbing resin be linked. Although all the linkages between the individual steps do not necessarily require a conveying step, for example, a step of conveying a granulated gel obtained in the granulation step to a predetermined addition position when the granulated gel is to be recycled can be included.

The conveyance of the granulated gel is carried out in a continuous manner or in a batch manner, and is preferably carried out in a continuous manner. Examples of a conveying machine used in the conveying step include a bucket conveyor, a belt conveyor, a screw conveyor, a chain conveyor, a vibration conveyor, and a pneumatic conveyor, and a bucket conveyor is preferable. Further, it is preferable that, by bringing the granulated gel to be conveyed into a state of being heated and/or kept warm from outside the conveying machine, the granulated gel be maintained at the above-described high temperature even in the process of being conveyed. Such heating and/or keeping warm can be achieved by providing a means for heating an inner wall surface of the conveying machine from outside and/or a means for keeping warm the inner wall surface of the conveying machine from outside. A decrease in temperature of the granulated gel during the conveyance causes the granulated gel to stick to another granulated gel and become an agglomerate before mixed with the hydrogel. The decrease in temperature of the granulated gel also causes the granulated gel to become hard. These become causes of uneven drying in the drying step and tend to generate an undried material. Therefore, in a case where the granulated gel is to be conveyed, the temperature of the produced granulated gel is preferably maintained. More preferably, the produced granulated gel is heated to and/or kept warm at the same temperature as the temperature of the hydrogel to be mixed.

In a case where the conveying step is absent, it is preferable to drop the granulated gel by gravity from the mixing apparatus for the fine powder and the water-based liquid to a position at which the granulated gel is to be mixed with the hydrogel. In such a case, a distance from the mixing apparatus to the position at which the granulated gel is to be mixed with the hydrogel is preferably within 10 m, more preferably within 5 m, and even more preferably within 3 m. Further, it is preferable that a pipe through which the granulated gel passes be heated and/or kept warm for the same reason as in the case of the conveying machine.

If the granulated gel remains for a long time in the apparatus or pipe heated and/or kept warm, the surface of the granulated gel may become dry and hard. Therefore, it is preferable that the granulated gel obtained in the granulation step be mixed with the hydrogel in a state in which the granulated gel is heated to a predetermined temperature as quickly as possible. Specifically, a time from when mixing of the fine powder and the water-based liquid is started in the granulation step to when the obtained granulated gel is added to the hydrogel in the re-addition step is preferably within 5 minutes, more preferably within 3 minutes, and even more preferably within 1 minute. Note that, even in a case where the mixing with the hydrogel cannot be carried out within the above-described time, reheating the granulated gel having a decreased temperature to bring the granulated gel into a state of being heated to a predetermined temperature makes it possible to lower the aggregability of the granulated gel and further soften the granulated gel. Therefore, even in a case where the granulated gel having a decreased temperature is reheated and then mixed with the hydrogel, a good mixed state is obtained as in the case where the mixing is carried out within the above-described predetermined time.

In order to solve the above-described problem that the surface of the granulated gel becomes dry, an atmospheric dew point of the granulated gel during a time between the granulation step and the re-addition step, i.e. in the conveying step carried out before the granulated gel after the granulation is added to the hydrogel, is preferably 50° C. or more, more preferably 55° C. or more, even more preferably 60° C. or more, preferably 99° C. or less, more preferably 95° C. or less, and even more preferably 90° C. or less. Further, in the present invention, it is also a preferable embodiment that atmospheric dew points in the granulation step and/or the re-addition step in addition to the conveying step be controlled to be within any of the above ranges. Specifically, an atmosphere in the apparatus when the fine powder and the water-based liquid are mixed in the granulation step and an atmosphere in the apparatus when the granulated gel is added to the hydrogel are preferably controlled to be within any of the above ranges. The "atmospheric dew point" refers to a dew point of air existing in an atmosphere. The atmospheric dew point can be adjusted to be within any of the above ranges by, for example, blowing water vapor or controlling a circulation rate of hot air.

[2-9-2] Granulated Gel Addition Step

This step is a step of adding a granulated gel to a hydrogel in at least one step of the steps, from the polymerization step to the drying step, carried out until drying is completed in the drying step and/or in between any steps of the steps, from the polymerization step to the drying step, carried out until drying is completed in the drying step. Specifically, it is preferable that the granulated gel be added to the hydrogel in at least one step selected from the group consisting of during the polymerization step, a step carried out after the polymerization step but before the gel-crushing step, during the gel-crushing step, a step carried out after the gel-crushing step but before the drying step, and during the drying step. Note that, since the hydrogel is obtained even during the polymerization step, the granulated gel may be added during the polymerization step. Further, in the gel-crushing step, the granulated gel may be added to the hydrogel and then supplied to the gel crusher. In the drying step, a polymer having a solid content of less than 80 mass % can generally be regarded as a hydrogel. That is, since the hydrogel exists until some midpoint in the drying step, the granulated gel may be added during the drying step. The granulated gel is added to the hydrogel preferably after the gel-crushing step but before the drying step or during the drying step and more preferably after the gel-crushing step but before the drying step. Thus, the addition of the granulated gel to the hydrogel after the crushing allows the granulated gel and the hydrogel to be easily mixed due to a small difference in particle size between the granulated gel and the hydrogel and is less likely to cause non-uniform dryness. Particularly, carrying out crushing at controlled gel-grinding energy allows the hydrogel to have a granulation shape and thus makes it possible to further prevent non-uniform dryness. Note that "before . . . step" and "after . . . step" include all steps before a step concerned and after the step concerned. That is, the phrase "include all steps before a step concerned and after the step concerned" means that the granulated gel may be added in any step such as a conveying step carried out between one step and another step and a storage step. For example, "after the gel-crushing step" includes a time during conveyance to a next step after the gel-crushing step and the next step.

In the granulated gel addition step, the granulated gel has a solid content of 50 mass % or more and 90 mass % or less. An explanation of the solid content of the granulated gel will be provided later.

(Temperature)

In an embodiment of the present invention, the granulated gel is added to the hydrogel. The temperature of the granulated gel and the temperature of the hydrogel at that time are each in a range of 50° C. or more and 100° C. or less, preferably 55° C. or more, more preferably 60° C. or more, preferably 95° C. or less, and more preferably 90° C. or less. The temperatures of the granulated gel and the hydrogel falling within any of these temperature ranges achieve good mixed states of both of the gels. The temperature of the granulated gel or the hydrogel falling below 50° C. can cause the granulated gel to become hard as described earlier or can form an agglomerate when the hydrogel and granulated gel are mixed. That is, when an agglomerate is formed at the mixing, the hydrogel and the granulated gel further stick together to form a huger agglomerate. This results in a poor mixed state. Further, even when the mixing is successfully carried out, the presence of an agglomerate at the drying tends to cause poor dryness, that is, generation of an undried material. Further, continuously carrying out heating to dry the agglomerate until a desired moisture content is achieved brings other granulated gel and hydrogel which have been already dried into an excessively dried state. This leads to deterioration of the quality of a water-absorbing resin, such as an increase in soluble component due to heat deterioration. Such a problem also occurs in a case where the temperature of one of the gels is 50° C. or more, and the temperature of the other gel is less than 50° C. Conversely, the temperature of the granulated gel or the hydrogel more than 100° C. can cause the gels to become harder since the surfaces of the gels become dry.

Further, in an embodiment of the present invention, a smaller difference between the temperature of the granulated gel and the temperature of the hydrogel in the above-described temperature range is preferable, from the viewpoint of decreasing non-uniform dryness. The temperature difference between the granulated gel and the hydrogel is preferably within 40° C., more preferably within 30° C., and even more preferably within 20° C. The temperature of the granulated gel and the temperature of the hydrogel can be adjusted as appropriate by heating and keeping warm the granulated gel and the hydrogel in the production process, by heating the granulated gel and the hydrogel with hot air or the like from outside, by letting the granulated gel and the hydrogel stand to cool, or by cooling the granulated gel and the hydrogel with a low-temperature air or the like.

[2-9-3] Gel-Mixing Step (Mechanical Mixing)

In an embodiment of the present invention, by controlling the temperatures of the granulated gel and hydrogel to be within any of the above-described ranges, the hydrogel and the granulated gel are disintegrated and slightly mixed by slight impact, their own weight, or the like when the granulated gel is added to the hydrogel. In the present invention, an embodiment in which the hydrogel and the added granulated gel are further mechanically mixed in at least one step of the steps, from the granulated gel addition step to the drying step, carried out until drying is completed and/or in between any steps of the steps, from the granulated gel addition step to the drying step, carried out until drying is completed is also a preferable embodiment. In an embodiment of the present invention, as described above, the granulated gel is added to the hydrogel before the drying step is completed. However, regardless of a stage at which the granulated gel is added to the hydrogel, the granulated gel and the hydrogel are dried in a mixed state. Then, if the granulated gel and the hydrogel are in a state of being uniformly present, it is possible to further prevent the generation of an undried material. Note here that "being uniformly present" refers to a mixed state in which the granulated gel and the hydrogel are stirred or a state in which both of the gels are uniformly dispersed such that the proportion per unit area is substantially the same. Note that, in order to exert the effect of the present invention, a period of time from the addition of the granulated gel to the hydrogel to the start of the mechanical mixing is preferably within 5 minutes, more preferably within 2 minutes, and even more preferably within 1 minute. Further, a period of time from the granulation step to the start of the mechanical mixing is preferably within 10 minutes, more preferably within 5 minutes, and even more preferably within 2 minutes. Even at the point in time when the mechanical mixing is started, the temperature of the hydrogel to which the granulated gel has been added is in a range of 50° C. or more and 100° C. or less, preferably 55° C. or more, more preferably 60° C. or more, preferably 95° C. or less, and more preferably 90° C. or less.

In an embodiment of the present invention, in order to bring the granulated gel and the hydrogel into a state of being mixed as uniformly as possible, the granulated gel and/or the hydrogel are mechanically mixed. For the mechanical mixing, any apparatus capable of achieving any of the above-described coexistence states can be used. Examples of a stirring method include rotation stirring by, for example, rotation of a stirring blade or a container itself and stirring by, for example, a feeder that moves like a pendulum.

An apparatus that carries out the stirring method is exemplified by a rotating stirring apparatus, a swing belt type feeder, and a pendulum type conveyor.

In a case where the mechanical mixing is carried out during the polymerization step, the rotating stirring apparatus is preferably a kneader polymerization apparatus. In a case where the mechanical mixing is carried out during the gel-crushing step, the rotating stirring apparatus is preferably, for example, a kneader or a meat chopper.

In a case where the mechanical mixing is carried out after the gel-crushing step but before the drying step, during the drying step, or before drying is completed in the drying step, the swing belt type feeder or the rotating stirring apparatus is preferable. That is, it is preferable that the granulated gel and the hydrogel be supplied to and mixed in the swing belt type feeder or the rotation stirring apparatus. Specifically, by carrying out the mechanical mixing with use of the swing belt type feeder or the rotating stirring apparatus after the gel-crushing step but before the drying step or by carrying out the mechanical mixing with use of the rotating stirring apparatus in the drying step, it is possible to carry out drying in a more homogeneous state. This makes it possible to prevent non-uniform dryness and generation of an undried material.

In the case of using the swing belt type feeder, addition of the granulated gel to the hydrogel being conveyed on a transport belt with use of the swing feeder achieves uniform dispersion of the granulated gel. Alternatively, the hydrogel may be added to the granulated gel being conveyed on the transport belt with use of the swing feeder, or the granulated gel and the hydrogel may be supplied to the swing feeder so that both of the gels are supplied onto the transport belt by the swing feeder. The swing belt type feeder has a belt end that reciprocates on the transport belt. Thus, even when there is an imbalance in distribution of the granulated gel and the hydrogel on the swing belt type feeder, both of the gels are eventually distributed substantially uniformly on the transport belt.

Although a swing angle θ, a belt speed, and the like of the swing feeder can be optionally selected in consideration of a speed of the transport belt, a supply amount, and the like, the travel of the transport belt while making one reciprocating motion is preferably within 1 m, and more preferably within 0.5 m. An excessively long traveling distance of the transport belt while making one reciprocating motion leads to a significant imbalance in the distribution of the granulated gel. Note that the transport belt is preferably a through-flow band-type dryer.

Examples of the rotating stirring apparatus include a type in which the rotation shaft is in a horizontal direction and the container itself rotates, a type in which the rotation shaft is in a horizontal direction and the container itself is fixed, and a type in which the rotation shaft is in a vertical direction and the container itself is fixed. These rotating stirring apparatuses may be either a continuous type or a batch type. Also, mixing may be performed while the hydrogel stacked in the dryer is leveled off with use of a rotary type leveling machine that is used in the drying step. Further, it is also preferable that mixing be performed while drying is carried out with use of the stirring dryer used in the drying step. The rotation speed or the like of the apparatus is not particularly limited, but is preferably 50 rpm or more, more preferably 100 rpm or more, preferably 500 rpm or less, and more preferably 300 rpm or less. Further, a mixing (residence) time in the stirring apparatus is preferably within 180 seconds, more preferably within 60 seconds, even more preferably within 30 seconds, preferably 0.1 seconds or more, and more preferably 1 second or more.

(Solid Content)

In an embodiment of the present invention, it is further preferable that, in the above-described conditions in the re-addition step (step of adding the granulated gel after the granulation to the hydrogel), the solid content of the granulated gel and the solid content of the hydrogel be controlled appropriately. That is, if the solid content of the granulated gel and the solid content of the hydrogel are too low (in other words, if the moisture content relative to 100% of the gel is too high), dryness becomes partially incomplete, and agglomerates are more likely to be generated. In an embodiment of the present invention, it is desirable that the solid content of the granulated gel and/or the solid content of the hydrogel be within an appropriate range(s). The solid content of the hydrogel is preferably 30 mass % or more, more preferably 45 mass % or more, preferably 70 mass % or less, more preferably 55 mass % or less, and even more preferably 50 mass % or less. The solid content of the granulated gel is preferably 50 mass % or more, more preferably 55 mass % or more, even more preferably 60 mass % or more, preferably 90 mass % or less, more preferably 85 mass % or less, and even more preferably 80 mass % or less. A preferable condition is a condition such that, while the temperatures of the granulated gel and the hydrogel are within any of the above-described ranges, the solid contents of these gels are within any of the above-described ranges. Another preferable condition is a condition such that, while the solid content of the granulated gel in the re-addition step is within any of the above-described ranges, the gel-grinding energy in the gel-crushing step is within any of the above-described ranges.

Further, in an embodiment of the present invention, in consideration of achieving more uniform dryness, it is preferable that the solid content of the granulated gel be higher than the solid content of the hydrogel, preferably in a case where the solid content of one of the gels is satisfied, more preferably in a case where the solid contents of both of the gels are satisfied. A higher solid content of the granulated gel than the solid content of the hydrogel enables a reduction in drying load. Specifically, a difference (A−B) between the solid content (A (%)) of the granulated gel and the solid content (B (%)) of the hydrogel is preferably 6 or more, more preferably 11 or more, even more preferably 16 or more, preferably 60 or less, more preferably 50 or less, and even more preferably 40 or less. Setting the difference in the solid content between the granulated gel and the hydrogel to be within any of the above-described ranges leads to a small drying load and further prevents non-uniform dryness, thus avoiding any trouble in the production and any quality problem.

In an embodiment of the present invention, a ratio between the granulated gel and the hydrogel may be determined as appropriate in accordance with the amount of fine powder separated and the setting of the solid content of the granulated gel. From the viewpoint of physical properties of a water-absorbing resin, the granulated gel is added in an amount such that an amount of the granulated gel is normally 10 parts by mass or more, preferably 15 parts by mass or more, more preferably 20 parts by mass or more, preferably 50 parts by mass or less, more preferably 40 parts by mass or less, and even more preferably 30 parts by mass or less, relative to 100 parts by mass of the hydrogel (on an as-is basis). The ratio between the granulated gel and the hydrogel within any of the above-described ranges increases a gel expansion speed. According to a method of an embodiment of the present invention, it is possible to prevent non-uniform dryness even when the proportion of the granulated gel is 10 parts by mass or more. Note that, if the proportion of the granulated gel is too high, final quality and physical properties of a water-absorbing resin as an end product are significantly affected by the recycled fine powder, that is, the granulated gel.

The hydrogel to which the granulated gel is added is treated in the drying step. Since the drying condition and the like of a mixed gel are the same as those of the above-described drying step, the description thereof will be omitted. Further, a pulverizing step and a classification step carried out after the drying step are the same as the above-described pulverizing step and the above-described classification step, and the surface-crosslinking step, the sizing step, and the like are performed as necessary, so that a water-absorbing resin to be a product is obtained. Further, the fine powder obtained in the classification step and other step(s) may also be treated in the above-described recycle step.

[2-10] Other Steps

In an embodiment of the present invention, it is possible to further include, as necessary, at least one step selected from, for example, a conveying step, a storing step, a packaging step, and a reserving step, in addition to the steps described above.

[3] Water-Absorbing Resin

The water-absorbing resin in accordance with an embodiment of the present invention is obtained by carrying out the above-described various steps. That is, a water-absorbing resin having a great gel expansion force under load and a high gel expansion speed under load is obtained.

The gel expansion force under a load of 4.83 kPa of the water-absorbing resin in accordance with an embodiment of the present invention is preferably 26 N or more, more preferably 27 N or more, and even more preferably 28 N or more. This allows the water-absorbing resin in accordance with an embodiment of the present invention to achieve an increased absorption capacity under load particularly on second and subsequent urinations over the conventional ones, for example, in a case where the water-absorbing resin in accordance with an embodiment of the present invention has been used in an absorbent body having a low proportion of fiber material such as pulp, and the absorbent body has been used in an absorbent article such as a thin disposable diaper. As described later, the "gel expansion force" defined in the present invention means a force for the water-absorbing resin further expanding against load after the absorption capacity of the water-absorbing resin has reached a predetermined absorption capacity. That is, the "gel expansion force" is an index for evaluating the ability of an absorbent article, such as a thin disposable diaper, having been swollen on first urination to absorb urine, even under load on the second and subsequent urinations. A gel expansion force of less than 26 N is not preferable for the reason of causing a water-absorbing resin to have an insufficient absorption capacity under load on the second and subsequent urinations, causing an absorbent body including the water-absorbing resin to have an insufficient amount of liquid trapped under load, and causing an absorbent article, such as a thin disposable diaper, including the absorbent body to have an insufficient liquid trapping function.

Further, an upper limit of the gel expansion force under a load of 4.83 kPa of the water-absorbing resin in accordance with an embodiment of the present invention is not particularly limited, but is preferably 40 N or less and more preferably 35 N or less.

As a water-absorbing resin evaluation method similar to the evaluation method based on the gel expansion force in the present invention, an evaluation method based on an initial swelling force is proposed in, for example, International Publication No. WO 2018/181548. This is a method of measuring, under a very light load which is 0.16 kPa (1.6 g/cm², 0.02 psi), a force of expansion of an unswollen water-absorbing resin. Further, for example, Japanese Patent No. 3210009 proposes an evaluation method based on a gel expansion pressure. This is a method of measuring a force for a water-absorbing resin further expanding without load after the absorption capacity of the water-absorbing resin has reached a predetermined absorption capacity without load. In contrast, the gel expansion force in the present invention is, as described later, a measurement of a force for the water-absorbing resin further expanding under a load of 4.83 kPa (49 g/cm², 0.7 psi) after the absorption capacity under a load of 4.83 kPa (49 g/cm², 0.7 psi) of the water-absorbing resin has reached a predetermined absorption capacity. Thus, the gel expansion force in the present invention is used for evaluation of a function that differs from the function evaluated by the evaluation method disclosed in the above-described conventional art document.

That is, it can be said that the gel expansion force in the present invention is an evaluation method that assumes, as a situation where the absorbent article including the absorbent body or the water-absorbing resin is used, a situation where the absorbent article absorbs urine discharged on multiple instances of urinations under a condition where the absorbent article is under load during the urinations, and is an evaluation method carried out in a harsh environment that assumes a more actual use for the absorbent article as compared to the evaluation method carried out under a very light load or without load as proposed in the above-described conventional art document.

In addition, an object of the present invention is to provide an absorbent body that exhibits an excellent amount of liquid trapped under load on the second and subsequent urinations and a water-absorbing resin that has an excellent absorption capacity under load on the second and subsequent urinations. For the prediction of urine absorption on the second and subsequent urinations under load, the evaluation method proposed in the above-described conventional art document is meaningless, and the method of evaluating a force for an absorbing resin further expanding after the absorbing resin has been once swollen under load in the present invention is necessary.

The gel expansion force under a load of 4.83 kPa can be controlled by adjusting, for example, the absorption capacity (CRC, AAP) of the water-absorbing resin, the particle shape (shape that is a non-uniform shape and is a shape such that cavities and voids exist in the particle) thereof, and the particle size thereof. Carrying out these adjustments makes it possible to control the gel expansion force under a load of 4.83 kPa to be 26 N or more.

In addition to the gel expansion force, the gel expansion speed under a load of 4.83 kPa of the water-absorbing resin in accordance with an embodiment of the present invention is preferably 8.5 or more, more preferably 9.0 or more, and even more preferably 9.5 or more. This allows the water-absorbing resin in accordance with an embodiment of the present invention to achieve a further increased absorption capacity under load on the second and subsequent urinations, in the case where the water-absorbing resin in accordance with an embodiment of the present invention has been used in an absorbent body having a low proportion of fiber material such as pulp and in an absorbent article, such as a thin disposable diaper, including the absorbent body.

Further, an upper limit of the gel expansion speed under a load of 4.83 kPa of the water-absorbing resin in accordance with an embodiment of the present invention is not particularly limited, but is preferably 15.0 or less and more preferably 14.0 or less.

As a conventional water-absorbing resin evaluation method, there have been proposed methods in which the absorption speed without load or under load is evaluated. However, in all of these methods, the absorption speed of an unswollen water-absorbing resin after having come into contact with an absorbed liquid such as saline is evaluated. In contrast, in the evaluation method based on the gel expansion speed in the present invention, a speed at which a water-absorbing resin further expands under load after the absorption capacity of the water-absorbing resin has reached a predetermined absorption capacity under load is measured. From this fact, it can be said that the gel expansion speed in the present invention, like the gel expansion force, is an evaluation method that assumes an actual use in an absorbent article which needs to absorb urine discharged on multiple instances of urinations under load.

A ratio of a volume of particles having a cavity volume ratio of 15 volume % or more to a total volume of the water-absorbing resin in accordance with an embodiment of the present invention is preferably 40 volume % or more, more preferably 42 volume % or more, and even more preferably 44 volume % or more. A water-absorbing resin having a high cavity volume ratio tends to have a large specific surface area. Note that the cavity volume ratio is determined to evaluate a volume of recesses on a particle surface that cannot be sufficiently evaluated only by measuring a specific surface area. An increase in cavity volume ratio increases a gap between gel particles of a swollen water-absorbing resin, and increases the amount of water-based liquid retained in a cavity volume part of the gel particles and the amount of water-based liquid retained in the gap between the gel particles. As a result, the gel expansion force is controlled. This allows the water-absorbing resin in accordance with an embodiment of the present invention to achieve a further increased absorption capacity under load on the second and subsequent urinations, in the case where the water-absorbing resin in accordance with an embodiment of the present invention has been used in an absorbent body having a low proportion of fiber material such as pulp and in an absorbent article, such as a thin disposable diaper, including the absorbent body.

Here, in the present invention, the cavity refers to a hollow that is connected to the outside of a water-absorbing resin 1 (exposed at the surface of the water-absorbing resin 1) among hollows formed in the water-absorbing resin 1, as illustrated in FIG. 1. The hollow also includes a depression, a groove, and the like that are formed at the surface of the water-absorbing resin 1. Specifically, the cavity refers to a hole, a through-hole, a depression, a groove, and the like the existence of which can be recognized at the surface of the water-absorbing resin 1 when, as described later, three-dimensional image data has been acquired under the conditions described below with use of Microfocus X-ray CT system (inspeXio SMX-100CT; manufactured by Shimadzu Corporation), and the three-dimensional image data has been analyzed under the conditions described below with use of high-speed three-dimensional analysis software (TRI/3D-VOL-FCS64; manufactured by Ratoc System Engineering Co., Ltd.).

A ratio of a volume of particles having a void volume ratio of 1 volume % or less to a total volume of the water-absorbing resin in accordance with an embodiment of the present invention is preferably 65 volume % or more, more preferably 67 volume % or more, even more preferably 70 volume % or more, further more preferably 72 volume % or more, and still more preferably 73 volume % or more. As a result, the gel expansion force is controlled. This allows the water-absorbing resin in accordance with an embodiment of the present invention to achieve a further increased absorption capacity under load on the second and subsequent urinations, for example, in the case where the water-absorbing resin in accordance with an embodiment of the present invention has been used in an absorbent article, such as a thin disposable diaper. Note that a water-absorbing resin having a high void volume ratio is more likely to be collapsed by pressure when swollen and thus has a decreased absorption capacity under load on the second and subsequent urinations, in the case where the water-absorbing resin has been used in an absorbent body having a low proportion of fiber material such as pulp and in an absorbent article, such as a thin disposable diaper, including the absorbent body.

Here, in the present invention, the void refers to a hollow, such as a closed cell, that is not connected to the outside of the water-absorbing resin 1 (exists inside the water-absorbing resin 1) among the hollows formed in the water-absorbing resin 1, as illustrated in FIG. 1. Specifically, the void refers to a closed cell and the like hollow the existence of which can be recognized inside the water-absorbing resin 1 when, as described later, three-dimensional image data has been acquired under the conditions described below with use of Microfocus X-ray CT system (inspeXio SMX-100CT; manufactured by Shimadzu Corporation), and the three-dimensional image data has been analyzed under the conditions described below with use of high-speed three-dimensional analysis software (TRI/3D-VOL-FCS64; manufactured by Ratoc System Engineering Co., Ltd.).

A ratio of a volume of particles having a cavity volume ratio of 15 volume % or more and a void volume ratio of 1 volume % or less to a total volume of the water-absorbing resin is preferably 20 volume % or more, and even more preferably 25 volume % or more. As a result, the gel expansion force is controlled. This allows the water-absorbing resin used in an embodiment of the present invention to achieve a further increased absorption capacity under load on the second and subsequent urinations, in the case where the water-absorbing resin in accordance with an embodiment of the present invention has been used in an absorbent body having a low proportion of fiber material such as pulp and in an absorbent article, such as a thin disposable diaper, including the absorbent body.

The water-absorbing resin in accordance with an embodiment of the present invention has an absorption capacity without load (CRC) of preferably 25 g/g or more, more preferably 27 g/g or more, and even more preferably 28 g/g or more. As a result, the gel expansion force is controlled. This allows the water-absorbing resin in accordance with an embodiment of the present invention to achieve a further increased absorption capacity under load on the second and subsequent urinations, in the case where the water-absorbing resin in accordance with an embodiment of the present invention has been used in an absorbent body having a low proportion of fiber material such as pulp and in an absorbent article, such as a thin disposable diaper, including the absorbent body.

Note that an upper limit of the absorption capacity without load (CRC) is not particularly limited, but is preferably 40 g/g or less, and more preferably 38 g/g or less, so that the absorption capacity under load (AAP) and saline flow conductivity (SFC) are within desired ranges.

The water-absorbing resin in accordance with an embodiment of the present invention has an absorption capacity under load (AAP) under a load of 4.83 kPa of preferably 20 g/g or more, more preferably 23 g/g or more, even more preferably 24 g/g or more, particularly preferably 24.5 g/g or more, and most preferably 25 g/g or more. As a result, the gel expansion force is controlled. Thus, in the case where the water-absorbing resin in accordance with an embodiment of the present invention has been used in an absorbent body having a low proportion of fiber material such as pulp and in an absorbent article, such as a thin disposable diaper, including the absorbent body, the water-absorbing resin in accordance with an embodiment of the present invention achieves a further increased absorption capacity under load relative to a total amount of discharged urine to be absorbed by the absorbent article such as a disposable diaper. Note that an upper limit of the absorption capacity under load (AAP) is not particularly limited, but is preferably 35 g/g or less, without exceeding the absorption capacity without load (CRC).

In addition to the gel expansion force, the saline flow conductivity (SFC) of the water-absorbing resin in accordance with an embodiment of the present invention, which is determined to evaluate a liquid diffusion performance of the water-absorbing resin in accordance with an embodiment of the present invention, is preferably $15(\times 10^{-7}$ $cm^3 \cdot sec/g)$ or more, more preferably 18 $(\times 10^{-7} \; cm^3 \cdot sec/g)$ or more, even more preferably 20 $(\times 10^{-7} \; cm^3 \cdot sec/g)$ or more, preferably $55(\times 10^{-7} \; cm^3 \cdot sec/g)$ or less, and more preferably 53 $(\times 10^{-7} \; cm^3 \cdot sec/g)$ or less. In a case where the saline flow conductivity (SFC) is $15(\times 10^{-7} \; cm^3 \cdot sec/g)$ or more and $55(\times 10^{-7} \; cm^3 \cdot sec/g)$ or less, the water-absorbing resin in accordance with an embodiment of the present invention can take on a liquid diffusion capability that was taken on by pulp in the conventional absorbent body. Thus, even in a case where the water-absorbing resin in accordance with an embodiment of the present invention has been used in an absorbent body having a low proportion of fiber material such as pulp and in an absorbent article, such as a thin disposable diaper, including the absorbent body, the absorbent body and the absorbent article such as a disposable diaper exhibit good performance without having a decreased liquid diffusion capability caused by gel blocking.

Note that an upper limit of the saline flow conductivity (SFC) is not particularly limited. However, since the saline flow conductivity (SFC) and the absorption capacity without load (CRC) are in a trade-off relationship, an excessively high saline flow conductivity (SFC) leads to a failure to obtain an absorption capacity without load (CRC) within a desired range.

The water-absorbing resin in accordance with an embodiment of the present invention has a mass average particle diameter (D50) of preferably 250 µm or more, more preferably 300 µm or more, preferably 550 µm or less, and more preferably 500 µm or less. Further, a mass of a water-absorbing resin having a particle diameter of less than 150 µm accounts for preferably 3 mass % or less, and more preferably 2 mass % or less, of a total mass of the water-absorbing resin in accordance with an embodiment of the present invention. As a result, the gel expansion force is controlled. Further, the water-absorbing resin in accordance with an embodiment of the present invention has a function of keeping the above-described CRC, AAP, and SFC in balance. This allows the water-absorbing resin in accordance with an embodiment of the present invention to achieve a further increased absorption capacity under load on the second and subsequent urinations, in the case where the water-absorbing resin in accordance with an embodiment of the present invention has been used in an absorbent body having a low proportion of fiber material such as pulp and in an absorbent article, such as a thin disposable diaper, including the absorbent body.

Further, a mass of a water-absorbing resin having a particle diameter of more than 710 µm accounts for preferably 2 mass % or less, and more preferably 1 mass % or less, of a total mass of the water-absorbing resin in accordance with an embodiment of the present invention. This is preferable for the reason of allowing the water-absorbing resin in accordance with an embodiment of the present invention to reduce a roughness feeling of a water-absorbing resin and improve a wearing comfort, in a case where the water-absorbing resin in accordance with an embodiment of the present invention has been used particularly in an absorbent body having a low proportion of fiber material such as pulp and in a sanitary material, such as a thin disposable diaper, including the absorbent body.

To control the gel expansion force, the absorption capacity (CRC, AAP), particle shape (non-uniform shape such that cavities and voids exist in a particle), and particle size of the water-absorbing resin are adjusted. Preferably, the CRC, AAP, cavity volume ratio, void volume ratio, and particle size of the water-absorbing resin are adjusted. More preferably, at least one or more (preferably two or more, more preferably three or more, particularly preferably four or more, and most preferably all) selected from the group consisting of CRC, AAP, intra-particle cavity volume ratio, intra-particle void volume ratio, and particle size of the water-absorbing resin is/are adjusted so as to be within any of the above-described ranges.

In addition to the gel expansion force, a 5-mm gel thickness reach time of the water-absorbing resin in accordance with an embodiment of the present invention is preferably 150 seconds or less, and more preferably 140 seconds or less. This allows the water-absorbing resin in accordance with an embodiment of the present invention to achieve a further increased absorption capacity under load on the second and subsequent urinations, in the case where the water-absorbing resin in accordance with an embodiment of the present invention has been used in an absorbent body having a low proportion of fiber material such as pulp and in an absorbent article, such as a thin disposable diaper, including the absorbent body.

Then, the water-absorbing resin in accordance with an embodiment of the present invention at least having the gel expansion force that is within any of the above-described ranges has an absorption capacity under load on the second urination of 14 $cm^3/g$ or more, preferably 14.2 $cm^3/g$ or more, more preferably 14.4 $cm^3/g$ or more, and even more preferably 14.6 $cm^3/g$ or more.

Note that, as an initial color tone of the water-absorbing resin in accordance with an embodiment of the present invention, a WI value is preferably 45 or more, more preferably 50 or more, and even more preferably 52 or more. This is preferable since, for example, in a case where the water-absorbing resin in accordance with an embodiment of the present invention has been used in an absorbent body having a low proportion of fiber material such as pulp, and the absorbent body has been used in an upper layer part of an absorbent article such as a thin disposable diaper, the absorbent article can maintain cleanness, i.e. a state of being white.

[4] Application of Water-Absorbing Resin (Absorbent Body)

An application of the water-absorbing resin in accordance with an embodiment of the present invention is not particularly limited. However, the water-absorbing resin in accordance with an embodiment of the present invention is preferably used in an absorbent body of an absorbent article such as a disposable diaper, and more preferably used in an absorbent body which has a high mass ratio of a water-absorbing resin used in an absorbent article such as a thin disposable diaper.

The absorbent body generally contains, as components thereof, not only the water-absorbing resin, but also a fiber material (hydrophilic fibers) such as wood-ground pulp. In a case where the absorbent body contains the water-absorbing resin and the hydrophilic fibers, examples of the structure of the absorbent body include a structure which contains the water-absorbing resin and the hydrophilic fibers being uniformly mixed. Specifically, examples of the structure include a structural body formed simply by uniformly mixing a water-absorbing resin and hydrophilic fibers; a structural body in which layered hydrophilic fibers are laminated on a layer in which a water-absorbing resin and hydrophilic fibers are uniformly mixed; and a structural body in which a water-absorbing resin is arranged between the layered hydrophilic fibers and the layer in which a water-absorbing resin and hydrophilic fibers are uniformly mixed. In addition to these structural bodies, for example, a structural body in which a water-absorbing resin is arranged in between the layered hydrophilic fibers may be employed. Note that the structure of the absorbent body is not limited to the above-described example structural bodies.

Examples of the hydrophilic fibers, include, in addition to the above-described wood-ground pulp (mechanical pulp obtained from wood), hydrophilic fibers including, for example, cellulose fibers such as chemical pulp, semi-chemical pulp, and dissolving pulp and artificial cellulose fibers such as rayon and acetate. Of the above-described example hydrophilic fibers, cellulose fibers are preferable. Further, the hydrophilic fibers can contain synthetic fibers such as polyamide, polyester, and polyolefin. Note that the hydrophilic fibers are not limited to the above-described example fibers.

Further, a ratio of a mass of the water-absorbing resin to a mass of the absorbent body is preferably 75 mass % to 100 mass %, more preferably 80 mass % to 100 mass %, even more preferably 85 mass % to 100 mass %, and particularly preferably 90 mass % to 100 mass %. Setting the ratio of the mass of the water-absorbing resin to the mass of the absorbent body to be within any of the above-described ranges is preferable since such a setting allows an absorbent article to undergo a recent trend of being reduced in thickness. Further, setting the ratio of the mass of the water-absorbing resin to the mass of the absorbent body to be within any of the above-described ranges is preferable since, in a case where the absorbent body is used as an upper layer part of an absorbent article, the absorbent article can maintain cleanness, i.e. a state of being white.

Further, an adhesive binder may be used in order to increase the strength and shape retainability of the absorbent body before and during use of the absorbent body. Examples of the adhesive binder include: heat-fusing fibers such as polyolefin fibers such as polyethylene, polypropylene, ethylene-propylene copolymer, and 1-butene-ethylene copolymer; and emulsions having adhesiveness. It is possible to use only one of these adhesive binders or a mixture of two or more thereof. A mass ratio between the water-absorbing resin and the adhesive binder is preferably in a range of 50/50 to 99/1, more preferably in a range of 70/30 to 95/5, and even more preferably 80/20 to 95/5.

Further, the absorbent body may have, as other structure of the absorbent body, for example, a structure in which a layer containing the above-described water-absorbing resin and hydrophilic fibers (including: a layer in which the water-absorbing resin and the hydrophilic fibers are uniformly mixed; a structural body in which layered hydrophilic fibers are laminated on the layer in which the water-absorbing resin and the hydrophilic fibers are uniformly mixed; a structural body in which the water-absorbing resin is arranged between the layered hydrophilic fibers and the layer in which the water-absorbing resin and the hydrophilic fibers are uniformly mixed; a structural body in which the water-absorbing resin is arranged between the layered hydrophilic fibers; and the like) is sandwiched by a nonwoven fabric from above and/or from below. The nonwoven fabric is not particularly limited as long as it is a nonwoven fabric publicly known in the technical field of absorbent bodies. Examples of the nonwoven fabric include a nonwoven fabric made of: polyolefin fibers such as polyethylene (PE) and polypropylene (PP); polyester fibers such as polyethylene terephthalate (PET), polytrimethylene terephthalate (PTT), and polyethylene naphthalate (PEN); polyamide fibers such as nylon; rayon fibers; and/or other synthetic fibers; a nonwoven fabric produced by mixing the synthetic fibers with, for example, cotton, silk, hemp, and/or pulp (cellulose) fibers; and the like. A mass per unit area of the nonwoven fabric may be 5 g/m² to 300 g/m². Further, a thickness of the nonwoven fabric may be 20 µm to 800 µm. The liquid diffusion area of the nonwoven fabric (described later) may be 1 m² to 100 m².

Further, a form of the absorbent body is not particularly limited. However, the absorbent body is preferably formed in, for example, a sheet form, a fiber form, or a cylindrical form, and is more preferably formed in a sheet form.

Then, the absorbent body in accordance with an embodiment of the present invention contains a water-absorbing resin essentially having a gel expansion force under a load of 4.83 kPa of 26 N or more, preferably further having an absorption capacity under load of 14 cm³/g or more on the second and subsequent urinations, and more preferably further satisfying the physical properties described in [3] Water-absorbing resin above. This allows the absorbent body in accordance with an embodiment of the present invention to have an increased amount of liquid trapped under load on the second and subsequent urinations. The amount of liquid trapped under load on the second and subsequent urinations is preferably 34.5 g or more, more preferably 35.0 g, and even more preferably 35.5 g or more. Further, the amount of liquid trapped under load on the first and second urinations is preferably 72.0 g or more, more preferably 72.5 g or more, and even more preferably 73.0 g or more. This allows the absorbent body in accordance with an embodiment of the present invention to, for example, in a case where the absorbent body in accordance with an embodiment of the present invention has been used in an absorbent article such as a thin disposable diaper, achieve an increased absorption capacity under load of the absorbent body particularly on second and subsequent urinations and achieve an improved liquid trapping function of the absorbent article on the second and subsequent urinations.

Note that, as an application of the water-absorbing resin in accordance with an embodiment of the present invention, the water-absorbing resin may be suitably used not only in an absorbent body included in an absorbent article such as the above-described sanitary products, but also in various applications such as animal urine absorbents, urine gelling agents for portable toilets, freshness keeping agents for fruits, vegetables, and the like, drip absorbers for meat and fishery products, ice packs, disposable body warmers, gelling agents for batteries, agricultural and horticultural soil water retaining agents (for plants, soil, and the like), dew condensation preventing agents, industrial waterproofing agents and packing agents, and artificial snow.

[5] Application of Absorbent Body (Absorbent Article)

An application of the absorbent body in accordance with an embodiment of the present invention is not particularly limited. However, the absorbent body in accordance with an embodiment of the present invention is preferably used in an absorbent article such as a disposable diaper and more preferably used in an absorbent article such as a thin disposable diaper.

In a case where the absorbent article is, for example, a disposable diaper, the disposable diaper is produced in such a manner that an absorbent layer including the absorbent body in accordance with an embodiment of the present invention is sandwiched between a liquid permeable top sheet and a liquid impermeable back sheet, the liquid permeable top sheet being positioned on a side of the disposable diaper which comes in contact with the wearer's skin during wearing, the liquid impermeable back sheet being positioned on a side of the disposable diaper which is an outward side during wearing. The liquid permeable top sheet (hereinafter referred to as a liquid permeable sheet) is composed of a material having the property of allowing a water-based liquid to pass therethrough. Examples of the material of the liquid permeable sheet include a nonwoven fabric; a woven fabric; and a porous synthetic resin film made of polyethylene, polypropylene, polyester, polyamide, or the like. The liquid impermeable back sheet (hereinafter referred to as a liquid impermeable sheet) is composed of a material having the property of not allowing a water-based liquid to pass therethrough. Examples of the material of the liquid impermeable sheet include: a synthetic resin film made of polyethylene, polypropylene, ethylene vinyl acetate, polyvinyl chloride, or the like; a film composed of a composite material of any of these synthetic resins and a nonwoven fabric; and a film composed of a composite material of any of the above-described synthetic resins and a woven fabric. Note that the liquid impermeable sheet may have the property of allowing a vapor to pass therethrough. Further, in the absorbent article such as a disposable diaper, a diffusion layer composed of a material which helps liquid dispersion, such as a nonwoven fabric, cellulose, and cross-linked cellulose, can be arranged between the liquid permeable sheet and the absorbent layer. Further, the absorbent article such as a disposable diaper also includes members which are known to a person skilled in the art, such as adhesive tape for fixing the disposable diaper after it has been put on by the wearer.

The absorbent layer is configured to include an absorbent body, and is not particularly limited except for such a configuration. For example, by adding, to the absorbent layer, an additive such as a deodorizing agent, an antibacterial agent, a perfume, various kinds of inorganic powder, a foaming agent, a pigment, a dye, hydrophilic short fibers, a fertilizer, an oxidizing agent, a reducing agent, water, and a salt, various functions may be imparted to the absorbent body or the absorbent article. Alternatively, the absorbent layer may be configured to contain none of the above-described additives (configured to contain an absorbent body only).

Further, a method for producing the absorbent layer is not particularly limited. Moreover, a method of sandwiching the absorbent layer between the liquid permeable sheet and the liquid impermeable sheet, i.e. a method for producing the absorbent article, is not particularly limited.

Then, the absorbent article in accordance with an embodiment of the present invention has an absorbent body having improved liquid trapping under load on the second and subsequent urinations and thus exhibits an excellent liquid trapping function on the second and subsequent urinations.

Note that, as an application of the absorbent body in accordance with an embodiment of the present invention, the absorbent body may be suitably used not only in the above-described absorbent article, but also in various applications such as animal urine absorbents, urine gelling agents for portable toilets, freshness keeping agents for fruits, vegetables, and the like, drip absorbers for meat and fishery products, ice packs, disposable body warmers, gelling agents for batteries, agricultural and horticultural soil water retaining agents (for plants, soil, and the like), dew condensation preventing agents, industrial waterproofing agents and packing agents, and artificial snow.

EXAMPLES

The following description will discuss the present invention in more detail with reference to Examples and Comparative Examples. However, the present invention is not limited to these Examples.

Example 1

(Step of Preparing Aqueous Monomer Solution)

Into a 2-liter polypropylene container were introduced 422.0 parts by mass of acrylic acid, 173.9 parts by mass of a 48.5 mass % aqueous sodium hydroxide solution, 2.5 parts by mass of polyethyleneglycol diacrylate (average molecular weight: 523), 2.6 parts by mass of a 1.0 mass % aqueous diethylenetriamine pentaacetic acid/trisodium solution, and 403.3 parts by mass of deionized water. These substances were mixed so that an aqueous monomer solution was prepared. The liquid temperature of the aqueous monomer solution exceeded 40° C. due to heat of neutralization and heat of dissolution which were generated during the mixing.

(Polymerization Step)

Next, the aqueous monomer solution was cooled while being stirred. At a point in time at which the liquid temperature reached 40° C., 178.7 parts by mass of a 48.5 mass % aqueous sodium hydroxide solution having a temperature adjusted to 40° C. was added to and mixed with the aqueous monomer solution in an atmospheric air open state over a period of approximately 20 seconds (neutralization at a second stage commenced). In this way, an aqueous monomer solution (1) was prepared. At this time, the liquid temperature of the aqueous monomer solution (1) increased to approximately 78° C. due to heat of neutralization and heat of dissolution which were generated during the mixing. A precipitate was observed immediately after the start of the mixing of the aqueous sodium hydroxide solution with the aqueous monomer solution, but was gradually dissolved. In this way, the prepared aqueous monomer solution (1) became a transparent uniform solution.

Then, to the aqueous monomer solution (1) in a state of being stirred, nitrogen gas was introduced at a pressure of 0.1 MPa and at a flow rate of 0.1 L/min for 5 seconds with the use of Kinoshita glass ball filter (filter particle No. 4; manufactured by Kinoshita Rika Kogyo Co., Ltd.). Next, 18.4 parts by mass of a 4.5 mass % aqueous sodium persulfate solution was added to the aqueous monomer solution (1). Immediately after that, the aqueous monomer solution (1) was poured into a stainless steel vat-type vessel (with a bottom surface of 340 mm×340 mm and a height of 25 mm; inner surface: Teflon (registered trademark) coating) in an atmospheric air open state. Note that pouring of the aqueous monomer solution (1) into the vat-type vessel commenced 65 seconds after the start of the second-stage neutralization. Further, the vat-type vessel was heated with use of a hot plate (NEO HOTPLATE HI-1000; manufactured by Iuchi Seiei Do Ltd.) until a surface temperature reached 50° C.

After the aqueous monomer solution (1) was poured into the vat-type vessel, a polymerization reaction commenced within 1 minute. In this polymerization reaction, polymerization of the aqueous monomer solution (1) proceeded while the aqueous monomer solution (1) gave off water vapor and swelled and foamed in various directions. After that, an obtained polymer shrunk to a size slightly larger than the bottom surface of the vat-type vessel. A hydrogel (1) was removed from the vat-type vessel after 2 minutes had passed since the commencement of the polymerization reaction. Note that this series of operations was carried out in an atmospheric air open state.

(Gel-Crushing Step)

Next, the hydrogel (1) obtained through the above-described polymerization reaction was cut such that a mass on a per-hydrogel basis was about 60 g, and was then subjected to gel-crushing with use of a meat chopper (HL-G22SN; plate pore diameter: 6.0 mm; manufactured by Remacom Co., Ltd.), so that a particulate hydrogel (1) was obtained. The hydrogel (1) was introduced into the meat chopper at a rate of about 360 g/min. The gel-crushing was carried out while deionized water having a temperature adjusted to 90° C. was being added to the meat chopper at a rate of 25 g/min simultaneously with the introduction of the hydrogel (1).

The particulate hydrogel (1) had D50 (mass average particle diameter) of 320 μm and had σig (logarithmic standard deviation of a particle size distribution) of 0.91.

(Drying Step)

Next, the particulate hydrogel (1) was spread onto a metal gauze with a mesh size of 300 μm and then placed in a hot air dryer. After that, the particulate hydrogel (1) was dried by passing hot air having a temperature of 190° C. over the particulate hydrogel (1) for 30 minutes. In this way, a dried polymer (1) was obtained. No undried material was found in the dried polymer (1).

(Classification Step)

Next, the dried polymer (1) was introduced into a roll mill (WML-type roll pulverizer; manufactured by Inoguchi Giken Ltd.) and pulverized. Thereafter, the dried polymer (1) thus pulverized was classified with use of two JIS standard sieves having respective mesh sizes of 710 μm and 150 μm. Obtained by this operation was a water-absorbing resin (1) having a non-uniformly pulverized shape before surface-crosslinking that had passed through the sieve having the mesh size of 710 μm and remained on the sieve having the mesh size of 150 μm.

(Surface-Crosslinking Step)

Next, to 100 parts by mass of the water-absorbing resin (1) before surface-crosslinking, an aqueous surface-crosslinking agent solution containing 0.4 parts by mass of ethylene carbonate, 0.7 parts by mass of propylene glycol, 2.9 parts by mass of deionized water, and 0.001 parts by mass of polyoxyethylene (20) sorbitan monostearate (manufactured by Kao Corporation) was added by spraying and mixed uniformly. After that, a mixture thus obtained was subjected to surface-crosslinking by a heating treatment at 200° C. for 40 minutes. Then, the mixture was classified with use of two JIS standard sieves having respective mesh sizes of 710 μm and 150 μm. Obtained by this operation was a water-absorbing resin (1) after surface-crosslinking that had passed through the sieve having the mesh size of 710 μm and remained on the sieve having the mesh size of 150 μm. Physical properties of the water-absorbing resin (1) after surface-crosslinking are shown in Table 2. Note that, as an initial color tone of the water-absorbing resin (1), a WI value was 52.4.

Example 2

A water-absorbing resin (2) after surface-crosslinking was obtained by carrying out the same operations as the operations in Example 1, except that the aqueous surface-crosslinking agent solution used in Example 1 was changed to an aqueous surface-crosslinking agent solution containing 0.2 parts by mass of 1,6-hexanediol, 0.6 parts by mass of triethylene glycol, 2.6 parts by mass of deionized water, and 0.001 parts by mass of polyoxyethylene (20) sorbitan monostearate (manufactured by Kao Corporation). Physical properties of the water-absorbing resin (2) after surface-crosslinking are shown in Table 2.

Note that, as an initial color tone of the water-absorbing resin (2), a WI value was 53.0.

Note that a particulate hydrogel (2) obtained by carrying out the gel-crushing step had D50 (mass average particle diameter) of 330 μm and had cig (logarithmic standard deviation of a particle size distribution) of 0.92.

Example 3

A particulate hydrogel (3) was obtained by carrying out the same operations as the operations in Example 1, except that the amount of deionized water to be added when the gel-crushing step was carried out in Example 1 was changed to 50 g/min.

The particulate hydrogel (3) had D50 (mass average particle diameter) of 400 μm and had cig (logarithmic standard deviation of a particle size distribution) of 0.95.

(Drying Step)

Next, the particulate hydrogel (3) was spread onto a metal gauze with a mesh size of 300 μm and then placed in a hot air dryer. After that, the particulate hydrogel (3) was dried by passing hot air having a temperature of 190° C. over the particulate hydrogel (3) for 30 minutes. In this way, a dried polymer (3) was obtained. No undried material was found in the dried polymer (3).

(Classification Step)

Next, the dried polymer (3) was introduced into a roll mill (WML-type roll pulverizer; manufactured by Inoguchi Giken Ltd.) and pulverized. Thereafter, the dried polymer (3) thus pulverized was classified with use of two JIS standard sieves having respective mesh sizes of 710 μm and 150 μm. Obtained by this operation were a water-absorbing resin (3) having a non-uniformly pulverized shape before surface-crosslinking that had passed through the sieve having the mesh size of 710 μm and remained on the sieve having the mesh size of 150 μm and fine powder (3-1) that had passed through the sieve having the mesh size of 150 μm.

(Surface-Crosslinking Step)

Next, to 100 parts by mass of the water-absorbing resin (3) before surface-crosslinking, an aqueous surface-crosslinking agent solution containing 0.4 parts by mass of ethylene carbonate, 0.7 parts by mass of propylene glycol, 2.9 parts by mass of deionized water, and 0.001 parts by mass of polyoxyethylene (20) sorbitan monostearate (manufactured by Kao Corporation) was added by spraying and mixed uniformly. After that, a mixture thus obtained was subjected to surface-crosslinking by carrying out heating treatment at 200° C. for 40 minutes. Then, the mixture was classified with use of two JIS standard sieves having respective mesh sizes of 710 μm and 150 μm. Obtained by this operation were the water-absorbing resin (3) after surface-crosslinking that had passed through the sieve having the mesh size of 710 μm and remained on the sieve having the mesh size of 150 μm and fine powder (3-2) that had passed through the sieve having the mesh size of 150 μm.

(Granulation Step)

Next, the fine powder (3-1) and the fine powder (3-2) were mixed in mass proportions of 17:3 (w:w), and a resulting mixture was considered to be fine powder (3-3). The fine powder (3-3) had D50 (mass average particle diameter) of 85 μm. Then, after 60 parts by mass of the fine powder (3-3) was heated to 70° C., the fine powder (3-3) was introduced into a food processor (MK-K48P; manufactured by Panasonic Corporation). 49 parts by mass of deionized water having a temperature adjusted to 80° C. was added to the fine powder (3-3) while being stirred. These substances were mixed for 30 seconds so that a granulated gel (3-3) was obtained.

(Granulated Gel Addition Step)

Next, after 1 minute had passed since the commencement of the granulation, 80 parts by mass of the granulated gel (3-3) was added to 320 parts by mass of the particulate hydrogel (3) that had been prepared by carrying out the above-described operation again. Immediately after the addition, these substances were mixed for 10 seconds in a mortar mixer (manufactured by Nishinihonshikenki) that had been heated to 80° C., so that a mixed gel (3-4) was obtained. Note that the temperature of the granulated gel (3-3) and the temperature of the particulate hydrogel (3) immediately before the granulated gel (3-3) and the particulate hydrogel (3) were mixed in the mortar mixer were 55° C. and 50° C., respectively. Further, mixability of the granulated gel (3-3) and the particulate hydrogel (3) in the mortar mixer was good.

(Drying Step)

Next, the mixed gel (3-4) was spread onto a metal gauze with a mesh size of 300 μm and then placed in a hot air dryer. After that, the mixed gel (3-4) was dried by passing hot air having a temperature of 190° C. over the mixed gel (3-4) for 30 minutes. In this way, a dried polymer (3-4) was obtained. No undried material was found in the dried polymer (3-4).

(Classification Step)

Next, the dried polymer (3-4) was introduced into a roll mill (WML-type roll pulverizer; manufactured by Inoguchi Giken Ltd.) and pulverized. Thereafter, the dried polymer (3-4) thus pulverized was classified with use of two JIS standard sieves having respective mesh sizes of 710 μm and 150 μm. Obtained by this operation was a water-absorbing resin (3-4) having a non-uniformly pulverized shape before surface-crosslinking that had passed through the sieve having the mesh size of 710 μm and remained on the sieve having the mesh size of 150 μm.

(Surface-Crosslinking Step)

Next, to 100 parts by mass of the water-absorbing resin (3-4) before surface-crosslinking, an aqueous surface-crosslinking agent solution containing 0.4 parts by mass of ethylene carbonate, 0.7 parts by mass of propylene glycol, 2.9 parts by mass of deionized water, and 0.001 parts by mass of polyoxyethylene (20) sorbitan monostearate (manufactured by Kao Corporation) was added by spraying and mixed uniformly. After that, a mixture thus obtained was subjected to surface-crosslinking by carrying out heating treatment at 200° C. for 40 minutes. Then, the mixture was classified with use of two JIS standard sieves having respective mesh sizes of 710 μm and 150 μm. Obtained by this operation was a water-absorbing resin (3-4) after surface-crosslinking that had passed through the sieve having the mesh size of 710 μm and remained on the sieve having the mesh size of 150 μm. Physical properties of the water-absorbing resin (3-4) after surface-crosslinking are shown in Table 2.

Note that, as an initial color tone of the water-absorbing resin (3-4), a WI value was 54.7.

Example 4

A water-absorbing resin (4-4) after surface-crosslinking was obtained by carrying out the same operations as the operations in Example 3, except that the aqueous surface-crosslinking agent solution used in Example 3 was changed to an aqueous surface-crosslinking agent solution containing 0.2 parts by mass of 1,6-hexanediol, 0.6 parts by mass of triethylene glycol, 2.6 parts by mass of deionized water, and 0.001 parts by mass of polyoxyethylene (20) sorbitan monostearate (manufactured by Kao Corporation).

Physical properties of the water-absorbing resin (4-4) after surface-crosslinking are shown in Table 2.

Note that, as an initial color tone of the water-absorbing resin (4-4), a WI value was 52.6.

Note that a particulate hydrogel (4) obtained by carrying out the gel-crushing step had D50 (mass average particle diameter) of 410 μm and had cig (logarithmic standard deviation of a particle size distribution) of 0.94.

Comparative Example 1

(Step of Preparing Aqueous Monomer Solution)

Into a 2-liter polypropylene container were introduced 421.7 parts by mass of acrylic acid, 140.4 parts by mass of a 48.5 mass % aqueous sodium hydroxide solution, 2.4 parts by mass of polyethyleneglycol diacrylate (average molecular weight: 523), 11.3 parts by mass of a 1.0 mass % aqueous diethylenetriamine pentaacetic acid/trisodium solution, and 390.3 parts by mass of deionized water. These substances were mixed so that an aqueous monomer solution was prepared. The liquid temperature of the aqueous monomer solution exceeded 40° C. due to heat of neutralization and heat of dissolution which were generated during the mixing.

(Polymerization Step)

Next, the aqueous monomer solution was cooled while being stirred. At a point in time at which the liquid temperature reached 38.3° C., 4.4 parts by mass of a 1.0 mass % aqueous polyoxyethylene (20) sorbitan monostearate solution (manufactured by Kao Corporation) was added. Further, at a point in time at which the liquid temperature reached 38.0° C., 211.9 parts by mass of a 48.5 mass % aqueous sodium hydroxide solution having a temperature adjusted to 40° C. was added to and mixed with the aqueous monomer solution in an atmospheric air open state over a period of approximately 20 seconds (neutralization at a second stage commenced). In this way, an aqueous monomer solution (1') was prepared. At this time, the liquid temperature of the aqueous monomer solution (1') increased to approximately 81° C. due to heat of neutralization and heat of dissolution which were generated during the mixing. A precipitate was observed immediately after the start of the mixing of the aqueous sodium hydroxide solution with the aqueous monomer solution, but was gradually dissolved. In this way, the prepared aqueous monomer solution (1') became a transparent uniform solution.

Then, to the aqueous monomer solution (1') in a state of being stirred, nitrogen gas was introduced at a pressure of 0.1 MPa and at a flow rate of 0.1 L/min for 10 seconds with the use of Kinoshita glass ball filter (filter particle No. 4; manufactured by Kinoshita Rika Kogyo Co., Ltd.). Next, 17.6 parts by mass of a 4.0 mass % aqueous sodium persulfate solution was added to the aqueous monomer solution (1'). Immediately after that, the aqueous monomer solution (1') was poured into a stainless steel vat-type vessel (with a bottom surface of 340 mm×340 mm and a height of 25 mm; inner surface: Teflon (registered trademark) coating) in an atmospheric air open state. Note that pouring of the aqueous monomer solution (1') into the vat-type vessel commenced 55 seconds after the start of the second-stage neutralization. Further, the vat-type vessel was heated with use of a hot plate (NEO HOTPLATE HI-1000; manufactured by Iuchi Seiei Do Ltd.) until a surface temperature reached 40° C.

After 59 seconds had passed since the pouring of the aqueous monomer solution (1') into the vat-type vessel, a polymerization reaction commenced. In this polymerization reaction, polymerization of the aqueous monomer solution (1') proceeded while the aqueous monomer solution (1') gave off water vapor and swelled and foamed in various directions. After that, an obtained polymer shrunk to a size slightly larger than the bottom surface of the vat-type vessel. A hydrogel (1') was removed from the vat-type vessel after 3 minutes had passed since the commencement of the polymerization reaction. Note that this series of operations was carried out in an atmospheric air open state.

(Gel-Crushing Step)

Next, the hydrogel (1') obtained through the above-described polymerization reaction was cut such that a mass on a per-hydrogel basis was about 60 g, and was then subjected to gel-crushing with use of a meat chopper (HL-G22SN; plate pore diameter: 6.0 mm; manufactured by Remacom Co., Ltd.), so that a particulate hydrogel (1') was obtained. The hydrogel (1') was introduced into the meat chopper at a rate of about 230 g/min. The gel-crushing was carried out while deionized water having a temperature adjusted to 90° C. was being added to the meat chopper at a rate of 50 g/min simultaneously with the introduction of the hydrogel (1').

The particulate hydrogel (1') had D50 (mass average particle diameter) of 350 μm and had cig (logarithmic standard deviation of a particle size distribution) of 0.93.

(Drying Step)

Next, the particulate hydrogel (1') was spread onto a metal gauze with a mesh size of 300 μm and then placed in a hot air dryer. After that, the particulate hydrogel (1') was dried by passing hot air having a temperature of 180° C. over the particulate hydrogel (1') for 30 minutes. In this way, a dried polymer (1') was obtained. No undried material was found in the dried polymer (1').

(Classification Step)

Next, the dried polymer (1') was introduced into a roll mill (WML-type roll pulverizer; manufactured by Inoguchi Giken Ltd.) and pulverized. Thereafter, the dried polymer (1') thus pulverized was classified with use of two JIS standard sieves having respective mesh sizes of 710 μm and 45 μm. Obtained by this operation was a water-absorbing resin (1') having a non-uniformly pulverized shape before surface-crosslinking that had passed through the sieve having the mesh size of 710 μm and remained on the sieve having the mesh size of 45 μm.

(Surface-Crosslinking Step)

Next, to 100 parts by mass of the water-absorbing resin (1') before surface-crosslinking, an aqueous surface-crosslinking agent solution containing 0.3 parts by mass of ethylene carbonate, 0.6 parts by mass of propylene glycol, 3.0 parts by mass of deionized water, and 0.001 parts by mass of polyoxyethylene (20) sorbitan monostearate (manufactured by Kao Corporation) was added by spraying and mixed uniformly. After that, a mixture thus obtained was subjected to surface-crosslinking by a heating treatment at 208° C. for 40 minutes. Then, the mixture was classified with use of two JIS standard sieves having respective mesh sizes of 710 μm and 45 μm. Obtained by this operation was a water-absorbing resin (1') after surface-crosslinking that had passed through the sieve having the mesh size of 710 μm and remained on the sieve having the mesh size of 45 μm.

Physical properties of the water-absorbing resin (1') after surface-crosslinking are shown in Table 2.

Comparative Example 2

(Step of Preparing Aqueous Monomer Solution)

Into a 2-liter polypropylene container were introduced 404.7 parts by mass of acrylic acid, 344.6 parts by mass of a 48.5 mass % aqueous sodium hydroxide solution, 2.2 parts by mass of polyethyleneglycol diacrylate (average molecular weight: 523), and 405.6 parts by mass of deionized water. These substances were mixed so that an aqueous monomer solution (2') was prepared. The liquid temperature of the aqueous monomer solution (2') exceeded 90° C. due to heat of neutralization and heat of dissolution which were generated during the mixing.

(Polymerization Step)

Next, while the aqueous monomer solution (2') was stirred with the liquid temperature thereof maintained at 90° C., 22.2 parts by mass of a 3.2 mass % aqueous sodium persulfate solution was added. Immediately after that, the aqueous monomer solution (2') was poured into a stainless steel vat-type vessel (with a bottom surface of 340 mm×340 mm and a height of 25 mm; inner surface: Teflon (registered trademark) coating) in an atmospheric air open state. Note that the vat-type vessel was heated with use of a hot plate (NEO HOTPLATE HI-1000; manufactured by Iuchi Seiei Do Ltd.) until a surface temperature reached 50° C.

After the aqueous monomer solution (2') was poured into the vat-type vessel, a polymerization reaction commenced immediately. In this polymerization reaction, polymerization of the aqueous monomer solution (2') proceeded while the aqueous monomer solution (2') gave off water vapor and swelled and foamed in various directions. After that, an obtained polymer shrunk to a size slightly larger than the bottom surface of the vat-type vessel. A hydrogel (2') was removed from the vat-type vessel after 3 minutes had passed since the commencement of the polymerization reaction. Note that this series of operations was carried out in an atmospheric air open state.

(Gel-Crushing Step)

Next, the hydrogel (2') obtained through the above-described polymerization reaction was cut such that a mass on a per-hydrogel basis was about 60 g, and was then subjected to gel-crushing with use of a meat chopper (HL-G22SN; plate pore diameter: 8.0 mm; manufactured by Remacom Co., Ltd.), so that a particulate hydrogel (2') was obtained. The hydrogel (2') was introduced into the meat chopper at a rate of about 360 g/min. The gel-crushing was carried out while deionized water having a temperature adjusted to 80° C. was being added to the meat chopper at a rate of 50 g/min simultaneously with the introduction of the hydrogel (2').

Immediately after that, the obtained particulate hydrogel (2') was crushed again with use of a meat chopper (HL-G22SN; plate pore diameter: 8.0 mm; manufactured by Remacom Co., Ltd.), so that a particulate hydrogel (2') was obtained. At the time of crushing the particulate hydrogel (2') again, no deionized water was not added to the meat chopper.

The particulate hydrogel (2') had D50 (mass average particle diameter) of 400 μm and had σig (logarithmic standard deviation of a particle size distribution) of 0.97.

(Drying Step)

Next, the particulate hydrogel (2') was spread onto a metal gauze with a mesh size of 300 μm and then placed in a hot air dryer. After that, the particulate hydrogel (2') was dried by passing hot air having a temperature of 190° C. over the particulate hydrogel (2') for 20 minutes. In this way, a dried polymer (2') was obtained. No undried material was found in the dried polymer (2').

(Classification Step)

Next, the dried polymer (2') was introduced into a roll mill (WML-type roll pulverizer; manufactured by Inoguchi Giken Ltd.) and pulverized. Thereafter, the dried polymer (2') thus pulverized was classified with use of two JIS standard sieves having respective mesh sizes of 850 μm and 150 μm. A dried polymer in the form of an agglomerate that had remained on the sieve having the mesh size of 850 μm was subjected to pulverization and classification which were repeated until the whole of such a dried polymer passed through the sieve having the mesh size of 850 μm. Obtained by this operation were a water-absorbing resin (2') having a non-uniformly pulverized shape before surface-crosslinking that had passed through the sieve having the mesh size of 850 μm and remained on the sieve having the mesh size of 150 μm and fine powder (2'-1) that had passed through the sieve having the mesh size of 150 μm.

(Surface-Crosslinking Step)

Next, to 100 parts by mass of the water-absorbing resin (2') before surface-crosslinking, an aqueous surface-crosslinking agent solution containing 0.3 parts by mass of ethylene carbonate, 0.5 parts by mass of propylene glycol, and 2.7 parts by mass of deionized water was added by spraying and mixed uniformly. After that, a mixture thus obtained was subjected to surface-crosslinking by carrying out heating treatment at 200° C. for 40 minutes. Then, the mixture was classified with use of two JIS standard sieves having respective mesh sizes of 850 μm and 150 μm. A mixture in the form of an agglomerate that had remained on the sieve having the mesh size of 850 μm was subjected to crushing of agglomeration and classification which were repeated until the whole of such a mixture passed through the sieve having the mesh size of 850 μm. Obtained by this operation were the water-absorbing resin (2') after surface-crosslinking that had passed through the sieve having the mesh size of 850 μm and remained on the sieve having the mesh size of 150 μm and fine powder (2'-2) that had passed through the sieve having the mesh size of 150 μm.

(Granulation Step)

Next, the fine powder (2'-1) and the fine powder (2'-2) were mixed in mass proportions of 17:3 (w:w), and a resulting mixture was considered to be fine powder (2'-3). The fine powder (2'-3) had D50 (mass average particle diameter) of 91 μm. Then, after 60 parts by mass of the fine powder (2'-3) was heated to 67° C., the fine powder (2'-3) was introduced into a food processor (MK-K48P; manufactured by Panasonic Corporation) that had been heated to 80° C. in an oven. 40 parts by mass of deionized water having a temperature adjusted to 82° C. was added to the fine powder (2'-3) over a period of 5 seconds while being stirred. After that, these substances were mixed for another 15 seconds so that a granulated gel (2'-3) was obtained.

(Granulated Gel Addition Step)

Next, after 2 minutes had passed since the commencement of the granulation, 80 parts by mass of the granulated gel (2'-3) was added to 360 parts by mass of particulate hydrogel (2') that had been prepared by carrying out the above-described operation again. Immediately after the addition, these substances were mixed for 10 seconds in a mortar mixer (manufactured by Nishinihonshikenki) that had been heated to 80° C., so that a mixed gel (2'-4) was obtained. Note that the temperature of the granulated gel (2'-3) and the temperature of the particulate hydrogel (2')

immediately before the granulated gel (2'-3) and the particulate hydrogel (2') were mixed in the mortar mixer were 70° C. and 55° C., respectively. Further, mixability of the granulated gel (2'-3) and the particulate hydrogel (2') in the mortar mixer was good.

(Drying Step)

Next, the mixed gel (2'-4) was spread onto a metal gauze with a mesh size of 300 μm and then placed in a hot air dryer. After that, the mixed gel (2'-4) was dried by passing hot air having a temperature of 190° C. over the mixed gel (2'-4) for 20 minutes. In this way, a dried polymer (2'-4) was obtained. No undried material was found in the dried polymer (2'-4).

(Classification Step)

Next, the dried polymer (2'-4) was introduced into a roll mill (WML-type roll pulverizer; manufactured by Inoguchi Giken Ltd.) and pulverized. Thereafter, the dried polymer (2'-4) thus pulverized was classified with use of two JIS standard sieves having respective mesh sizes of 850 μm and 150 μm. A dried polymer in the form of an agglomerate that had remained on the sieve having the mesh size of 850 μm was subjected to pulverization and classification which were repeated until the whole of such a dried polymer passed through the sieve having the mesh size of 850 μm. Obtained by this operation was a water-absorbing resin (2'-4) having a non-uniformly pulverized shape before surface-crosslinking that had passed through the sieve having the mesh size of 850 μm and remained on the sieve having the mesh size of 150 μm.

(Surface-Crosslinking Step)

Next, to 100 parts by mass of the water-absorbing resin (2'-4) before surface-crosslinking, an aqueous surface-crosslinking agent solution containing 0.3 parts by mass of ethylene carbonate, 0.5 parts by mass of propylene glycol, and 2.7 parts by mass of deionized water was added by spraying and mixed uniformly. After that, a mixture thus obtained was subjected to surface-crosslinking by carrying out heating treatment at 200° C. for 40 minutes.

Next, while the mixture was stirred and cooled, an aqueous additive solution containing 1 part by mass of a 27 mass % aqueous aluminum sulfate solution and 0.2 parts by mass of a 60 mass % aqueous sodium lactate solution was added to the mixture. After that, a mixture thus obtained was classified with use of two JIS standard sieves having respective mesh sizes of 850 μm and 150 μm. A mixture in the form of an agglomerate that had remained on the sieve having the mesh size of 850 μm was subjected to crushing of agglomeration and classification which were repeated until the whole of such a mixture passed through the sieve having the mesh size of 850 μm. Obtained by this operation was a water-absorbing resin (2'-4) after surface-crosslinking that had passed through the sieve having the mesh size of 850 μm and remained on the sieve having the mesh size of 150 μm. Physical properties of the water-absorbing resin (2'-4) after surface-crosslinking are shown in Table 2.

Comparative Example 3

(Step of Preparing Aqueous Monomer Solution)

Into a 2-liter polypropylene container were introduced 400.0 parts by mass of acrylic acid, 3.2 parts by mass of polyethyleneglycol diacrylate (average molecular weight: 523), 0.08 parts by mass of allyl methacrylate, and 0.04 parts by mass of IRGACURE (registered trademark) 819, and these substances were mixed. After that, 640.0 parts by mass of a 24.0 mass % aqueous sodium hydroxide solution was further introduced into the container in a stepwise manner.

These substances were mixed so that an aqueous monomer solution (3') having a liquid temperature of 40° C. was prepared.

(Polymerization Step)

Next, while the aqueous monomer solution (3') having the liquid temperature of 40° C. was stirred, 24.0 parts by mass of a 4 mass % aqueous sodium persulfate solution was added. Immediately after that, the aqueous monomer solution (3') was poured into a stainless steel vat-type vessel (with a bottom surface of 340 mm×340 mm and a height of 25 mm; inner surface: Teflon (registered trademark) coating) in an atmospheric air open state. Further, while the aqueous monomer solution (3') was being poured into the vat-type vessel, an ultraviolet ray was applied to the aqueous monomer solution (3'). Note that the vat-type vessel was heated with use of a hot plate (NEO HOTPLATE HI-1000; manufactured by Iuchi Seiei Do Ltd.) until a surface temperature reached 50° C.

Soon after the aqueous monomer solution (3') was poured into the vat-type container, a polymerization reaction commenced. After 1 minute had passed since the commencement of the polymerization reaction, the application of the ultraviolet ray was stopped. After 2 minutes had passed since the stop of the application of the ultraviolet ray, a hydrogel (3') was removed from the vat-type container. Note that this series of operations was carried out in an atmospheric air open state.

(Gel-Crushing Step)

Next, the hydrogel (3') obtained through the above-described polymerization reaction was cut such that a mass on a per-hydrogel basis was about 60 g, and was then subjected to gel-crushing with use of a meat chopper (HL-G22SN; plate pore diameter: 8.0 mm; manufactured by Remacom Co., Ltd.), so that a particulate hydrogel (3') was obtained. The hydrogel (3') was introduced into the meat chopper at a rate of about 360 g/min. The gel-crushing was carried out while deionized water having a temperature adjusted to 80° C. was being added to the meat chopper at a rate of 25 g/min simultaneously with the introduction of the hydrogel (3').

The particulate hydrogel (3') had D50 (mass average particle diameter) of 550 μm and had cig (logarithmic standard deviation of a particle size distribution) of 1.01.

(Drying Step)

Next, the particulate hydrogel (3') was spread onto a metal gauze with a mesh size of 300 μm and then placed in a hot air dryer. After that, the particulate hydrogel (3') was dried by letting hot air having a temperature of 180° C. through for 30 minutes. In this way, a dried polymer (3') was obtained. The hot air having a temperature of 180° C. was let through from below to above the metal gauze for first 15 minutes and then let through from above to below the metal gauze for remaining 15 minutes. No undried material was found in the dried polymer (3').

(Classification Step)

Next, the dried polymer (3') was introduced into a roll mill (WML-type roll pulverizer; manufactured by Inoguchi Giken Ltd.) and pulverized. Thereafter, the dried polymer (3') thus pulverized was classified with use of two JIS standard sieves having respective mesh sizes of 850 μm and 150 μm. Obtained by this operation were a water-absorbing resin (3') having a non-uniformly pulverized shape before surface-crosslinking that had passed through the sieve having the mesh size of 850 μm and remained on the sieve having the mesh size of 150 μm and fine powder (3'-1) that had passed through the sieve having the mesh size of 150 μm.

(Granulation Step)

Next, after 100 parts by mass of the fine powder (3'-1) was heated to 70° C., the fine powder (3'-1) was introduced into a Loedige mixer. 100 parts by mass of deionized water having a temperature adjusted to 70° C. was added to the fine powder (3'-1) while being stirred. These substances were mixed for approximately 1 minute so that a granulated gel (3'-1) was obtained.

(Granulated Gel Addition Step)

Next, after 2.5 minutes had passed since the commencement of the granulation, 80 parts by mass of the granulated gel (3'-1) was added to 320 parts by mass of the particulate hydrogel (3') that had been prepared by carrying out the above-described operation again. Immediately after the addition, these substances were mixed for 10 seconds in a mortar mixer (manufactured by Nishinihonshikenki) that had been heated to 80° C., so that a mixed gel (3'-2) was obtained. Note that the temperature of the granulated gel (3'-1) and the temperature of the particulate hydrogel (3') immediately before the granulated gel (3'-1) and the particulate hydrogel (3') were mixed in the mortar mixer were 55° C. and 52° C., respectively. Further, mixability of the granulated gel (3'-1) and the particulate hydrogel (3') in the mortar mixer was good.

(Drying Step)

Next, the mixed gel (3'-2) was spread onto a metal gauze with a mesh size of 300 μm and then placed in a hot air dryer. After that, the mixed gel (3'-2) was dried by passing hot air having a temperature of 180° C. over the mixed gel (3'-2) for 30 minutes. In this way, a dried polymer (3'-2) was obtained. The hot air having a temperature of 180° C. was let through from below to above the metal gauze for first 15 minutes and then let through from above to below the metal gauze for remaining 15 minutes. No undried material was found in the dried polymer (3'-2).

(Classification Step)

Next, the dried polymer (3'-2) was introduced into a roll mill (WML-type roll pulverizer; manufactured by Inoguchi Giken Ltd.) and pulverized. Thereafter, the dried polymer (3'-2) thus pulverized was classified with use of two JIS standard sieves having respective mesh sizes of 850 μm and 150 μm. Obtained by this operation was a water-absorbing resin (3'-2) having a non-uniformly pulverized shape before surface-crosslinking that had passed through the sieve having the mesh size of 850 μm and remained on the sieve having the mesh size of 150 μm.

(Surface-Crosslinking Step)

Next, to 100 parts by mass of the water-absorbing resin (3'-2) before surface-crosslinking, an aqueous surface-crosslinking agent solution containing 1.0 part by mass of ethylene carbonate and 4.0 parts by mass of deionized water was added by spraying and mixed uniformly. After that, a mixture thus obtained was subjected to surface-crosslinking by a heating treatment at 180° C. for 40 minutes. Then, the mixture was classified with use of two JIS standard sieves having respective mesh sizes of 850 μm and 150 μm. Obtained by this operation was a water-absorbing resin (3'-2) after surface-crosslinking that had passed through the sieve having the mesh size of 850 μm and remained on the sieve having the mesh size of 150 μm. Physical properties of the water-absorbing resin (3'-2) after surface-crosslinking are shown in Table 2.

Comparative Example 4

(Step of Preparing Aqueous Monomer Solution)

Into a 2-liter polypropylene container were introduced 400.0 parts by mass of acrylic acid, 3.2 parts by mass of polyethyleneglycol diacrylate (average molecular weight: 523), 0.4 parts by mass of hexanediol acrylate, and 0.04 parts by mass of IRGACURE (registered trademark) 819, and these substances were mixed. After that, 640.0 parts by mass of a 24.0 mass % aqueous sodium hydroxide solution was further introduced into the container in a stepwise manner. These substances were mixed so that an aqueous monomer solution (4') having a liquid temperature of 40° C. was prepared.

(Polymerization Step)

Next, while the aqueous monomer solution (4') having the liquid temperature of 40° C. was stirred, 24.0 parts by mass of a 4 mass % aqueous sodium persulfate solution was added. Immediately after that, the aqueous monomer solution (4') was poured into a stainless steel vat-type vessel (with a bottom surface of 340 mm×340 mm and a height of 25 mm; inner surface: Teflon (registered trademark) coating) in an atmospheric air open state. Further, while the aqueous monomer solution (4') was being poured into the vat-type vessel, an ultraviolet ray was applied to the aqueous monomer solution (4'). Note that the vat-type vessel was heated with use of a hot plate (NEO HOTPLATE HI-1000; manufactured by Iuchi Seiei Do Ltd.) until a surface temperature reached 50° C.

Soon after the aqueous monomer solution (4') was poured into the vat-type container, a polymerization reaction commenced. After 1 minute had passed since the commencement of the polymerization reaction, the application of the ultraviolet ray was stopped. After 2 minutes had passed since the stop of the application of the ultraviolet ray, a hydrogel (4') was removed from the vat-type container. Note that this series of operations was carried out in an atmospheric air open state.

(Gel-Crushing Step)

Next, the hydrogel (4') obtained through the above-described polymerization reaction was cut such that a mass on a per-hydrogel basis was about 60 g, and was then subjected to gel-crushing with use of a meat chopper (HL-G22SN; plate pore diameter: 8.0 mm; manufactured by Remacom Co., Ltd.), so that a particulate hydrogel (4') was obtained. The hydrogel (4') was introduced into the meat chopper at a rate of about 360 g/min. The gel-crushing was carried out while deionized water having a temperature adjusted to 80° C. was being added to the meat chopper at a rate of 25 g/min simultaneously with the introduction of the hydrogel (4').

The particulate hydrogel (4') had D50 (mass average particle diameter) of 540 μm and had σig (logarithmic standard deviation of a particle size distribution) of 1.04.

(Drying Step)

Next, the particulate hydrogel (4') was spread onto a metal gauze with a mesh size of 300 μm and then placed in a hot air dryer. After that, the particulate hydrogel (4') was dried by passing hot air having a temperature of 180° C. over the particulate hydrogel (4') for 30 minutes. In this way, a dried polymer (4') was obtained. The hot air having a temperature of 180° C. was let through from below to above the metal gauze for first 15 minutes and then let through from above to below the metal gauze for remaining 15 minutes. No undried material was found in the dried polymer (4').

(Classification Step)

Next, the dried polymer (4') was introduced into a roll mill (WML-type roll pulverizer; manufactured by Inoguchi Giken Ltd.) and pulverized. Thereafter, the dried polymer (4') thus pulverized was classified with use of two JIS standard sieves having respective mesh sizes of 850 μm and 150 μm. Obtained by this operation were a water-absorbing resin (4') having a non-uniformly pulverized shape before surface-crosslinking that had passed through the sieve having the mesh size of 850 μm and remained on the sieve having the mesh size of 150 μm and fine powder (4'-1) that had passed through the sieve having the mesh size of 150 μm.

(Granulation Step)

Next, after 100 parts by mass of the fine powder (4'-1) was heated to 70° C., the fine powder (4'-1) was introduced into a Loedige mixer. 100 parts by mass of deionized water having a temperature adjusted to 70° C. was added to the fine powder (4'-1) while being stirred. These substances were mixed for approximately 1 minute so that a granulated gel (4'-1) was obtained.

(Granulated Gel Addition Step)

Next, after 2.5 minutes had passed since the commencement of the granulation, 100 parts by mass of the granulated gel (4'-1) was added to 300 parts by mass of the particulate hydrogel (4') that had been prepared by carrying out the above-described operation again. Immediately after the addition, these substances were mixed for 10 seconds in a mortar mixer (manufactured by Nishinihonshikenki) that had been heated to 80° C., so that a mixed gel (4'-2) was obtained. Note that the temperature of the granulated gel (4'-1) and the temperature of the particulate hydrogel (4') immediately before the granulated gel (4'-1) and the particulate hydrogel (4') were mixed in the mortar mixer were 55° C. and 52° C., respectively. Further, mixability of the granulated gel (4'-1) and the particulate hydrogel (4') in the mortar mixer was good.

(Drying Step)

Next, the mixed gel (4'-2) was spread onto a metal gauze with a mesh size of 300 μm and then placed in a hot air dryer. After that, the mixed gel (4'-2) was dried by passing hot air having a temperature of 180° C. over the mixed gel (4'-2) for 30 minutes. In this way, a dried polymer (4'-2) was obtained. The hot air having a temperature of 180° C. was let through from below to above the metal gauze for first 15 minutes and then let through from above to below the metal gauze for remaining 15 minutes. No undried material was found in the dried polymer (4'-2).

(Classification Step)

Next, the dried polymer (4'-2) was introduced into a roll mill (WML-type roll pulverizer; manufactured by Inoguchi Giken Ltd.) and pulverized. Thereafter, the dried polymer (4'-2) thus pulverized was classified with use of two JIS standard sieves having respective mesh sizes of 850 μm and 150 μm. Obtained by this operation was a water-absorbing resin (4'-2) having a non-uniformly pulverized shape before surface-crosslinking that had passed through the sieve having the mesh size of 850 μm and remained on the sieve having the mesh size of 150 μm.

(Surface-Crosslinking Step)

Next, to 100 parts by mass of the water-absorbing resin (4'-2) before surface-crosslinking, an aqueous surface-crosslinking agent solution containing 0.5 part by mass of ethylene carbonate, 3.0 parts by mass of methanol, and 3.0 parts by mass of deionized water was added by spraying and mixed uniformly. After that, a mixture thus obtained was subjected to surface-crosslinking by a heating treatment at 180° C. for 40 minutes. Then, the mixture was classified with use of two JIS standard sieves having respective mesh sizes of 850 μm and 150 μm. Obtained by this operation was a water-absorbing resin (4'-2) after surface-crosslinking that had passed through the sieve having the mesh size of 850 μm and remained on the sieve having the mesh size of 150 μm. Physical properties of the water-absorbing resin (4'-2) after surface-crosslinking are shown in Table 2.

Comparative Example 5

(Step of Preparing Aqueous Monomer Solution)

Into a 2-liter polypropylene container, 11.0 parts by mass of a 0.5 mass % IRGACURE (registered trademark) 819 solution diluted with acrylic acid, 26.0 parts by mass of a 5.0 mass % polyethyleneglycol diacrylate (average molecular weight: 400) solution diluted with acrylic acid, 14.0 parts by mass of a 5.0 mass % trimethylolpropane triacrylate (ethoxylated TMPTA, TMP(EO)9TA, M-3190; manufactured by Miwon Specialty Chemical Co., Ltd.) solution diluted with acrylic acid, and 445.2 parts by mass of acrylic acid were introduced and mixed. After that, 800.0 parts by mass of a 24.0 mass % aqueous sodium hydroxide solution was further introduced into the container in a stepwise manner. These substances were mixed so that an aqueous monomer solution (5') was prepared. The neutralization rate of the acrylic acid in the aqueous monomer solution (5') was 70 mol %. Further, the liquid temperature of the aqueous monomer solution (5') thus obtained exceeded 50° C. due to heat of neutralization and heat of dissolution which were generated during the mixing.

(Polymerization Step)

Next, the aqueous monomer solution (5') was cooled while being stirred. At a point in time at which the liquid temperature reached 45° C., 30.0 parts by mass of a 5.0 mass % aqueous sodium hydrogen carbonate solution, an aqueous solution obtained by dissolving 1.6 parts by mass of aluminum sulfate in 28.0 parts by mass of a 5.0 mass % aqueous sodium hydrogen carbonate solution, and 60.0 parts by mass of a 1.0 mass % aqueous OFX-0193 (XIAMETER (registered trademark)) solution were added to and mixed with the aqueous monomer solution (5'). After a mixture thus obtained was stirred for about 2 seconds, the mixture was poured into a stainless steel vat-type vessel (with a bottom surface of 150 mm×150 mm and a height of 90 mm; inner surface: Teflon (registered trademark) coating) in an atmospheric air open state. Further, while the mixture was being poured into the vat-type vessel, an ultraviolet ray was applied to the mixture. Note that the vat-type vessel was heated until a surface temperature reached 80° C.

After the mixture was poured into the vat-type vessel, a polymerization reaction commenced after a lapse of approximately 30 seconds. After 2 minutes had passed since the commencement of the polymerization reaction, the application of the ultraviolet ray was stopped, and a hydrogel (5') was removed from the vat-type container. Note that this series of operations was carried out in an atmospheric air open state.

(Gel-Crushing Step)

Next, the hydrogel (5') obtained through the above-described polymerization reaction was cut such that a mass on a per-hydrogel basis was about 60 g, and was then subjected to gel-crushing with use of a meat chopper (HL-G22SN; plate pore diameter: 8.0 mm; manufactured by Remacom Co., Ltd.), so that a particulate hydrogel (5') was obtained. The hydrogel (5') was introduced into the meat chopper at a rate of about 360 g/min. The gel-crushing was carried out while deionized water having a temperature adjusted to 80° C. was being added to the meat chopper at a rate of 50 g/min simultaneously with the introduction of the hydrogel (5').

The particulate hydrogel (5') had D50 (mass average particle diameter) of 910 μm and had σζ (logarithmic standard deviation of a particle size distribution) of 1.02.

(Drying Step)

Next, the particulate hydrogel (5') was spread onto a metal gauze with a mesh size of 300 μm and then placed in a hot air dryer. After that, the particulate hydrogel (5') was dried by passing hot air having a temperature of 180° C. over the particulate hydrogel (5') for 30 minutes. In this way, a dried polymer (5') was obtained. The hot air having a temperature of 180° C. was let through from below to above the metal gauze for first 15 minutes and then let through from above to below the metal gauze for remaining 15 minutes. No undried material was found in the dried polymer (5').

(Classification Step)

Next, the dried polymer (5') was introduced into a roll mill (WML-type roll pulverizer; manufactured by Inoguchi Giken Ltd.) and pulverized. Thereafter, the dried polymer (5') thus pulverized was classified with use of two JIS standard sieves having respective mesh sizes of 850 μm and 150 μm. Obtained by this operation was a water-absorbing resin (5') having a non-uniformly pulverized shape before surface-crosslinking that had passed through the sieve having the mesh size of 850 μm and remained on the sieve having the mesh size of 150 μm.

(Surface-Crosslinking Step)

Next, to 100 parts by mass of the water-absorbing resin (5') before surface-crosslinking, an aqueous surface-crosslinking agent solution containing 0.4 parts by mass of ethylene carbonate, 3.0 parts by mass of methanol, 3.0 parts by mass of deionized water, and 0.5 parts by mass of Aerosil 200 (manufactured by EVONIK) was added by spraying and mixed uniformly. After that, a mixture thus obtained was subjected to surface-crosslinking by a heating treatment at 190° C. for 30 minutes. Then, the mixture was classified with use of two JIS standard sieves having respective mesh sizes of 850 μm and 150 μm. Obtained by this operation was a water-absorbing resin (5') after surface-crosslinking that had passed through the sieve having the mesh size of 850 μm and remained on the sieve having the mesh size of 150 μm. Physical properties of the water-absorbing resin (5') after surface-crosslinking are shown in Table 2.

Comparative Example 6

(Step of Preparing Aqueous Monomer Solution)

Into a 1-liter polypropylene container were introduced 291.0 parts by mass of acrylic acid, 247.0 parts by mass of a 48.5 mass % aqueous sodium hydroxide solution, 0.4 parts by mass of polyethyleneglycol diacrylate (average molecular weight: 523), 1.8 parts by mass of a 1.0 mass % aqueous diethylenetriamine pentaacetic acid/pentasodium solution, 3.6 parts by mass of a 1.0 mass % IRGACURE (registered trademark) 814 solution diluted with acrylic acid, and 255.0 parts by mass of deionized water. These substances were mixed so that an aqueous monomer solution (6') was prepared. The liquid temperature of the aqueous monomer solution (6') exceeded 90° C. due to heat of neutralization and heat of dissolution which were generated during the mixing.

(Polymerization Step)

Next, while the aqueous monomer solution (6') was stirred with the liquid temperature thereof maintained at 90° C., 1.8 parts by mass of a 3.0 mass % aqueous sodium persulfate solution was added. Immediately after that, the aqueous monomer solution (6') was poured into a stainless steel vat-type vessel (with a bottom surface of 340 mm×340 mm and a height of 25 mm; inner surface: Teflon (registered trademark) coating) in an atmospheric air open state. Further, while the aqueous monomer solution (6') was being poured into the vat-type vessel, an ultraviolet ray was applied to the aqueous monomer solution (6'). Note that the vat-type vessel was heated with use of a hot plate (NEO HOTPLATE HI-1000; manufactured by Iuchi Seiei Do Ltd.) until a surface temperature reached 50° C.

Soon after the aqueous monomer solution (6') was poured into the vat-type container, a polymerization reaction commenced. In this polymerization reaction, polymerization of the aqueous monomer solution (6') proceeded while the aqueous monomer solution (6') gave off water vapor and swelled and foamed in various directions. After that, an obtained polymer shrunk to a size slightly larger than the bottom surface of the vat-type vessel. After 3 minutes had passed since the commencement of the polymerization reaction, the application of the ultraviolet ray was stopped, and a hydrogel (6') was removed from the vat-type container. Note that this series of operations was carried out in an atmospheric air open state.

(Gel-Crushing Step)

Next, the hydrogel (6') obtained through the above-described polymerization reaction was cut such that a mass on a per-hydrogel basis was about 60 g, and was then subjected to gel-crushing with use of a meat chopper (HL-G22SN; plate pore diameter: 6.0 mm; manufactured by Remacom Co., Ltd.), so that a particulate hydrogel (6') was obtained. The hydrogel (6') was introduced into the meat chopper at a rate of about 360 g/min. The gel-crushing was carried out while deionized water having a temperature adjusted to 90° C. was being added to the meat chopper at a rate of 50 g/min simultaneously with the introduction of the hydrogel (6').

The particulate hydrogel (6') had D50 (mass average particle diameter) of 750 μm and had cig (logarithmic standard deviation of a particle size distribution) of 1.01.

(Drying Step)

Next, the particulate hydrogel (6') was spread onto a metal gauze with a mesh size of 300 μm and then placed in a hot air dryer. After that, the particulate hydrogel (6') was dried by passing hot air having a temperature of 180° C. over the particulate hydrogel (6') for 30 minutes. In this way, a dried polymer (6') was obtained. No undried material was found in the dried polymer (6').

(Classification Step)

Next, the dried polymer (6') was introduced into a roll mill (WML-type roll pulverizer; manufactured by Inoguchi Giken Ltd.) and pulverized. Thereafter, the dried polymer (6') thus pulverized was classified with use of two JIS standard sieves having respective mesh sizes of 850 μm and 150 μm. Obtained by this operation were a water-absorbing resin (6') having a non-uniformly pulverized shape before surface-crosslinking that had passed through the sieve having the mesh size of 850 μm and remained on the sieve having the mesh size of 150 μm and fine powder (6'-1) that had passed through the sieve having the mesh size of 150 μm.

(Granulation Step)

Next, 100 parts by mass of the fine powder (6'-1) was introduced into a Loedige mixer. 100 parts by mass of deionized water having a temperature adjusted to 60° C. was added to the fine powder (6'-1) while being stirred. These substances were mixed for approximately 1 minute so that a granulated gel (6'-1) was obtained.

(Drying Step)

Next, the granulated gel (6'-1) was spread onto a metal gauze with a mesh size of 300 μm and then placed in a hot air dryer. After that, the granulated gel (6'-1) was dried by passing hot air having a temperature of 170° C. over the granulated gel (6'-1) for 30 minutes. In this way, a dried polymer (6'-1) was obtained. No undried material was found in the dried polymer (6'-1).

(Classification Step)

Next, the dried polymer (6'-1) was introduced into a roll mill (WML-type roll pulverizer; manufactured by Inoguchi Giken Ltd.) and pulverized. Thereafter, the dried polymer (6'-1) thus pulverized was classified with use of two JIS standard sieves having respective mesh sizes of 850 μm and 150 μm. Obtained by this operation was a water-absorbing resin (6'-1) having a non-uniformly pulverized shape before surface-crosslinking that had passed through the sieve having the mesh size of 850 μm and remained on the sieve having the mesh size of 150 μm.

Next, 80 parts by mass of the water-absorbing resin (6') before surface-crosslinking and 20 parts by mass of the water-absorbing resin (6'-1) before surface-crosslinking were mixed, so that a water-absorbing resin (6'-2) before surface-crosslinking was obtained.

(Surface-Crosslinking Step)

Next, to 100 parts by mass of the water-absorbing resin (6'-2) before surface-crosslinking, an aqueous surface-cross-linking agent solution containing 3.3 parts by mass of cationic colloidal silica (trade name: Klebosol 30CAL25 30% aqueous solution; manufactured by AZ Electronic Materials), 0.5 parts by mass of 1,3-propanediol, 1.0 part by mass of methanol, and 3.0 parts by mass of deionized water was added by spraying and mixed uniformly. After that, a mixture thus obtained was subjected to surface-crosslinking by a heating treatment at 200° C. for 40 minutes. Then, the mixture was classified with use of two JIS standard sieves having respective mesh sizes of 850 μm and 150 μm. Obtained by this operation was a water-absorbing resin (6'-2) after surface-crosslinking that had passed through the sieve having the mesh size of 850 μm and remained on the sieve having the mesh size of 150 μm. Physical properties of the water-absorbing resin (6'-2) after surface-crosslinking are shown in Table 2.

Various physical properties of the water-absorbing resins after surface-crosslinking obtained in Examples 1 to 4 and Comparative Examples 1 to 6 were measured. The following description shows a measurement method. Further, Table 2 shows the measurement results.

<Measurement Method>

[CRC (Absorption Capacity without Load)]

A CRC (absorption capacity without load) of the water-absorbing resin in accordance with an embodiment of the present invention was measured in conformity with an EDANA method (WSP 241.3(10)). Specifically, the CRC (absorption capacity without load) (unit: g/g) was measured after 0.2 g of water-absorbing resin contained in a nonwoven fabric bag was immersed in a large excess of a 0.9 mass % aqueous sodium chloride solution for 30 minutes so as to be allowed to freely swell, and then the water-absorbing resin was drained with use of a centrifuge (centrifugal force: 250 G).

[AAP (Absorption Capacity Under Load)]

An AAP (absorption capacity under load) of the water-absorbing resin in accordance with an embodiment of the present invention was measured in conformity with an EDANA method (WSP 242.3(10)). Note, however, that in the present invention, the load used during measurements was changed to 4.83 kPa (49 g/cm², 0.7 psi). Specifically, the AAP (absorption capacity under load) (unit: g/g) was measured after 0.9 g of water-absorbing resin was allowed to swell for 1 hour under load of 4.83 kPa (49 g/cm², 0.7 psi) with use of a large excess of a 0.9 mass % aqueous sodium chloride solution. That is, in the present specification, all AAP (absorption capacity under load) measurements are values measured under a load of 4.83 kPa.

[SFC (Saline Flow Conductivity)]

A saline flow conductivity (SFC) (unit: ×$10^{-7}$ cm³·sec/g) of the water-absorbing resin in accordance with an embodiment of the present invention was measured in conformity with a measurement method disclosed in U.S. Pat. No. 5,669,894.

[Solid Content]

The solid content of the water-absorbing resin in accordance with an embodiment of the present invention was calculated with use of a moisture content measured in conformity with an EDANA method (WSP 230.3(10)). Note that, for the present invention, out of the measurement conditions defined in WSP 230.3(10), the amount of water-absorbing resin (sample) was changed to 1.0 g, and the drying temperature was changed to 180° C. A value obtained by calculation of "100-moisture content (mass %)" was considered to be the solid content (unit: mass %) of the water-absorbing resin.

Further, the solid content of the particulate hydrogel or the granulated gel was also similarly calculated with use of a moisture content measured in conformity with an EDANA method (WSP 230.3(10)). Note that, for the present invention, out of the measurement conditions defined in WSP 230.3(10), the amount of particulate hydrogel or granulated gel (sample) was changed to 2.0 g, and the drying temperature was changed to 180° C. A value obtained by calculation of "100-moisture content (mass %)" was considered to be the solid content (unit: mass %) of the particulate hydrogel or the granulated gel.

Further, the solid content of the dried polymer in the form of a block was calculated with use of a moisture content measured in conformity with an EDANA method (WSP 230.3(10)) as in the above-described measurement method for the solid content of the water-absorbing resin, after samples (water-absorbing resin) were collected from certain locations in the drying step and were pulverized until the samples had a particle diameter of 5 mm or less. A value obtained by calculation of "100-moisture content (mass %)" was considered to be the solid content (unit: mass %) of the dried polymer in the form of a block. Note that the solid content of the dried polymer in the form of a block was an average of values which were obtained from the samples collected from certain five locations in the drying step.

[D50 (Mass Average Particle Diameter)]

D50 (mass average particle diameter) (unit: μm) of the water-absorbing resin in accordance with an embodiment of the present invention was measured in conformity with a measurement method described in "(3) Mass-Average Particle Diameter (D50) and Logarithmic Standard Deviation (σ) of Particle Diameter Distribution", which is disclosed in U.S. Pat. No. 7,638,570.

[D50 (Mass Average Particle Diameter) of Particulate Hydrogel]

The mass average particle diameter (D50) of the pulverized particulate hydrogel in terms of solid content was measured. 20 g of the particulate hydrogel (solid content: a mass %) having a temperature of 20° C. to 25° C. was added to 500 g of a 20 mass % aqueous sodium chloride solution (hereinafter referred to as "EMAL aqueous solution") containing a 0.08 mass % EMAL 20° C. (surfactant; manufactured by Kao Corporation), so that a dispersion liquid was obtained. The dispersion liquid was then stirred with use of a stirrer tip having a length of 50 mm and a diameter of 7 mm at 300 rpm for 1 hour (with use of a cylindrical polypropylene container having a height of 21 cm and a diameter of 8 cm (capacity: approximately 1.14 L)).

After the stirring was finished, the resultant dispersion liquid was introduced into the center of a set of JIS standard sieves (having a diameter of 21 cm and having respective mesh sizes of 8 mm, 4 mm, 2 mm, 1 mm, 0.60 mm, 0.30 mm, 0.15 mm, and 0.075 mm) which were placed on a rotary table in such a manner as to be stacked on top of each other. After the entire particulate hydrogel was washed out onto the sieves with use of 100 g of an EMAL aqueous solution, the particulate hydrogel was classified by uniformly spraying 6000 g of an EMAL aqueous solution onto the sieves from 30 cm above with use of a shower (with 72 holes, flow rate: 6.0 L/min) in a manner such that the spraying area (50 cm$^2$) entirely covered the sieve, while rotating the sieve by hand (20 rpm). The particulate hydrogel, which had been subjected to the classification, on the first sieve from the top was drained for approximately 2 minutes, and was then weighed. For the second sieve from the top and the subsequent sieves, classification was carried out by the same operation. After the draining, the particulate hydrogel remaining on each of the sieves was weighed.

From the mass of the particulate hydrogel remaining on each sieve, a mass percentage X (unit: mass %) in the entire particulate hydrogel was calculated by use of Formula (1) below. A mesh size R(a) (unit: mm) of the sieve used for the particulate hydrogel remaining on the sieve and having a solid content of a mass % was calculated in accordance with Formula (2) below. X and R(a) of the particulate hydrogel remaining on each of the sieves were plotted on a logarithmic probability paper, so that a graph (particle size distribution) showing a relationship between a cumulative weight ratio of X and R(a) was made. From this graph, a particle diameter at which a residual percentage corresponds to 50 mass % was read as the mass average particle diameter (D50) of the particulate hydrogel.

$$X=(w/W)\times100 \qquad \text{Formula (1)}$$

$$R(\alpha)=(20/W)^{1/3}\times r \qquad \text{Formula (2)}$$

Note here that X, w, W, R(α), and r mean the following values.

X represents a percentage by mass (unit: mass %) of a particulate hydrogel remaining on each sieve after classification and draining.

w represents a mass (unit: g) of each particulate hydrogel remaining on each sieve after classification and draining.

W represents a total mass (unit: g) of particulate hydrogels remaining on the respective sieves after classification and draining.

R(α) represents the mesh size (unit: mm; calculated value) of a sieve used for classification of a particulate hydrogel on the assumption that the particulate hydrogel has a solid content of a mass %.

r represents a mesh size (unit: mm; measured value) of a JIS standard sieve used for classification of a particulate hydrogel that has been swollen in a 20 mass % aqueous sodium chloride solution containing a 0.08 mass % EMAL 20C (surfactant; manufactured by Kao Corporation).

[σζ (logarithmic standard deviation of particle size distribution)]

σζ (logarithmic standard deviation of particle size distribution) (unit: none) of the water-absorbing resin in accordance with an embodiment of the present invention was measured in conformity with a measurement method described in "(3) Mass-Average Particle Diameter (D50) and Logarithmic Standard Deviation (σζ) of Particle Diameter Distribution", which is disclosed in U.S. Pat. No. 7,638,570.

On the other hand, σζ (logarithmic standard deviation of particle size distribution) of a particulate hydrogel was measured in the following manner.

That is, mass % of the particulate hydrogel remaining on each of the sieves was calculated by the same method as the method employed for D50 (mass average particle diameter) of the particulate hydrogel, and the particle size distribution of the particulate hydrogel was plotted on a logarithmic probability paper. The particle diameter at which the cumulative oversize % R is 84.1 mass % (referred to as "X1") and the particle diameter at which the cumulative oversize % R is 15.9 mass % (referred to as "X2") were found from the above plot, and σζ (logarithmic standard deviation of particle size distribution) was found based on Formula (3) below.

$$\sigma\zeta=0.5\times\ln(X2/X1) \qquad \text{Formula (3)}$$

A σζ having a smaller value means a narrower particle size distribution.

[5-Mm Gel Thickness Reach Time]

The 5-mm gel thickness reach time (unit: second) of the water-absorbing resin in accordance with the present invention was measured by calculating a vertical movement distance of a weight at the measurement of the AAP (absorption capacity under load) under a pressurization condition changed to 4.83 kPa (49 g/cm$^2$, 0.7 psi), with use of a laser displacement meter manufactured by Keyence Corporation (amplifier unit: IL-1000; sensor head: IL-S100; power supply unit: KZ-U3), a data logger (manufactured by GRAPHTEC Corporation; midiLOGGER GL220), and Microsoft Excel.

The measurement was carried out in a room having a temperature adjusted to 23.0° C.±0.5° C. and having a humidity adjusted to between 35% and 50%. Further, for the measurement, a 0.9 mass % aqueous sodium chloride solution having a temperature adjusted to 23° C.±0.5° C. was used.

Figure 2:
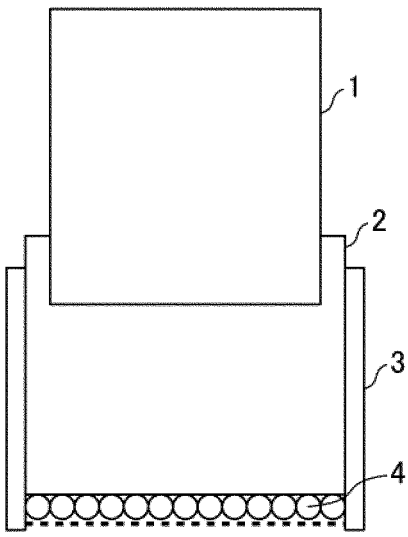
FIG. 2 is a view for explaining the configuration of a cell set A used at the measurements of a 5-mm gel thickness reach time, gel expansion force, and gel expansion speed of the water-absorbing resin in accordance with an embodiment of the present invention.

A specific measurement method is as follows. As illustrated in FIG. 2, first, a cylinder 3, a piston 2, and a weight 1 used at the measurement of the AAP under a pressurization condition changed to 4.83 kPa (49 g/cm$^2$, 0.7 psi) were prepared, 0.9 g of water-absorbing resin was placed in the cylinder 3, and the piston 2 was inserted into the cylinder 3 in which the water-absorbing resin had been placed. At this time, care was taken not to cause the water-absorbing resin to be caught between an inner wall of the cylinder 3 and the piston 2. Then, the weight 1 was placed on the piston 2. Note that the weight 1 used was shaped in a cylinder and had a flat upper surface. The cylinder 3 had a bottom surface in a mesh-like form. Hereinafter, a set group consisting of the water-absorbing resin, the cylinder 3, the piston 2, and the weight 1, which were prepared in the above-described step, is referred to as cell set A.

Figure 3:
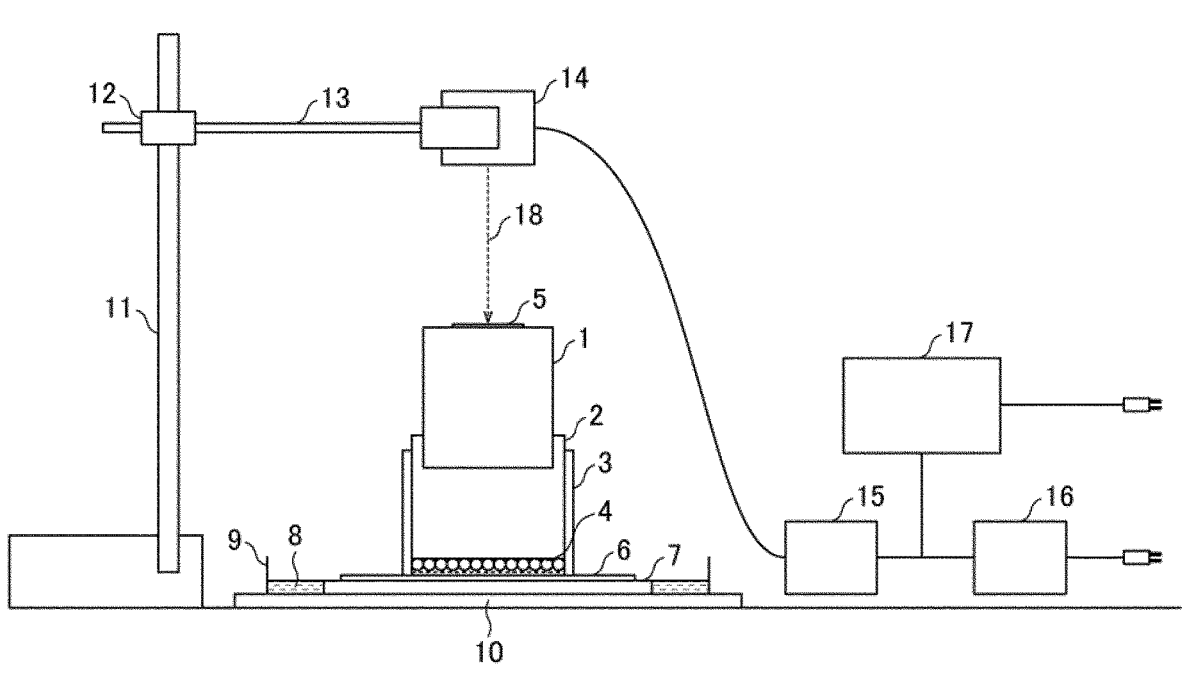
FIG. 3 is a view for explaining a method for measuring the 5-mm gel thickness reach time of the water-absorbing resin in accordance with an embodiment of the present invention.

Next, as illustrated in FIG. 3, a surface heater 10 set at 23° C. was placed on a horizontal experimental table, a SUS tray 9 used at the measurement of the AAP was placed on the surface heater 10, a glass filter 7 used at the measurement of the AAP was placed in the central part of the SUS tray 9 such that a surface of the glass filter 7 with little unevenness faced upwards, and a 0.9 mass % aqueous sodium chloride solution 8 was introduced into the SUS tray 9 so as to be at the same level as the height of an upper surface of the glass filter 7. At this time, care was taken to prevent air bubbles from entering the glass filter. Next, a paper filter 6 used at the measurement of the AAP was placed in the central part of the glass filter 7 such that a surface of the paper filter 6 with little unevenness faced upwards.

Figure 4:
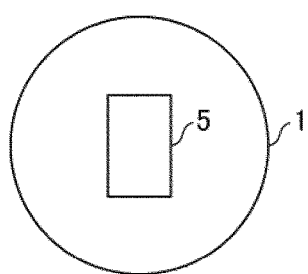
FIG. 4 is a view illustrating a position at which a white vinyl tape is affixed to an upper surface of a weight in the cell set A.

Further, to measure vertical position information of the weight 1 when the water-absorbing resin was swollen, a laser displacement meter manufactured by Keyence Corporation (amplifier unit 15: IL-1000; sensor head 14: IL-S100; power supply unit 16: KZ-U3) was installed. Note that the sensor head 14 is connected to the power supply unit 16 via the amplifier unit 15. Further, the sensor head 14 is supported by a clamp 13 which is attached to an upper part of the stand 11 via a muff 12. The sensor head 14 was installed so that, when the cell set A was placed in the central part of the paper filter 6, a laser to be emitted from the sensor head 14 was emitted vertically to an upper surface of the weight 1 in the cell set A, specifically in an emission direction indicated by an arrow 18. Further, a white vinyl tape 5 (product name: De-Lead Type Vinyl Tape, part number: 21-10W; manufactured by Nitto Denko Corporation) was affixed to the upper surface of the weight 1 in a portion where the laser was to be emitted, so that the emitted laser was properly reflected. A state in which the vinyl tape was affixed to the upper surface of the weight 1 is illustrated in a plan view of FIG. 4. This made it possible to measure the vertical position information (numerical data) of the weight 1. The position information of the weight 1 measured by the sensor head 14 was transmitted to a data logger (manufactured by GRAPHTEC Corporation; midiLOGGER GL220) 17 and was stored in the data logger 17. Note that the data logger 17 was connected between the amplifier unit 15 and the power supply unit 16 and was set so that the position information of the weight 1 could be continuously stored at intervals of 1 second.

In the above-described measurement environment, a time when the cell set A was placed in the central part of the paper filter was considered to be a start of measurement, and the measurement of the position information of the weight 1 by the laser deformation meter was started simultaneously with the start. After 1 hour had passed since the start of the measurement, the measurement of the position information of the weight 1 by the laser deformation meter was finished. FIG. 3 illustrates a measurement state at the stage where the measurement was started by placing the cell set A on the paper filter.

The position information of the weight 1 obtained by the measurement was extracted from the data logger 17 and was subjected to the following analysis on Microsoft Excel. First, in a period of time until after 10 seconds had passed since the start of swelling, a time at which the weight 1 sunk down to the lowest level was considered to be a "time point at 0-mm gel thickness". After the "time point at 0-mm gel thickness", the weight is supposed to be pushed up in the vertical direction by swelling of the water-absorbing resin. Thus, an absolute value of a difference between a numerical value of the position information at the "time point at 0-mm gel thickness" and a numerical value of the position information measured after the "time point at 0-mm gel thickness" indicates a distance a (gel thickness of a mm) by which the swollen water-absorbing resin pushes up the weight 1 in the vertical direction. This distance a was calculated for each elapsed time of measurement, and an amount of time required until the distance (calculated with use of Microsoft Excel) reached 5 mm (amount of time elapsed from the time point at 0-mm gel thickness to a time point at 5-mm gel thickness) was considered to be a "5-mm gel thickness reach time".

Note that the "5-mm gel thickness reach time" in the present invention was an average value of results of the measurement which was carried out twice with use of the same sample (water-absorbing resin).

[Gel Expansion Force, Gel Expansion Speed]

The gel expansion force (unit: N) and gel expansion speed (unit: none) of the water-absorbing resin in accordance with an embodiment of the present invention were found by carrying out, with use of Microsoft Excel, an analysis of numerical data obtained by measuring, with use of a tensile tester AUTOGRAPH (AG-1kNX; manufactured by Shimadzu Corporation) and operation software (TRAPEZIUM X), a force of pushing up the piston and the weight in the vertical direction when the water-absorbing resin having been swollen to "5-mm gel thickness" was further swollen at the measurement of the AAP (absorption capacity under load) under a pressurization condition changed to 4.83 kPa (49 g/cm$^2$, 0.7 psi).

A specific measurement method is as follows. As illustrated in FIG. 2, first, the cylinder 3, the piston 2, and the weight 1 used at the measurement of the AAP under a pressurization condition changed to 4.83 kPa (49 g/cm$^2$, 0.7 psi) were prepared, 0.9 g of water-absorbing resin was placed in the cylinder 3, and the piston 2 was inserted into the cylinder 3 in which the water-absorbing resin had been placed. At this time, care was taken not to cause the water-absorbing resin to be caught between the inner wall of the cylinder 3 and the piston 2. Then, the weight 1 was placed on the piston 2. Note that the weight 1 used was shaped in a cylinder and had a flat upper surface. Hereinafter, a set group consisting of the water-absorbing resin, the cylinder 3, the piston 2, and the weight 1, which were prepared in the above-described step, is referred to as cell set A. Note that the operations so far were carried out in a room having a temperature adjusted to 23° C.±0.5° C. and having a humidity adjusted to be between 35% and 50%, and the subsequent operations were carried out in a room having a temperature adjusted to 23° C.±0.5° C. and having a humidity adjusted to between 35% and 60%.

Figure 5:
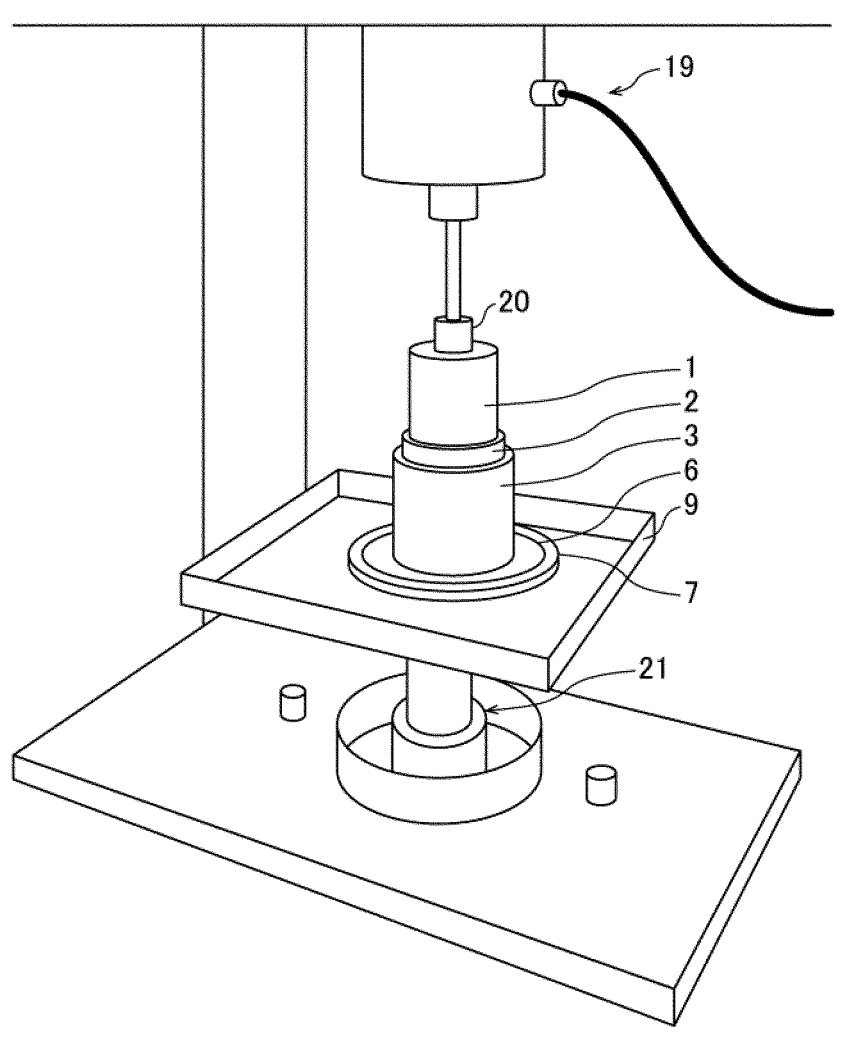
FIG. 5 is a perspective view for explaining a method for measuring the gel expansion force and gel expansion speed of the water-absorbing resin in accordance with an embodiment of the present invention, and illustrating a state in which a load cell, a compression jig, and an AAP measuring instrument are installed on an autograph.

On the AUTOGRAPH (AG-1kNX; manufactured by Shimadzu Corporation), a load cell 19 (SLBL-50N; manufactured by Shimadzu Corporation) and a compression jig (upper pressure plate 20: Φ20 S346-51687-08; lower pressure plate 21: Φ118 S346-51687-12) were installed, and further, an AAP measuring instrument was placed on the lower pressure plate 21 in a state in which enough space was left between the upper pressure plate 20 and the lower pressure plate 21. FIG. 5 illustrates a state in which the load cell 19, the compression jig, and the AAP measuring instrument are installed on an autograph 30. Here, the phrase "AAP measuring instrument was placed on the lower pressure plate 21" refers to a state in which: the SUS tray 9 used at the measurement of the AAP was placed on the lower pressure plate 21 such that a center of the lower pressure plate 21 and a center of the SUS tray 9 coincide with each other; the glass filter 7 used at the measurement of the AAP was placed in the central part of the SUS tray 9 such that a surface of the glass filter 7 with little unevenness faced upwards; the paper filter 6 used at the measurement of the AAP was placed in the central part of the glass filter 7 such that a surface of the paper filter 6 with little unevenness faced upwards; and the cell set A was placed in the central part of the paper filter 6.

Further, on the operation software (TRAPEZIUM X), a setting was made, as a measurement condition, such that the upper pressure plate 20 installed at a predetermined position automatically lowers at a speed of 0.1 mm per second from a time point at which the measurement was started, and was then fixed at such a position that the upper pressure plate 20 came into contact with the upper surface of the weight 1 in the cell set A and at a time point at which the upper pressure plate 20 came into contact with the upper surface of the weight 1 in the cell set A. In addition, the setting was made such that the force of the swollen water-absorbing resin pushing up the piston 2 and the weight 1 was continuously read at intervals of 0.5 second via the fixed upper pressure plate 20. Specifically, on the operation software, "Create New Test Condition" was clicked, and a test condition was set as shown below.

"System"
    Test mode: single
    Test type: compression
    Load cell polarity: compression
    Movement direction: down
    Unit: SI
    Format: round-off
"Sensor"
(Test force)
    Channel: test force amplifier
    Name: test force
    Full scale: 50 N
    Limit: 40 N (checked)
    Stress name: stress
    Use true stress: unchecked
(Stroke)
    Name: stroke
    Limit: 500 mm (checked)
    Stroke (strain) name: stroke (strain)
    Use true strain: unchecked
    Perform deflection correction: unchecked
(Displacement Meter)
    Displacement meter 1
    Channel: none
(Width Meter)
    Channel: none
(Other Item)
    Other item 1
    Channel: none
"Test Control"
    Elongation origin: from the beginning
Area 1
    Control operation: load
    Control: stroke
    V1: 0.100000 mm/sec
    Setting between area 1 and area 2
    Target value channel
    Test force
    0.01 N
Area 2
    Control operation: hold
    Control: stroke
    Setting between area 2 and area 3
    Hold time
    6000 sec
Area 3
    Control operation: OFF
(End Condition)
    Break setting: all unchecked
    Operation after test: stop
    Break detection start point: 0.035%

(Sampling)
    Time: 0.5 sec
(Preliminary Load)
    All unchecked
"Test Piece"
    Material: plastic
    Shape: flat plate
    Number of batches: 1
    Number of sub-batches: 1
    Dimensional unit: mm
"Data Processing Item"
    No particular setting is needed
"Graph"
    Desired setting is possible
"Report"
    Desired setting is possible
    Next, on the operation software, "Select Condition and Execute Test" was clicked, so that the above-described test condition was selected, and a test execution screen was then opened. Further, "Test Force" was right-clicked on the screen, calibration was performed, and an indication of "Test Force" on the screen was set to less than 0.02 N.
    A procedure by which the method for measuring the gel expansion force and the gel expansion speed of the water-absorbing resin was carried out in the above-described measurement environment will be described with reference to FIG. 6.
    First, as illustrated in (a) of FIG. 6, the upper pressure plate 20 was manually lowered until the upper pressure plate 20 came into contact with the upper surface of the weight 1 in the cell set A, and the position of the upper pressure plate 20 in contact with the upper surface of the weight 1 was considered to be 0 mm. Specifically, at the position of the upper pressure plate 20, "Stroke" was right-clicked on the test execution screen, and zero reset was performed. Note that the word "manually" as used herein refers to performing an operation using buttons and dials of a smart controller (manufactured by Shimadzu Corporation) connected to the AUTOGRAPH. Further, the word "manually" also refers hereinafter to a similar operation. In addition, when the weight 1 and the upper pressure plate come into contact with each other, a force of the weight 1 pushing up the upper pressure plate 20 is slightly generated. Thus, an increase in the "test force" is confirmed on the test execution screen. Here, a time point at which the "test force" became 0.1 N or more and less than 0.5 N due to the increase in the "test force" was defined as a contact. Next, as illustrated in (b) of FIG. 6, a position of the upper pressure plate 20 manually raised by 7.5 mm was considered to be "measurement start position". The distance of 7.5 mm by which the upper pressure plate 20 was raised is a sum of estimated values based on the estimation that, at the measurement of the gel expansion force, the weight 1 is raised by 5.0 mm due to swelling of the water-absorbing resin (equivalent to the 5-mm gel thickness) and the estimation that the distance by which the upper pressure plate 20 lowers is 2.5 mm when the upper pressure plate 20 lowers at the start of the test and comes into contact with the weight 1 at the time point at which the gel thickness is 5 mm. Since the time point at which the gel thickness is 5 mm is measured in advance, and the start of the test is set to 25 seconds before that time point, it is possible to assume a distance by which the upper pressure plate 20 lowers (in the above case, since a speed at which the upper pressure plate 20 lowers is set to 0.1 mm per second, the distance can be set to 0.1 mm per second×25 seconds=2.5 mm).

Figure 6:
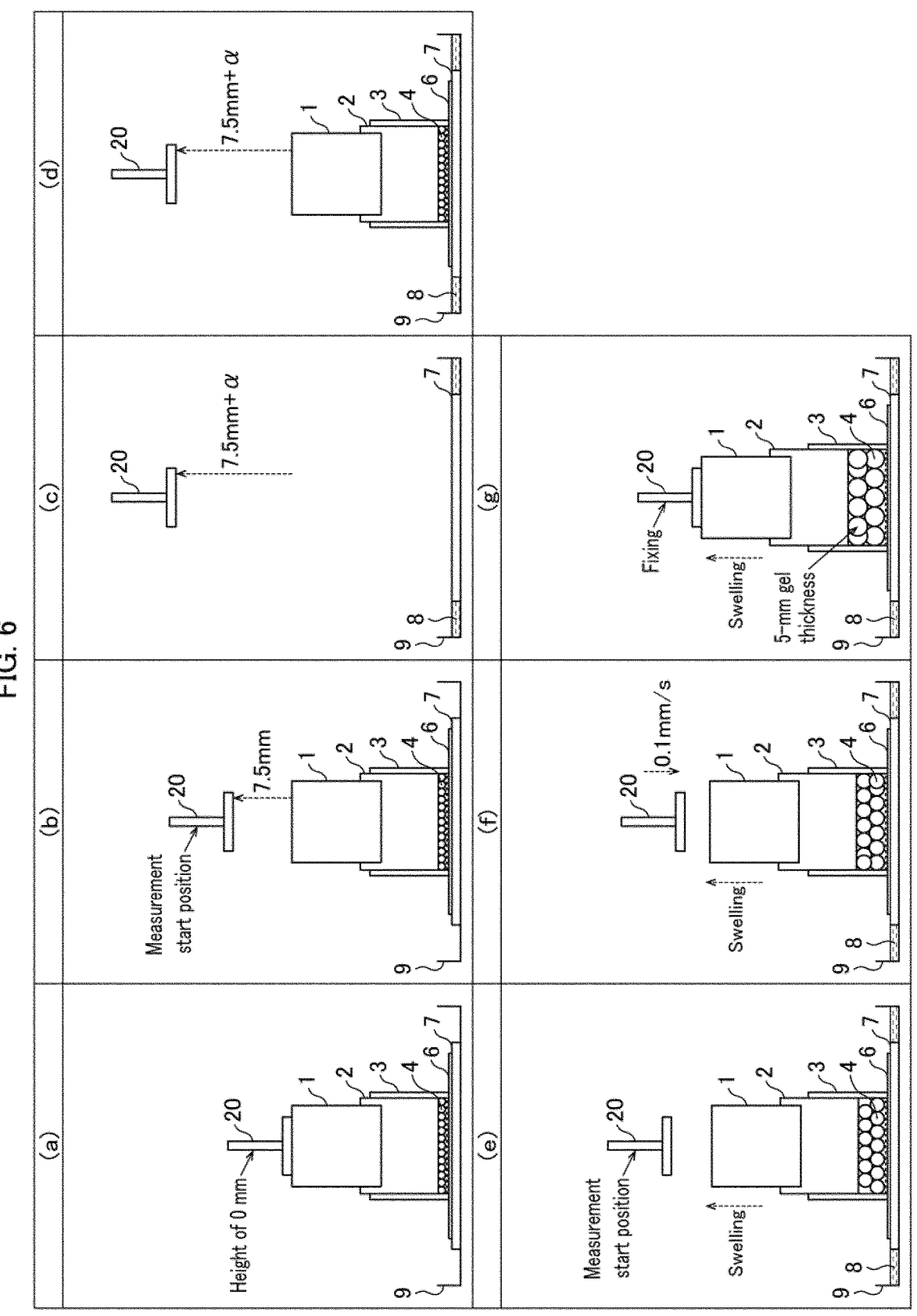
FIG. 6 is a view for explaining a procedure by which the method for measuring the gel expansion force and gel expansion speed of the water-absorbing resin in accordance with an embodiment of the present invention is carried out.

Next, as illustrated in (c) of FIG. 6, the upper pressure plate 20 was manually raised further from the "measurement start position (7.5 mm)" so as not to come into contact with the upper pressure plate 20, and the cell set A and the paper filter 6 were lifted from above the glass filter 7. After that, a 0.9 mass % aqueous sodium chloride solution 8 was introduced into the SUS tray 9 so as to be at the same level as the height of the upper surface of the glass filter 7. Note that the 0.9 mass % aqueous sodium chloride solution 8 used here was the one that had a liquid temperature adjusted to 23° C.±0.5° C. At this time, care was taken to prevent air bubbles from entering the glass filter 7.

In this state, as illustrated in (d) of FIG. 6, the paper filter 6 was placed again in the central part of the glass filter 7, and the cell set A was gently placed in the central part of the paper filter 6 to start swelling of the water-absorbing resin. Further, time measurement was started simultaneously with the placement of the cell set A on the paper filter 6. After the start of swelling, as illustrated in (e) of FIG. 6, the upper pressure plate 20 was manually lowered to the above-described "measurement start position (7.5 mm)" immediately.

Next, at a time point 25 seconds earlier than the time point at which the "5-mm gel thickness reach time" was reached when counted from the start of swelling, "Start Test" was clicked on the test execution screen to cause the upper pressure plate 20 to automatically lower at a speed of 0.1 mm per second as illustrated in (f) of FIG. 6. The reason why the upper pressure plate 20 was caused to start lowering 25 seconds earlier as described above is that the upper pressure plate 20 lowered by 2.5 mm at the time point at which the "5-mm gel thickness reach time" was reached when counted from the start of swelling, so that the upper pressure plate 20 was brought into contact with the upper surface of the weight 1 in the cell set A. Thus, at the time point at which the "5-mm gel thickness reach time" was reached when counted from the start of swelling, the upper pressure plate and the upper surface of the weight 1 in the cell set A came into contact with each other, and, as illustrated in (g) of FIG. 6, the force of the particulate hydrogel pushing up the piston 2 and the weight 1 was continuously measured for 60 minutes at intervals of 0.5 seconds from the time point, as the measurement start point, at which the upper pressure plate and the upper surface of the weight 1 in the cell set A came into contact with each other.

Then, by analyzing, on Microsoft Excel, the force of the particulate hydrogel pushing up the piston and the weight obtained by the above-described 60-minute measurement, the gel expansion force and the gel expansion speed of the water-absorbing resin were calculated.

That is, on Microsoft Excel, the greatest force among the pushing forces in a period of time until after 1000 seconds had passed since the start of measurement (0 second) was determined and was considered to be the gel expansion force (N).

Further, a graph with the horizontal axis as the measurement time (minutes) and the vertical axis as the pushing force (N) was created on Microsoft Excel, and in the graph, a slope of a curve shown by data indicating until after 100 seconds had passed since the start of measurement (0 second) was calculated by the SLOPE function, and the calculated value was considered to be the gel expansion speed (unit: none).

Note that the gel expansion force and the gel expansion speed in the present invention were average values from the results of the above-described measurement carried out twice with use of the same sample (water-absorbing resin).

[Ratio of Volume of Particles Having Cavity Volume Ratio of 15 Volume % or More and Ratio of Volume of Particles Having Void Volume Ratio of 1 Volume % or Less]

A ratio (unit:volume %) of a volume of particles having a cavity volume ratio of 15 volume % or more and a ratio (unit:volume %) of a volume of particles having a void volume ratio of 1 volume % or less, to a total volume of the water-absorbing resin in accordance with an embodiment of the present invention, were found by acquiring three-dimensional image data of the water-absorbing resin with use of Microfocus X-ray CT system (inspeXio SMX-100CT; manufactured by Shimadzu Corporation), analyzing the three-dimensional image data with use of high-speed three-dimensional analysis software (TRI/3D-VOL-FCS64; manufactured by Ratoc System Engineering Co., Ltd.), and then performing calculation with use of statistical analysis software (JMP (registered trademark)) 14 (SAS Institute Inc., Cary, NC, USA) and Microsoft Excel. To find the cavity volume ratio and the void volume ratio, water-absorbing resins having a particle size of 300 μm to 600 μm were used. Specifically, respective pieces of three-dimensional image data of a water-absorbing resin having a particle size of 500 μm to 600 μm, a water-absorbing resin having a particle size of 425 μm to 500 μm, and a water-absorbing resin having a particle size of 300 μm to 425 μm were acquired with use of the Microfocus X-ray CT system, and were subjected to analysis with use of the high-speed three-dimensional analysis software, and thereafter, analysis results of the respective pieces of three-dimensional image data were subjected to collective calculation with use of the JMP and the Excel.

A specific calculation method will be described by taking a water-absorbing resin having a particle size of 500 μm to 600 μm as an example. First, a method for extracting a water-absorbing resin having a particle size of 500 μm to 600 μm will be described. First, JIS standard sieves (The IIDA TESTING SIEVE; manufactured by Sieve Factory Iida Co., Ltd.; diameter: 8 cm; respective mesh sizes of the sieves: 600 μm, 500 μm, 425 μm, and 300 μm) were stacked on top of each other in descending order of mesh size from top, and a receiver (manufactured by Sieve Factory Iida Co., Ltd.; diameter: 8 cm) was placed on the bottom. Next, 10.0 g of water-absorbing resin was introduced into the top sieve (mesh size of the sieve: 600 μm) and was covered with a lid (manufactured by Sieve Factory Iida Co., Ltd.; diameter: 8 cm). Next, a stacked set consisting of the lid, the four sieves, and the receiver was shaken for 5 minutes with use of IIDA SIEVE SHAKER (TYPE: ES-65 type, SER. No. 0632). After shaking, only the water-absorbing resin that had remained on the sieve having a mesh size of 500 μm was extracted, and this water-absorbing resin was considered to be a water-absorbing resin having a particle size of 500 μm to 600 μm. The above-described operation was carried out in a room having a temperature adjusted to 20.0° C. to 25.0° C. and having a humidity adjusted to between 35% and 50%. Note that in the above-described operation, in a case where a water-absorbing resin having a particle size of 425 μm to 500 μm is extracted, only the water-absorbing resin that has remained on the sieve having a mesh size of 425 μm is extracted, and in a case where a water-absorbing resin having a particle size of 300 μm to 425 μm is extracted, only the water-absorbing resin that has remained on the sieve having a mesh size of 300 μm is extracted.

Next, 0.3 g of thermosetting spherical fine particles (EPO-STAR MV1002; manufactured by Nippon Shokubai Co., Ltd.) was introduced into a plastic lid-equipped cylindrical container (having an inner diameter of approximately 1 cm and a height of approximately 5 cm), and then, 0.1 g of water-absorbing resin having a particle size of 500 μm to 600 μm was introduced. A resulting mixture was shaken well so that the water-absorbing resin was uniformly dispersed in the thermosetting spherical fine particles. In this way, a sample was prepared. Next, the cylindrical container was fixed to a sample table of the Microfocus X-ray CT system with a double-sided tape affixed to the bottom surface of the cylindrical container. After that, three-dimensional image data was acquired under the conditions described below.

TABLE 1

| X-ray tube voltage (kV): 50 | Number of views: 3000 |
|---|---|
| X-ray tube current (μA): 40 | Average number: 5 |
| Inch size (inch): 4.0 | Number of times of multi-rotation: None |
| X-ray filter: None | Smoothing: YZ |
| SDD (mm): 500 | Slice thickness (mm): 0.009 |
| SRD (mm): 40 | Distance between slices (mm): 0.010 |
| Z (mm): 112 | Scaling coefficient: 50 |
| X (mm): 0 | BHC data: None |
| Y (mm): 0 | Fine mode: Available |
| CT mode 1: CBCT | FOV XY (mm): 5.0 |
| CT mode 2: Normal scan | FOV Z (mm): 4.0 |
| Scan angle: Full scan | Voxel size (mm/voxel): 0.010 |

Next, with use of the high-speed three-dimensional analysis software, analysis was carried out in accordance with the following procedure.

1. From the menu, Particle Measurement>3D Particles>Particle Separation>Giant Particle Separation were selected.

2. In the Binarize tab on the EVC panel, L-W was selected. With the W value left at the default value, the L value was changed from the default value to a value larger by "1", and a circular measurement target region was extracted. Next, this processing was applied to all sliced images. The image data extracted by this operation was designated as (A) and stored in bin5ch (b5) on the BC panel.

3. In the Binarize tab on the EVC panel, L-W was selected. With the W value left at the default value, the L value was changed from the default value to "37580", and the whole water-absorbing resin in the measurement target region was extracted. Next, this processing was applied to all sliced images. The particle image data extracted by this operation was designated as (B) and stored in binDch (bD) on the BC panel.

4. Based on the particle image data (B), Ers Sm1 was first selected in the Binary tab on the EVC panel to remove particles with a particle size of 10 voxels or less, which were considered as noise. Next, in the Binary tab on the EVC panel, Invert was selected to invert the region where the particles were extracted and the region where no particle was extracted. Next, in the Binary tab on the EVC panel, Ers Sm1 was selected to remove particles with a particle size of 1 voxel or less, which were considered as noise. Then, in the 3D tab on the EVC panel, Labeling was selected, and then the volume and Max were selected, so that only the region with the largest volume was extracted. Here, after it was confirmed that Label Count was displayed as 1, Invert was selected again in the Binary tab on the EVC panel, so that noise was removed in the measurement target region, and all particles were extracted in the state in which voids were filled. The particle image data extracted by these operations was designated as (C) and stored in bin2ch (b2) on the BC panel.

5. In the LOp tab (inter-channel logical operation processing), "2" was selected for target 1, and "D" was selected for target 2. Further, "SUB" was selected, and Execute was pressed to subtract the particle image data (B) from the particle image data (C). After that, in the Binary tab on the EVC panel, Ers Sm1 was selected to remove particles with a particle size of 1 voxel or less, which were considered as noise, so that voids were extracted. The particle image data extracted by these operations was designated as (D) and stored in bin6ch (b6) on the BC panel.

6. Based on the particle image data (C), 8-connected neighborhood was selected in the 3D tab on the EVC panel, dilation processing was performed twice, and then erosion processing was performed twice. The particle image data extracted by this operation was designated as (E) and stored in bin1ch (b1) on the BC panel.

7. In the LOp tab (inter-channel logical operation processing), "1" was selected for target 1, and "2" was selected for target 2. Further, "SUB" was selected, and Execute was pressed to subtract the particle image data (C) from the particle image data (E). By this operation, cavities were extracted. The obtained particle image data was designated as (F) and stored in bin7ch (b7) on the BC panel.

8. Based on the particle image data (E), Small Particle Extraction was selected on the Giant Particle Separation panel (Large Particle Extraction was not selected), and "0" was set for each of Constriction Proportion, Repair Filter Size, and Repair Mrg Sm1 Diameter, so that separation and color sorting of particles were performed.

9. In the 3D tab on the EVC panel, Labeling was selected. Further, Coordinate Value (Cycle) was selected, and Fine Particle Size was set to "100" to perform a separation operation for particles. The particle image data extracted by these operations was designated as (G) and stored in bin1ch (b1) on the BC panel.

10. From the menu, Particle Measurement>Voids in 3D Particles>Post-Separation Measurement were selected.

11. Calculation processing was performed by, on the Post-Separation Measurement panel, selecting Voxel as a unit, selecting Edge Particle Removal, selecting Surface Area Calculation and Void Calculation as measurement items, and then selecting Binary 5ch as a measurement ROI designation.

12. Data obtained by the calculation processing in the step 10 above was extracted in CSV format of Excel.

By the above operations, data of volume (unit: $mm^3$), void volume (unit: $mm^3$), and cavity volume (unit: $mm^3$) were obtained for each particle for all of the water-absorbing resins existing in the measurement target region. Note that the void volume and cavity volume on a per-particle basis are values calculated in a state in which the voids and the cavities are filled in the water-absorbing resin. Further, in the measurement target region, there is a water-absorbing resin containing about 50 to 500 particles.

Next, analysis was performed on the water-absorbing resin having a particle size of 425 μm to 500 μm and the water-absorbing resin having a particle size of 300 μm to 425 μm in the same procedure as the above-described procedure.

Next, all data on volume (unit: $mm^3$), void volume (unit: $mm^3$), and cavity volume (unit: $mm^3$) obtained by the above operations for each particle of the water-absorbing resins having a particle size of 300 μm to 600 μm were imported into one worksheet in Excel. Note that the file format of Excel used here is XLSX format.

Next, on the worksheet, the void volume ratio (unit: volume %) was calculated for each particle based on Formula (4) below.

$$\text{Void volume ratio} = H/(I-J) \times 100 \qquad \text{Formula (4)}$$

where

H is a void volume (unit: mm³),

I is a volume (unit: mm³), and

J is a cavity volume (unit: mm³).

Next, on the worksheet, the cavity volume ratio (unit: volume %) was calculated for each particle based on Formula (5) below.

$$\text{Cavity volume ratio} = J/(I-H)\times 100 \qquad \text{Formula (5)}$$

where

H is a void volume (unit: mm³),

I is a volume (unit: mm³), and

J is a cavity volume (unit: mm³).

Next, on the worksheet, the true volume (unit: mm³) was calculated for each particle based on Formula (6) below.

$$\text{True volume} = I-H-J \qquad \text{Formula (6)}$$

where

H is a void volume (unit: mm³),

I is a volume (unit: mm³), and

J is a cavity volume (unit: mm³).

Next, the void volume ratio, cavity volume ratio, and true volume obtained by the above operations for each particle of the water-absorbing resins having a particle size of 300 μm to 600 μm were all imported into statistical analysis software (JMP) to prepare a data table.

Then, the ratio (unit:volume %) of a volume of particles having a void volume ratio of 1 volume % or less and the ratio (unit:volume %) of a volume of particles having a cavity volume ratio of 15 volume % or more were calculated according to the following procedure.

1. First, in the analysis function of the statistical analysis software (JMP), Univariate Distribution was selected, a column in which the true volume was input in "Y, Columns" was selected, OK was pressed, and the sum of the summary statistics in the analysis result was determined, so that the sum (unit: mm³) of the true volume of the whole water-absorbing resin was calculated. A value of the sum obtained here is considered to be (K).

2. Next, only a water-absorbing resin having a void volume ratio of 1 volume % or less was selected using the data filtering function of the statistical analysis software (JMP).

3. Next, in the analysis function of the statistical analysis software (JMP), Univariate Distribution was selected, a column in which the true volume was input in "Y, Columns" was selected, OK was pressed, and the sum of the summary statistics in the analysis result was determined, so that the sum (unit: mm³) of the true volume of the water-absorbing resin selected in the operation in Step 2 above was calculated. A value of the sum obtained here is considered to be (L).

4. Next, only a water-absorbing resin having a cavity volume ratio of 15 volume % or more was selected using the data filtering function of the statistical analysis software (JMP).

5. Next, in the analysis function of the statistical analysis software (JMP), Univariate Distribution was selected, a column in which the true volume was input in "Y, Columns" was selected, OK was pressed, and the sum of the summary statistics in the analysis result was determined, so that the sum (unit: mm³) of the true volume of the water-absorbing resin selected in the operation in Step 4 above was calculated. A value of the sum obtained here is considered to be (M).

6. Then, from the values (K), (L), and (M) calculated by the operations in Steps 1, 3, and 5 above, respectively, the ratio (unit:volume %) of a volume of particles having a void volume ratio of 1 volume % or less and the ratio (unit: volume %) of a volume of particles having a cavity volume ratio of 15 volume % or more were calculated based on Formulae (7) and (8) below.

$$\text{Ratio of volume of particles having void volume ratio of 1 volume \% or less} = L/K\times 100 \qquad \text{Formula (7)}$$

$$\text{Ratio of volume of particles having cavity volume ratio of 15 volume \% or more} = M/K\times 100 \qquad \text{Formula (8)}$$

[Absorption Capacity Under Load on Second Urination]

The absorption capacity under load (unit: cm³/g) of the water-absorbing resin in accordance with an embodiment of the present invention on second urination was measured by the following method. Note that this absorption capacity under load is an index for evaluating, in a simulation manner, the ability of a thin absorbent body having been swollen on first urination to absorb urine even under load on second and subsequent urinations. An absorbent body in a disposable diaper is often a mixture of a water-absorbing resin and a fiber material such as wood-ground pulp. In the present invention, the absorption capacity under load was measured on the assumption that a condition where thinning is most advanced is such that no fiber material such as wood-ground pulp is used, i.e. an absorbent body substantially composed of 100% water-absorbing resin is used.

Figure 7:
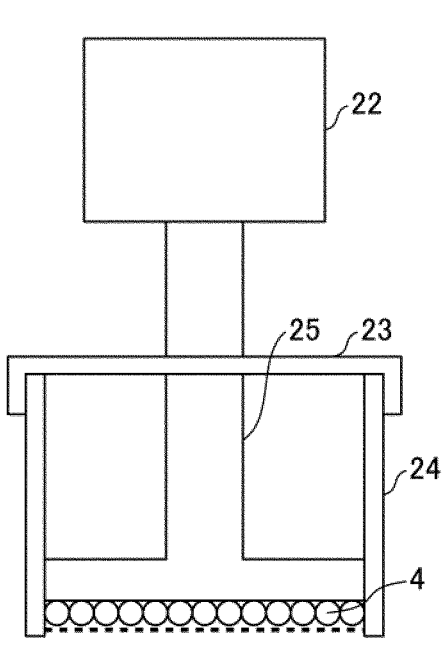
FIG. 7 is a view for explaining the configuration of a cell set B used at the measurement of an absorption capacity under load of the water-absorbing resin in accordance with an embodiment of the present invention on second urination.

A specific measurement method is as follows. As illustrated in FIG. 7, first, a cylinder 24, a piston 25, a lid 23 with two through holes to be placed on the cylinder 24, and a weight 22 used at the measurement of the SFC were prepared, 3.0 g of water-absorbing resin 4 was placed in the cylinder 24, and the piston 25 was inserted into the cylinder 24 in which the water-absorbing resin 4 had been placed. At this time, care was taken not to cause the water-absorbing resin 4 to be caught between the inner wall of the cylinder 24 and the piston 25. Then, the lid 23 was set, and the weight 22 was set on top of the piston 25. Note that, hereinafter, a set group, which was prepared here, consisting of the water-absorbing resin 4, the cylinder 24, the piston 25, the lid 23, and the weight 22 is referred to as cell set B. Note that the operations so far were carried out in a room having a temperature adjusted to 23° C.±0.5° C. and having a humidity adjusted to be between 35% and 50%, and the subsequent operations were carried out in a room having a temperature adjusted to 23° C.±0.5° C. and having a humidity adjusted to between 35% and 60%.

Next, as in FIG. 3, a surface heater 10 set at 23° C. was placed on a horizontal experimental table, a SUS tray 9 used at the measurement of the AAP was placed on the surface heater 10, a glass filter 7 used at the measurement of the AAP was placed in the central part of the SUS tray 9 such that a surface of the glass filter 7 with little unevenness faced upwards, a paper filter 6 used at the measurement of the AAP was placed in the central part of the glass filter 7 such that a surface of the paper filter 6 with little unevenness faced upwards, and the cell set B, instead of the cell set A, was placed in the central part of the paper filter 6.

Figure 8:
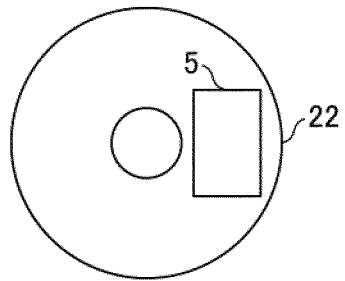
FIG. 8 is a view illustrating a position at which a white vinyl tape is affixed to an upper surface of a weight in cell set B.

Further, to measure vertical position information of the weight 22 when the water-absorbing resin was swollen, a laser displacement meter manufactured by Keyence Corporation (amplifier unit 15: IL-1000; sensor head 14: IL-S100; power supply unit 16: KZ-U3) was installed. The measurement environment refers to a state in which, in FIG. 3, the cell set A was replaced by the cell set B, and the 0.9 mass % aqueous sodium chloride solution was not introduced into the SUS tray 9. Note that, as illustrated in FIG. 3, the sensor head 14 was installed so that a laser to be emitted from the sensor head 14 was emitted vertically to an upper surface of the weight 22 in the cell set B. Further, a white vinyl tape (product name: De-Lead Type Vinyl Tape, part number: 21-10W; manufactured by Nitto Denko Corporation) 5 was affixed to the upper surface of the weight 22 in a portion where the laser was to be emitted, so that the emitted laser was properly reflected. A state in which the vinyl tape was affixed to the upper surface of the weight 22 is illustrated in FIG. 8. This made it possible to measure the vertical position information (numerical data) of the weight 22. The position information of the weight 22 measured by the sensor head 14 was transmitted to a data logger (manufactured by GRAPH-TEC Corporation; midiLOGGER GL220) 17 and was stored in the data logger 17. Note that the data logger 17 was connected between the amplifier unit 15 and the power supply unit 16 and was set so that the position information of the weight 22 could be continuously stored at intervals of 1 second.

Under this measurement environment, 40 g of a 0.9 mass % aqueous sodium chloride solution 8 having a temperature adjusted to 23° C.±0.5° C. was taken into a 60-milliliter syringe and was added to the inside of the cylinder 24 over about 6 seconds while a tip of the syringe was inserted into the hole of the lid 23 in the cell set B. This commenced swelling of the water-absorbing resin 4. Note that, simultaneously with the start of the addition of the 0.9 mass % aqueous sodium chloride solution, reading of the position information of the weight 22 by the laser displacement meter was started. After 2 minutes passed since the start of the addition of the 0.9 mass % aqueous sodium chloride solution, 50 g of a 0.9 mass % aqueous sodium chloride solution having a temperature adjusted to 23° C.±0.5° C. was added again to the inside of the cylinder over about 6 seconds through the hole of the lid in the cell set B with use of a syringe in the same manner as above (start of the second liquid absorption). After 8 minutes passed since the start of the second addition of the 0.9 mass % aqueous sodium chloride solution (start of the second liquid absorption), the reading of the position information of the weight 22 by the laser displacement meter was finished (end of the measurement).

Then, the absorption capacity under load in a period of time until after 8 minutes had passed since the start of the second addition of the 0.9 mass % aqueous sodium chloride solution was calculated, as absorption capacity (unit: cm³/g) under load on second urination, based on Formula (4) below.

Absorption capacity under load on second urination=$A \times C/1000/B$     Formula (4), wherein A is a cross-sectional area (unit: mm²) of an inner diameter of the cylinder in which the water-absorbing resin was placed, B is an amount (unit: g) of water-absorbing resin placed in the cylinder, and C is a vertical movement distance of the weight 22 (distance (unit: mm) from the position information (numerical value) of the weight 22 at the start of the second liquid absorption to the position information (numerical value) of the weight 22 at the end of the measurement), which was calculated by subjecting the position information of the weight read by the laser displacement meter to analysis on Microsoft Excel, from the time point at which the second addition of the 0.9 mass % aqueous sodium chloride solution was started to the time point at which 8 minutes passed since the start of the second addition of the 0.9 mass % aqueous sodium chloride solution.

[Initial Color Tone]

An initial color tone of the water-absorbing resin in accordance with an embodiment of the present invention was measured in the Hunter's Lab color system. As a measurement device, LabScan (registered trademark) XE manufactured by HunterLab was used, reflection measurement was selected as a measurement condition, and 1.75 inches was selected as a measurement diameter. As an initial color tone measurement container, a container having an internal diameter of 9.5 cm and a height of 0.6 cm and made of aluminum or stainless steel was used.

In a specific measurement method, first of all, the water-absorbing resin was introduced into the initial color tone measurement container until the water-absorbing resin was spilt. Next, the water-absorbing resin that had been heaped to a level higher than the upper surface of the container was leveled off with a ruler or the like. Then, in an atmosphere in which a room temperature was 20° C. to 25° C. and a relative humidity was 50% RH, a WI value of a surface of the water-absorbing resin was measured.

Note that, in a case where the water-absorbing resin is a water-absorbing resin immediately after production or before shipment from a factory or a water-absorbing resin stored for 1 year or less after production in an atmosphere in which a temperature is 30° C. or less and a relative humidity is 50% RH, a color tone of such a water-absorbing resin was regarded as an initial color tone.

TABLE 2

| | | | Physical properties of particulate hydrogel | | | Physical properties of water-absorbing resin after surface-crosslinking | | | | | | |
|---|---|---|---|---|---|---|---|---|---|---|---|---|
| | | | | | | Water-absorbing resin | | AAP | | Solid | | 5-mm gel thickness |
| | | | Particulate hydrogel | D50 [μm] | σζ | after surface-crosslinking | CRC [g/g] | (0.7 psi) [g/g] | SFC*[1] | content [mass %] | D50 [μm] | reach time [sec] |
| Examples | 1 | (1) | 320 | 0.91 | (1) | | 28.0 | 25.8 | 49 | 98.0 | 362 | 120 |
| | 2 | (2) | 330 | 0.92 | (2) | | 28.0 | 26.0 | 40 | 97.9 | 363 | 101 |
| | 3 | (3) | 400 | 0.95 | (3-4) | | 28.5 | 25.7 | 33 | 97.4 | 365 | 126 |
| | 4 | (4) | 410 | 0.94 | (4-4) | | 27.7 | 25.0 | 40 | 97.6 | 334 | 134 |
| Comparative | 1 | (1') | 350 | 0.93 | (1') | | 27.0 | 24.4 | 67 | 98.1 | 438 | 160 |
| Examples | 2 | (2') | 400 | 0.97 | (2'-4) | | 27.7 | 24.5 | 56 | 98.3 | 405 | 216 |
| | 3 | (3') | 550 | 1.01 | (3'-2) | | 27.1 | 24.5 | 63 | 98.0 | 354 | 173 |
| | 4 | (4') | 540 | 1.04 | (4'-2) | | 25.5 | 22.3 | 78 | 97.8 | 351 | 177 |
| | 5 | (5') | 910 | 1.02 | (5') | | 30.3 | 22.7 | 89 | 98.2 | 343 | 188 |
| | 6 | (6') | 750 | 1.01 | (6'-2) | | 34.0 | 23.1 | 10 | 99.0 | 361 | 253 |

TABLE 2-continued

| | | | | Physical properties of water-absorbing resin after surface-crosslinking | | | |
| | | | | | | | |
| | Water-absorbing resin after surface-crosslinking | Gel expansion force [N] | Gel expansion speed [—] | Ratio of volume of particles having cavity volume ratio of 15 volume % or more to total volume of water-absorbing resin [volume %] | Ratio of volume of particles having void volume ratio of 1 volume % or less to total volume of water-absorbing resin [volume %] | Ratio of volume of particles having cavity volume ratio of 15 volume % or more and void volume ratio of 1 volume % or less to total volume of water-absorbing resin [volume %] | Absorption capacity under load on second urination [cm³/g] |
|---|---|---|---|---|---|---|---|
| Examples | 1 (1) | 28.8 | 9.0 | 45 | 88 | 36 | 15.1 |
| | 2 (2) | 29.1 | 10.0 | 46 | 89 | 38 | 15.2 |
| | 3 (3-4) | 28.1 | 10.2 | 44 | 79 | 31 | 14.9 |
| | 4 (4-4) | 31.8 | 12.1 | 44 | 75 | 29 | 14.1 |
| Comparative Examples | 1 (1') | 24.5 | 7.9 | 71 | 53 | 40 | 13.3 |
| | 2 (2'-4) | 22.6 | 7.3 | 44 | 78 | 30 | 12.9 |
| | 3 (3'-2) | 24.1 | 7.8 | 39 | 83 | 29 | 13.2 |
| | 4 (4'-2) | 22.2 | 7.1 | 38 | 81 | 27 | 12.8 |
| | 5 (5') | 22.2 | 7.1 | 53 | 60 | 38 | 12.7 |
| | 6 (6'-2) | 20.2 | 6.5 | 20 | 95 | 15 | 12.3 |

*[1])Unit: $\times 10^{-7}$ cm³ · sec/g

As is clear from Table 2, the water-absorbing resin in accordance with an embodiment of the present invention can have a high gel expansion force under a load of 4.83 kPa, and more preferably can have a high gel expansion force and a high gel expansion speed, while maintaining a value of the AAP, and thus has an increased absorption capacity under load over the conventional water-absorbing resins (comparative examples) even when second urination occurs (when further absorbing urine under load) after having absorbed urine on first urination. That is, the water-absorbing resin in accordance with an embodiment of the present invention has an increased absorption capacity under load on the second urination over the conventional water-absorbing resins (comparative examples).

In contrast, the water-absorbing resins in Comparative Examples are low in gel expansion force under a load of 4.83 kPa and further are low in both gel expansion force and gel expansion speed, and thus have insufficient absorption capacity under load on the second urination.

Next, absorbent bodies were prepared by using the water-absorbing resins after surface-crosslinking obtained in Examples 1 to 4 and Comparative Examples 1 to 6. A method for preparing the absorbent bodies is described below.

[Preparation of Absorbent Body]

Figures 9, 10:
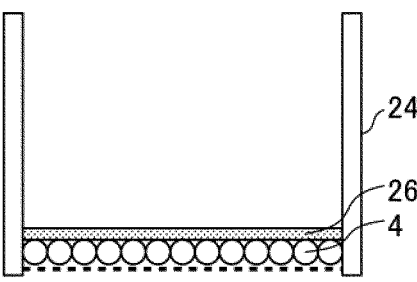
FIG. 9 is a view illustrating a state in which a water-absorbing resin is placed in a cylinder used at the measurement of SFC, and a nonwoven fabric simulating a liquid permeable top sheet is placed on the water-absorbing resin.
FIG. 10 is a view for explaining the configuration of a cell set C used at the measurements of the amount of liquid trapped under load of an absorbent body in accordance with an embodiment of the present invention.

In the present invention, the absorbent body was prepared on the assumption that a condition where thinning of an absorbent article such as a disposable diaper is most advanced is such that no fiber material such as wood-ground pulp is used, i.e. an absorbent body substantially composed of 100% water-absorbing resin is used. Specifically, as illustrated in FIG. 9, 3.0 g of water-absorbing resin 4 was placed in the cylinder 24 used at the measurement of the SFC, and a nonwoven fabric (manufacturing method: spun-bond method; thickness: 0.1 mm, mass per unit area: 13 g/m², liquid diffusion area: 18 mm²) 26 simulating a liquid permeable top sheet was placed on the water-absorbing resin 4 in the cylinder 24. Note that, as the nonwoven fabric 26, a nonwoven fabric cut into a circular shape having a diameter 0.2 mm shorter than the inner diameter of the cylinder 24 was used. Further, the thickness, mass per unit area, and liquid diffusion area of the nonwoven fabric 26 were measured by the measurement method described later. Next, the amount of liquid trapped under load was measured with use of the prepared absorbent body. The following description shows a measurement method. Further, Table 3 shows the measurement results.

[Amount of Liquid Trapped Under Load of Absorbent Body]

The amount of liquid trapped under load of the absorbent body in accordance with an embodiment of the present invention was measured by the method described below. Note that, in contrast to the above-described absorption capacity under load on second urination, in the case of the amount of liquid trapped under load of the absorbent body, a 0.9 mass % aqueous sodium chloride solution (preferably colored with 0.04 g of brilliant blue FCF (blue no. 1) relative to 1000 g of the 0.9 mass % aqueous sodium chloride solution) having a liquid temperature changed to 36.5° C.±0.5° C., which is assumed to be a temperature of human urine, was used. Unlike the absorption capacity under load on second urination, the amount of liquid trapped under load of the absorbent body is intended for proper evaluation for the function of the absorbent body on the assumption that the absorbent body is actually used in an absorbent article.

A specific measurement method is as follows. As illustrated in FIG. 10, first, a piston 25, a lid 23 with two through holes to be placed on the cylinder 24, and a weight 22 used at the measurement of the SFC were prepared, and the piston 25 was inserted into the cylinder 24 in which the prepared absorbent body had been placed. At this time, care was taken not to cause the water-absorbing resin 4 and the nonwoven fabric 26 to be caught between the inner wall of the cylinder 24 and the piston 25. Then, the lid 23 was set, and the weight 22 was set on top of the piston 25. Note that, hereinafter, a set group, which was prepared here, consisting of the water-absorbing resin 4, the nonwoven fabric 26, the cylinder 24, the piston 25, the lid 23, and the weight 22 is referred to as cell set C. Note that the operations so far were carried out in a room having a temperature adjusted to 23° C.±0.5° C. and having a humidity adjusted to be between 35% and 50%, and the subsequent operations were carried out in a room having a temperature adjusted to 23° C.±0.5° C. and having a humidity adjusted to between 35% and 60%.

Figure 11:
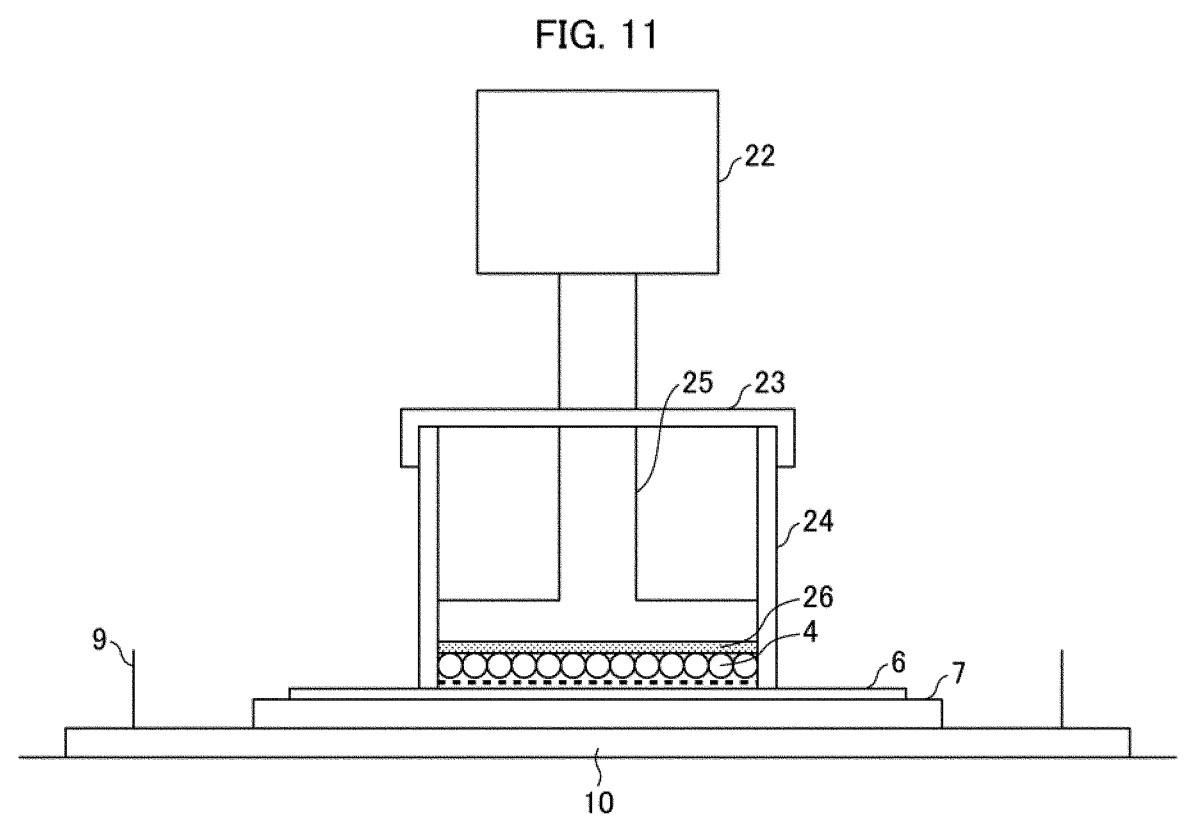

The mass of the cell set C was measured, and the measured mass was considered to be (A). Next, as illustrated in the measurement environment in FIG. 11, a surface heater 10 set at 23° C. was placed on a horizontal experimental table, a SUS tray 9 used at the measurement of the AAP was placed on the surface heater 10, a glass filter 7 used at the measurement of the AAP was placed in the central part of the SUS tray 9 such that a surface of the glass filter 7 with little unevenness faced upwards, a paper filter 6 used at the measurement of the AAP was placed in the central part of the glass filter 7 such that a surface of the paper filter 6 with little unevenness faced upwards, and the cell set C was placed in the central part of the paper filter 6.

Under this measurement environment, 40 g of a 0.9 mass % aqueous sodium chloride solution (preferably colored with 0.04 g of brilliant blue FCF (blue no. 1) relative to 1000 g of the 0.9 mass % aqueous sodium chloride solution) having a temperature adjusted to 36.5° C.±0.5° C. was taken into a 60-milliliter syringe and was added to the inside of the cylinder 24 over about 6 seconds while a tip of the syringe was inserted into the hole of the lid 23 in the cell set C. This commenced swelling of the water-absorbing resin 4. Then, after 2 minutes had passed by measurement since the start of the addition of the 0.9 mass % aqueous sodium chloride solution, the mass of the cell set C was measured, and the measured mass was considered to be (B). Note that, in moving the cell set C from the paper filter 6 to an electronic balance or the like at the mass measurement, the cell set C was not disassembled and maintained its original structure. Specifically, the outer wall portion of the cylinder 24 was held with hands and carried, and the lid 23, the piston 25, and the weight 22 set above the piston 25 were not touched. Further, at the mass measurement, the paper filter 6 on the glass filter 7 was replaced with an unused one simultaneously. Then, after the mass had been measured, the cell set C was placed again in the central part of the unused paper filter 6, and 40 g of a 0.9 mass % aqueous sodium chloride solution (preferably colored with 0.04 g of brilliant blue FCF (blue no. 1) relative to 1000 g of the 0.9 mass % aqueous sodium chloride solution) having a temperature adjusted to 36.5° C.±0.5° C. was added again to the inside of the cylinder 24 over about 6 seconds through the hole of the lid 23 in the cell set C with use of the syringe in the same manner as above. Note that the operation for the measurement of the mass of the cell set C and the operation for the replacement of the paper filter 6 were performed within 30 seconds. That is, the second addition of the 0.9 mass % aqueous sodium chloride solution was started within 2 minutes and 30 seconds by measurement after the start of the first addition of the 0.9 mass % aqueous sodium chloride solution. Then, after 3 minutes had passed by measurement since the start of the second addition of the 0.9 mass % aqueous sodium chloride solution, the mass of the cell set C was measured, and the measured mass was considered to be (C). Note that, in moving the cell set C from the paper filter 6 to the electronic balance or the like at the mass measurement, the cell set C was not disassembled and maintained its original structure, as in the case described above.

Then, the amount of liquid trapped under load in a period of time until after 3 minutes had passed since the start of the second addition of the 0.9 mass % aqueous sodium chloride solution was calculated, as an amount (unit: g) of liquid trapped under load of absorbent body on second urination, based on Formula (5) below. Note that the amount of liquid trapped under load of an absorbent body on second urination is an index for evaluating the ability of an absorbent body having been swollen on first urination to absorb urine even under load on the second and subsequent urinations.

$$\text{Amount of liquid trapped under load of absorbent body on second urination} = (C) - (B) \qquad \text{Formula (5)}$$

Further, a total of the amount of liquid trapped under load in a period of time until after 2 minutes had passed since the start of the first addition of the 0.9 mass % aqueous sodium chloride solution and the amount of liquid trapped under load in a period of time until after 3 minutes had passed since the start of the second addition of the 0.9 mass % aqueous sodium chloride solution was calculated, as a total amount (unit: g) of liquid trapped under load of absorbent body on first and second urinations, based on Formula (6) below.

$$\text{Total amount of liquid trapped under load of absorbent body on first and second urinations} = (C) - (A) \qquad \text{Formula (6)}$$

Note that, in this measurement, a case where, in measuring the (B) above and the (C) above, the 0.9 mass % aqueous sodium chloride solution remains on the layer of the swollen water-absorbing resin is considered to be a case impossible to measure. That is, in a case where the 0.9 mass % aqueous sodium chloride solution remains on the layer of the swollen water-absorbing resin at the measurement by visual observation, the "amount of liquid trapped under load of absorbent body on second urination" of the water-absorbing resin and a "total amount of liquid trapped under load of absorbent body on first and second urinations" are considered to be unmeasurable.

[Thickness of Nonwoven Fabric]

The thickness (unit: mm) of the nonwoven fabric used at the measurement of the amount of liquid trapped under load of the absorbent body was measured by the following measurement method. That is, it was measured with use of a dial thickness gauge large type (thickness measuring instrument) (manufactured by Ozaki Manufacturing Co., Ltd.; model number: J-B; gauge head: upper and lower anvils of φ50 mm). The measurement points were 5 times at different sites, and a measured value was an average value of 5 points. During the thickness measurement, the thickness was measured by slowly releasing the hands from a handle to minimize a pressure applied onto the nonwoven fabric.

[Mass Per Unit Area of Nonwoven Fabric]

The mass per unit area (unit: $g/m^2$) of the nonwoven fabric used at the measurement of the amount of liquid trapped under load of the absorbent body was measured by the following measurement method. That is, a mass of a nonwoven fabric cut into a rectangle of 10 cm or more in length and 40 cm in width or more was measured, and the measured mass was divided by an area of the cut nonwoven fabric to calculate the mass per unit area.

[Liquid Diffusion Area of Nonwoven Fabric]

The liquid diffusion area (unit: $mm^2$) of the nonwoven fabric used at the measurement of the amount of liquid trapped under load of the absorbent body was measured by the following measurement method. That is, a 30-cm-diameter stainless steel sieve having a gauze of 2 mm in mesh size and 0.9 mm in wire diameter was placed on a horizontal experimental table, and a nonwoven fabric cut in 10 cm square was placed on the gauze of the sieve. With a 1-milliliter syringe fitted with a needle having a diameter of 0.50 mm, 1.00 g of a 0.9 mass % aqueous sodium chloride solution containing 20 ppm of brilliant blue FCF (blue no. 1) was weighed, and the aqueous sodium chloride solution was injected into the center of the nonwoven fabric on the sieve in a direction vertical to the nonwoven fabric. At this time, sufficient space was provided between the bottom of the gauze of the sieve and the experimental table to prevent the aqueous sodium chloride solution having once passed through the nonwoven fabric and the gauze of the sieve from adhering to the gauze of the sieve or the nonwoven fabric again. At the time point at which the nonwoven fabric absorbed the aqueous sodium chloride solution and the diffusion of the liquid was completed, the area where the aqueous sodium chloride solution was diffused was measured.

TABLE 3

|  |  | Water-absorbing resin after surface-crosslinking | Amount of liquid trapped under load of absorbent body on second urination [g] | Total amount of liquid trapped under load of absorbent body on first and second urinations [g] |
|---|---|---|---|---|
| Examples | 5 | (1) | 37.2 | 74.9 |
|  | 6 | (2) | 37.4 | 75.1 |
|  | 7 | (3-4) | 37.3 | 75.3 |
|  | 8 | (4-4) | 35.5 | 73.0 |
| Comparative | 7 | (1') | 34.0 | 71.4 |
| Examples | 8 | (2'-4) | 33.0 | 70.2 |
|  | 9 | (3'-2) | 33.8 | 71.2 |
|  | 10 | (4'-2) | 32.8 | 70.0 |
|  | 11 | (5') | 32.7 | 70.0 |
|  | 12 | (6'-2) | 31.6 | 68.7 |

As is clear from Table 3, the absorbent body using the water-absorbing resin that has a high gel expansion force under a load of 4.83 kPa, and more preferably has a high gel expansion force and a high gel expansion speed, while maintaining a value of the AAP, has an increased amount of liquid trapped under load over the conventional ones even when second urination occurs (when further absorbing urine under load) after having absorbed urine on first urination. That is, the absorbent body using such a water-absorbing resin has an increased amount of liquid trapped under load on the second urination over the conventional ones. Further, the absorbent body using such a water-absorbing resin also has an increased total amount of liquid trapped under load on the first and second urinations over the conventional ones.

In contrast, since each water-absorbing resin in Comparative Examples is low in gel expansion force under a load of 4.83 kPa and further is low in both gel expansion force and gel expansion speed, the absorbent body using such a water-absorbing resin has an insufficient amount of liquid trapped under load on the second urination. Further, the absorbent body using such a water-absorbing resin has an insufficient total amount of liquid trapped under load on the first and second urinations.

An embodiment of the present invention includes the following aspects.

[1] An absorbent body including a water-absorbing resin having a gel expansion force under a load of 4.83 kPa of 26 N or more.

[2] The absorbent body according to [1], wherein a ratio of a mass of the water-absorbing resin to a total mass of the absorbent body is 75 mass % or more and 100 mass % or less.

[3] An absorbent article including an absorbent body recited in [1] or [2].

[4] A water-absorbing resin having a gel expansion force under a load of 4.83 kPa of 26 N or more.

[5] The water-absorbing resin according to [4], wherein a gel expansion speed under a load of 4.83 kPa of the water-absorbing resin is 8.5 or more.

[6] The water-absorbing resin according to [4] or [5], wherein a volume of particles having a cavity volume ratio of 15 volume % or more accounts for 40 volume % or more of a total volume of the water-absorbing resin.

[7] The water-absorbing resin according to any one of [4] to [6], wherein a volume of particles having a void volume ratio of 1 volume % or less accounts for 65 volume % or more of a total volume of the water-absorbing resin.

[8] The water-absorbing resin according to any one of [4] to [7], wherein an absorption capacity without load (CRC) of the water-absorbing resin is 25 g/g or more.

[9] The water-absorbing resin according to any one of [4] to [8], wherein an absorption capacity under load (AAP) under a load of 4.83 kPa of the water-absorbing resin is 20 g/g or more.

[10] The water-absorbing resin according to any one of [4] to [9], wherein saline flow conductivity (SFC) of the water-absorbing resin is $15(\times 10^{-7} \ cm^3 \cdot sec/g)$ or more and $55(\times 10^{-7} \ cm^3 \cdot sec/g)$ or less.

[11] The water-absorbing resin according to any one of [4] to [10], wherein a mass average particle diameter (D50) of said water-absorbing resin is 250 μm or more and 550 μm or less, a mass of particles having a particle diameter of more than 710 μm accounts for 2 mass % or less of a total mass of said water-absorbing resin, and a mass of particles having a particle diameter of less than 150 μm accounts for 3 mass % or less of the total mass of said water-absorbing resin.

INDUSTRIAL APPLICABILITY

An absorbent body in accordance with an embodiment of the present invention, for example, in a case where the absorbent body has been used in an absorbent article, such as a thin disposable diaper, having an absorbent body with a low proportion of fiber material such as pulp, has an increased amount of liquid trapped under load on second and subsequent urinations over the conventional ones, and, as a result, enables the absorbent article such as a disposable diaper to have an improved liquid trapping function over the conventional ones. Further, a water-absorbing resin in accordance with an embodiment of the present invention, for example, even in a case where the water-absorbing resin has been used in an absorbent body of an absorbent article, such as a thin disposable diaper, having an absorbent body with a low proportion of fiber material such as pulp, has an increased absorption capacity under load on the second and subsequent urinations, and, as a result, enables the absorbent body to have an increased amount of liquid trapped under load on the second and subsequent urinations. Thus, the absorbent body and the water-absorbing resin in accordance with an embodiment of the present invention can be suitably used in, for example, an absorbent article, such as a thin disposable diaper, having a low proportion of fiber material such as pulp. Further, the absorbent body and the water-absorbing resin in accordance with an embodiment of the present invention can be suitably used in various applications such as absorbent articles (sanitary napkins, incontinence articles, etc.) including disposable diapers, agricultural and horticultural water retaining agents, and industrial waterproofing agents.

REFERENCE SIGNS LIST

1: Weight
2: Piston
3: Cylinder
4: Water-absorbing resin
5: Vinyl tape
6: Paper filter
7: Glass filter
8: 0.9 mass % aqueous sodium chloride solution 9: SUS tray
10: Surface heater
11: Stand
12: Muff
13: Clamp
14: Sensor head
15: Amplifier unit
16: Power supply unit
17: Data logger
18: Laser emission direction
19: Load cell
20: Upper pressure plate
21: Lower pressure plate
22: Weight
23: Lid
24: Cylinder
25: Piston
26: Nonwoven fabric

The invention claimed is:

1. An absorbent body comprising a water-absorbing resin having a gel expansion force under a load of 4.83 kPa of 26 N or more and having a saline flow conductivity (SFC) of $15(\times 10^{-7} \text{ cm}^3 \cdot \text{sec/g})$ or more and $55(\times 10^{-7} \text{ cm}^3 \cdot \text{sec/g})$ or less.

2. The absorbent body according to claim 1, wherein a ratio of a mass of said water-absorbing resin to a total mass of said absorbent body is 75 mass % or more and 100 mass % or less.

3. An absorbent article comprising an absorbent body recited in claim 1.

4. A water-absorbing resin having a gel expansion force under a load of 4.83 kPa of 26 N or more and having a saline flow conductivity (SFC) of $15(\times 10^{-7} \text{ cm}^3 \cdot \text{sec/g})$ or more and $55(\times 10^{-7} \text{ cm}^3 \cdot \text{sec/g})$ or less.

5. The water-absorbing resin according to claim 4, wherein a gel expansion speed under a load of 4.83 kPa of said water-absorbing resin is 8.5 or more.

6. The water-absorbing resin according to claim 4, wherein a volume of particles having a cavity volume ratio of 15 volume % or more accounts for 40 volume % or more of a total volume of said water-absorbing resin.

7. The water-absorbing resin according to claim 4, wherein a volume of particles having a void volume ratio of 1 volume % or less accounts for 65 volume % or more of a total volume of said water-absorbing resin.

8. The water-absorbing resin according to claim 4, wherein an absorption capacity without load (CRC) of said water-absorbing resin is 25 g/g or more.

9. The water-absorbing resin according to claim 4, wherein an absorption capacity under load (AAP) under a load of 4.83 kPa of said water-absorbing resin is 20 g/g or more.

10. The water-absorbing resin according to claim 4, wherein a mass average particle diameter (D50) of said water-absorbing resin is 250 µm or more and 550 µm or less, a mass of particles having a particle diameter of more than 710 µm accounts for 2 mass % or less of a total mass of said water-absorbing resin, and a mass of particles having a particle diameter of less than 150 µm accounts for 3 mass % or less of the total mass of said water-absorbing resin.

* * * * *